United States Patent
Kakehi et al.

(10) Patent No.: US 10,774,148 B2
(45) Date of Patent: Sep. 15, 2020

(54) COMPOSITION FOR TREATING IL-6-RELATED DISEASES

(71) Applicant: CHUGAI SEIYAKU KABUSHIKI KAISHA, Tokyo (JP)

(72) Inventors: Takahiro Kakehi, Tokyo (JP); Akinori Yamada, Tokyo (JP); Yoshimasa Ishida, Tokyo (JP)

(73) Assignee: Chugai Seiyaku Kabushiki Kaisha, Tokyo (JP)

(*) Notice: Subject to any disclaimer, the term of this patent is extended or adjusted under 35 U.S.C. 154(b) by 0 days.

(21) Appl. No.: 15/553,609

(22) PCT Filed: Feb. 26, 2016

(86) PCT No.: PCT/JP2016/055768
§ 371 (c)(1),
(2) Date: Aug. 25, 2017

(87) PCT Pub. No.: WO2016/136933
PCT Pub. Date: Sep. 1, 2016

(65) Prior Publication Data
US 2018/0148509 A1    May 31, 2018

(30) Foreign Application Priority Data

Feb. 27, 2015    (JP) ................ 2015-037933

(51) Int. Cl.
| | | |
|---|---|---|
| C07K 16/28 | (2006.01) |
| A61K 39/395 | (2006.01) |
| A61K 45/00 | (2006.01) |
| A61K 39/00 | (2006.01) |

(52) U.S. Cl.
CPC .......... *C07K 16/2866* (2013.01); *A61K 45/00* (2013.01); *A61K 39/395* (2013.01); *A61K 2039/505* (2013.01); *A61K 2039/54* (2013.01); *A61K 2039/545* (2013.01); *C07K 2317/56* (2013.01)

(58) Field of Classification Search
CPC ............... A61K 2300/00; A61K 45/06; A61K 2039/505; A61K 31/225; A61K 9/0019; A61K 331/513; A61K 38/47; C07K 14/70517; C07K 16/303; C12N 15/85; G01N 33/574
See application file for complete search history.

(56) References Cited

U.S. PATENT DOCUMENTS

| | | |
|---|---|---|
| 4,689,299 A | 8/1987 | Insel |
| 4,801,687 A | 1/1989 | Ngo |
| 5,126,250 A | 6/1992 | McDonough et al. |
| 5,202,253 A | 4/1993 | Esmon et al. |
| 5,322,678 A | 6/1994 | Morgan et al. |
| 5,501,854 A | 3/1996 | Raso |
| 5,585,089 A | 12/1996 | Queen et al. |
| 5,639,641 A | 6/1997 | Pedersen et al. |
| 5,670,373 A | 9/1997 | Kishimoto |
| 5,795,965 A | 8/1998 | Tsuchiya et al. |
| 5,817,790 A | 10/1998 | Tsuchiya et al. |
| 5,830,478 A | 11/1998 | Raso et al. |
| 5,935,935 A | 8/1999 | Connelly et al. |
| 5,945,311 A | 8/1999 | Lindhofer et al. |
| 5,990,286 A | 11/1999 | Khawli et al. |
| 6,309,636 B1 | 10/2001 | do Couto et al. |
| 6,329,511 B1 | 12/2001 | Vasquez et al. |
| 6,485,943 B2 | 11/2002 | Stevens et al. |
| 6,677,436 B1 | 1/2004 | Sato et al. |
| 6,723,319 B1 | 4/2004 | Ito et al. |
| 6,737,056 B1 | 5/2004 | Presta |
| 6,821,505 B2 | 11/2004 | Ward |
| 6,884,879 B1 | 4/2005 | Baca et al. |
| 6,913,747 B1 | 7/2005 | Co et al. |
| 7,052,873 B2 | 5/2006 | Tsuchiya |
| 7,122,637 B2 | 10/2006 | Presta |
| 7,217,797 B2 | 5/2007 | Hinton et al. |
| 7,276,585 B2 | 10/2007 | Lazar et al. |
| 7,479,543 B2 | 1/2009 | Tsuchiya et al. |
| 8,217,147 B2 | 7/2012 | Stavenhagen et al. |
| 8,470,316 B2 | 6/2013 | Yasunami |
| 8,562,991 B2 | 10/2013 | Igawa et al. |
| 8,623,355 B2 | 1/2014 | Okada et al. |
| 8,771,686 B2 | 7/2014 | Ishida |
| 8,945,558 B2 | 2/2015 | Kobara |
| 9,079,949 B1 | 7/2015 | Andrien et al. |

(Continued)

FOREIGN PATENT DOCUMENTS

| | | |
|---|---|---|
| AR | 068564 | 11/2009 |
| AU | 2009290162 | 4/2010 |

(Continued)

OTHER PUBLICATIONS

Chihara et al, PNAS, 2011, vol. 108, No. 9, pp. 3701-3706.*
Petkova et al., "Enhanced half-life of genetically engineered human IgG1 antibodies in a humanized FcRn mouse model: potential application in humorally mediated autoimmune disease," Int. Immunol., Dec. 2006; 18(12):1759-69. Epub Oct. 31, 2006.
Vaccaro et al., "Divergent activities of an engineered antibody in murine and human systems have implications for therapeutic antibodies," Proc. Natl. Acad. Sci. USA, Dec. 5, 2006; 103(49):18709-14. Epub Nov. 20, 2006.
U.S. Appl. No. 15/575,027, filed Nov. 17, 2017, Yamamura et al.
Cocco et al., "In Vitro Generation of Long-lived Human Plasma Cells," J. Immunol., Dec. 15, 2012;189(12):5773-85. doi:10.4049/jimmunol.1103720. Epub Nov. 16, 2012.
Jego et al., "Interleukin-6 is a growth factor for nonmalignant human plasmablasts," Blood, Mar. 2001 15:97(6):1817-22.

(Continued)

*Primary Examiner* — Bridget E Bunner
*Assistant Examiner* — Fozia Hamud
(74) *Attorney, Agent, or Firm* — Fish & Richardson P.C.

(57) ABSTRACT

The present invention provides a pharmaceutical composition for treating IL-6-related diseases containing an IL-6 inhibitor as an active ingredient, wherein the pharmaceutical composition is routinely administered after a short-interval dosing period where the same dose as the routine dose is administered at a shorter interval than the routine dosing interval.

29 Claims, 5 Drawing Sheets
Specification includes a Sequence Listing.

(56) References Cited

U.S. PATENT DOCUMENTS

| | | |
|---|---|---|
| 9,096,651 B2 | 8/2015 | Igawa et al. |
| 9,228,017 B2 | 1/2016 | Igawa et al. |
| 9,260,516 B2 | 2/2016 | Nishimoto et al. |
| 10,066,018 B2 | 9/2018 | Igawa et al. |
| 10,253,091 B2 | 4/2019 | Igawa et al. |
| 10,472,623 B2 | 11/2019 | Igawa et al. |
| 2001/0001663 A1 | 5/2001 | Kishimoto et al. |
| 2002/0098193 A1 | 7/2002 | Ward |
| 2002/0142374 A1 | 10/2002 | Gallo et al. |
| 2002/0164339 A1 | 11/2002 | Do et al. |
| 2002/0187150 A1 | 12/2002 | Mihara et al. |
| 2003/0059937 A1 | 3/2003 | Ruben et al. |
| 2003/0224397 A1 | 12/2003 | Lowman et al. |
| 2004/0018540 A1 | 1/2004 | Yamamura et al. |
| 2004/0071706 A1 | 4/2004 | Ito et al. |
| 2004/0081651 A1 | 4/2004 | Karpusas et al. |
| 2004/0133357 A1 | 7/2004 | Zhong et al. |
| 2004/0236080 A1 | 11/2004 | Aburatani et al. |
| 2005/0014934 A1 | 1/2005 | Hinton et al. |
| 2005/0095243 A1 | 5/2005 | Chan et al. |
| 2005/0118163 A1 | 6/2005 | Mizushima et al. |
| 2005/0130224 A1 | 6/2005 | Saito et al. |
| 2005/0142133 A1 | 6/2005 | Lazar et al. |
| 2005/0142635 A1 | 6/2005 | Tsuchiya et al. |
| 2005/0214278 A1 | 9/2005 | Kakuta et al. |
| 2005/0244403 A1 | 11/2005 | Lazar et al. |
| 2005/0260711 A1 | 11/2005 | Datta et al. |
| 2005/0261229 A1 | 11/2005 | Gillies et al. |
| 2006/0014156 A1 | 1/2006 | Rabbani et al. |
| 2006/0019342 A1 | 1/2006 | Dall Acqua et al. |
| 2006/0063228 A1 | 3/2006 | Kasaian et al. |
| 2006/0134113 A1 | 6/2006 | Mihara et al. |
| 2006/0134709 A1 | 6/2006 | Stavenhagen et al. |
| 2006/0141456 A1 | 6/2006 | Edwards et al. |
| 2006/0153860 A1 | 7/2006 | Cho et al. |
| 2006/0194280 A1 | 8/2006 | Dillon et al. |
| 2006/0275282 A1 | 12/2006 | Moore et al. |
| 2006/0292147 A1 | 12/2006 | Yoshizaki et al. |
| 2007/0036785 A1 | 2/2007 | Kishimoto et al. |
| 2007/0037734 A1 | 2/2007 | Rossi et al. |
| 2007/0041978 A1 | 2/2007 | Hattori et al. |
| 2007/0059312 A1 | 3/2007 | Baca et al. |
| 2007/0134234 A1 | 6/2007 | Smith et al. |
| 2007/0148164 A1 | 6/2007 | Farrington et al. |
| 2007/0160598 A1 | 7/2007 | Dennis et al. |
| 2007/0212357 A1 | 9/2007 | Pons et al. |
| 2007/0269371 A1 | 11/2007 | Krummen et al. |
| 2007/0280945 A1 | 12/2007 | Stevens et al. |
| 2008/0075712 A1 | 3/2008 | Hattori et al. |
| 2008/0145367 A1 | 6/2008 | Bove et al. |
| 2008/0166756 A1 | 7/2008 | Tsuchiya et al. |
| 2009/0263392 A1 | 10/2009 | Igawa et al. |
| 2009/0269335 A1 | 10/2009 | Nakashima et al. |
| 2009/0291076 A1 | 11/2009 | Morichika et al. |
| 2009/0324589 A1 | 12/2009 | Igawa et al. |
| 2010/0003254 A1 | 1/2010 | Hattori et al. |
| 2010/0004429 A1 | 1/2010 | Kai et al. |
| 2010/0008907 A1 | 1/2010 | Nishimoto et al. |
| 2010/0015133 A1 | 1/2010 | Igawa et al. |
| 2010/0055092 A1 | 3/2010 | Hasegawa et al. |
| 2010/0061986 A1 | 3/2010 | Takahashi |
| 2010/0216187 A1 | 8/2010 | Lasters et al. |
| 2010/0239577 A1 | 9/2010 | Igawa et al. |
| 2010/0247523 A1 | 9/2010 | Kano et al. |
| 2010/0292443 A1 | 11/2010 | Sabbadini et al. |
| 2010/0297697 A1 | 11/2010 | Ambrosius et al. |
| 2010/0298542 A1 | 11/2010 | Igawa et al. |
| 2010/0316636 A1 | 12/2010 | Radin et al. |
| 2011/0044986 A1 | 2/2011 | Biere-Citron et al. |
| 2011/0076275 A1 | 3/2011 | Igawa et al. |
| 2011/0098450 A1 | 4/2011 | Igawa et al. |
| 2011/0111406 A1 | 5/2011 | Igawa et al. |
| 2011/0150869 A1 | 6/2011 | Mitsunaga |
| 2011/0150888 A1 | 6/2011 | Foltz et al. |
| 2011/0245473 A1 | 10/2011 | Igawa et al. |
| 2012/0065379 A1 | 3/2012 | Igawa et al. |
| 2012/0071634 A1 | 3/2012 | Igawa et al. |
| 2012/0183539 A1 | 7/2012 | Maeda |
| 2012/0238729 A1 | 9/2012 | Kuramochi et al. |
| 2012/0253016 A1 | 10/2012 | Igawa et al. |
| 2012/0301460 A1* | 11/2012 | Bao .................. A61K 38/47 424/133.1 |
| 2013/0011866 A1 | 1/2013 | Igawa et al. |
| 2013/0101581 A1 | 4/2013 | Kuramochi et al. |
| 2013/0202588 A1 | 8/2013 | Nishimura |
| 2013/0303396 A1 | 11/2013 | Igawa et al. |
| 2013/0317203 A1 | 11/2013 | Igawa et al. |
| 2013/0336963 A1 | 12/2013 | Igawa et al. |
| 2014/0105889 A1 | 4/2014 | Igawa et al. |
| 2014/0234340 A1 | 8/2014 | Igawa et al. |
| 2014/0363428 A1 | 12/2014 | Igawa et al. |
| 2015/0050269 A1 | 2/2015 | Igawa et al. |
| 2015/0056182 A1 | 2/2015 | Igawa et al. |
| 2015/0166666 A1 | 6/2015 | Igawa et al. |
| 2015/0274809 A1 | 10/2015 | Igawa et al. |
| 2015/0284465 A1 | 10/2015 | Igawa et al. |
| 2015/0299313 A1 | 10/2015 | Igawa et al. |
| 2015/0315278 A1 | 11/2015 | Igawa et al. |
| 2015/0353630 A1 | 12/2015 | Igawa et al. |
| 2016/0039912 A1 | 2/2016 | Mimoto et al. |
| 2016/0046693 A1 | 2/2016 | Igawa et al. |
| 2016/0139117 A1 | 5/2016 | Yamamura et al. |
| 2016/0159915 A1 | 6/2016 | Igawa et al. |
| 2016/0244526 A1 | 8/2016 | Igawa et al. |
| 2017/0002080 A1 | 1/2017 | Igawa et al. |
| 2017/0022270 A1 | 1/2017 | Igawa et al. |
| 2017/0121412 A1 | 5/2017 | Igawa et al. |
| 2018/0142027 A1 | 5/2018 | Igawa et al. |
| 2018/0149573 A1 | 5/2018 | Yamamura et al. |
| 2018/0258161 A1 | 9/2018 | Igawa et al. |
| 2019/0085085 A1 | 3/2019 | Igawa et al. |
| 2019/0211081 A1 | 7/2019 | Igawa et al. |

FOREIGN PATENT DOCUMENTS

| | | |
|---|---|---|
| CA | 1 332 367 | 10/1994 |
| CA | 2 203 182 | 5/1996 |
| CA | 2 443 294 | 10/2002 |
| CA | 2 523 577 | 11/2004 |
| CA | 2 531 482 | 1/2005 |
| CA | 2 549 467 | 7/2005 |
| CA | 2 560 953 | 9/2005 |
| CA | 2 625 773 | 4/2007 |
| CA | 2 626 688 | 4/2007 |
| CA | 2 647 846 | 10/2007 |
| CA | 2 648 644 | 10/2007 |
| CA | 2 911 000 | 10/2007 |
| CA | 2 700 394 | 4/2009 |
| CA | 2 700 498 | 4/2009 |
| CA | 2 700 986 | 4/2009 |
| CN | 101849006 | 9/2010 |
| CN | 103476793 | 12/2013 |
| CN | 101874042 | 9/2018 |
| EP | 0 182 495 | 5/1986 |
| EP | 0 361 902 | 4/1990 |
| EP | 0 329 185 | 4/1994 |
| EP | 0 628 639 | 12/1994 |
| EP | 0 783 893 | 7/1997 |
| EP | 0 791 359 | 8/1997 |
| EP | 0 983 767 | 3/2000 |
| EP | 1 004 315 | 5/2000 |
| EP | 1 069 185 | 1/2001 |
| EP | 1 074 268 | 2/2001 |
| EP | 1 334 731 | 8/2003 |
| EP | 1 374 900 | 1/2004 |
| EP | 1 510 943 | 3/2005 |
| EP | 1 690 550 | 8/2006 |
| EP | 1 701 979 | 9/2006 |
| EP | 1 707 215 | 10/2006 |
| EP | 1 712 237 | 10/2006 |
| EP | 2 236 604 | 10/2006 |
| EP | 1 728 801 | 12/2006 |
| EP | 1 733 740 | 12/2006 |
| EP | 1 773 391 | 4/2007 |

(56) References Cited

FOREIGN PATENT DOCUMENTS

| | | |
|---|---|---|
| EP | 1 601 697 | 5/2007 |
| EP | 1 847 602 | 10/2007 |
| EP | 1 870 459 | 12/2007 |
| EP | 1 941 907 | 7/2008 |
| EP | 1 941 908 | 7/2008 |
| EP | 1 967 207 | 9/2008 |
| EP | 1 967 209 | 9/2008 |
| EP | 1 977 763 | 10/2008 |
| EP | 1 990 060 | 11/2008 |
| EP | 2 006 381 | 12/2008 |
| EP | 2 009 101 | 12/2008 |
| EP | 2 031 064 | 3/2009 |
| EP | 2 123 302 | 11/2009 |
| EP | 2 174 667 | 4/2010 |
| EP | 2 194 066 | 6/2010 |
| EP | 2 196 220 | 6/2010 |
| EP | 2 196 541 | 6/2010 |
| EP | 2 202 245 | 6/2010 |
| EP | 2 206 775 | 7/2010 |
| EP | 2 275 443 | 1/2011 |
| EP | 2 305 306 | 4/2011 |
| EP | 2 330 193 | 6/2011 |
| EP | 2 409 991 | 1/2012 |
| EP | 2 578 233 | 4/2013 |
| EP | 2 639 305 | 9/2013 |
| JP | S61-117457 | 6/1986 |
| JP | S63-52890 | 3/1988 |
| JP | 2-028200 | 1/1990 |
| JP | H02-163085 | 6/1990 |
| JP | H03-500644 | 2/1991 |
| JP | 07-67688 | 3/1995 |
| JP | 09-506001 | 6/1997 |
| JP | 2002-505086 | 2/2002 |
| JP | 2004-028926 | 1/2004 |
| JP | 2004-511426 | 4/2004 |
| JP | 2005-501514 | 1/2005 |
| JP | 2005-101105 | 3/2005 |
| JP | 2005-535341 | 11/2005 |
| JP | 2005-378266 | 12/2005 |
| JP | 2006-512087 | 4/2006 |
| JP | 2007-525171 | 9/2007 |
| JP | 2010-505436 | 2/2010 |
| JP | 5144499 | 2/2013 |
| JP | 2013-518131 | 5/2013 |
| JP | 2013-165716 | 8/2013 |
| JP | 2013-541594 | 11/2013 |
| JP | 5334319 | 11/2013 |
| JP | 5484060 | 5/2014 |
| JP | 5717624 | 5/2015 |
| JP | 2015-130883 | 7/2015 |
| JP | 5787446 | 9/2015 |
| KR | 2006/0010765 | 2/2006 |
| KR | 2007/0035482 | 3/2007 |
| KR | 2007/0068385 | 6/2007 |
| KR | 2008/0098504 | 11/2008 |
| KR | 2010/0074220 | 7/2010 |
| KR | 2010/0074221 | 7/2010 |
| RU | 2147442 | 4/2000 |
| RU | 2195960 | 1/2003 |
| RU | 2225721 | 3/2004 |
| RU | 2232773 | 7/2004 |
| RU | 2266298 | 12/2005 |
| RU | 2430111 | 9/2011 |
| RU | 2010/116152 | 11/2011 |
| TW | 201021829 | 6/2010 |
| TW | 2013/02219 | 1/2013 |
| WO | WO 89/01343 | 2/1989 |
| WO | WO 91/12023 | 8/1991 |
| WO | WO 92/19759 | 6/1995 |
| WO | WO 95/014710 | 6/1995 |
| WO | WO 95/33844 | 12/1995 |
| WO | WO 96/11020 | 4/1996 |
| WO | WO 96/12503 | 5/1996 |
| WO | WO 96/27011 | 9/1996 |
| WO | WO 97/09351 | 3/1997 |
| WO | WO 97/20858 | 6/1997 |
| WO | WO 98/03546 | 1/1998 |
| WO | WO 98/42377 | 10/1998 |
| WO | WO 99/08707 | 2/1999 |
| WO | WO 99/018212 | 4/1999 |
| WO | WO 99/43713 | 9/1999 |
| WO | WO 99/47170 | 9/1999 |
| WO | WO 99/51743 | 10/1999 |
| WO | WO 99/58572 | 11/1999 |
| WO | WO 00/14220 | 3/2000 |
| WO | WO 01/30854 | 5/2001 |
| WO | WO 01/82899 | 11/2001 |
| WO | WO 02/34292 | 5/2002 |
| WO | WO 02/060919 | 8/2002 |
| WO | WO 02/072605 | 9/2002 |
| WO | WO 02/080969 | 10/2002 |
| WO | WO 03/000883 | 1/2003 |
| WO | WO 03/020949 | 3/2003 |
| WO | WO 03/068259 | 8/2003 |
| WO | WO 03/068260 | 8/2003 |
| WO | WO 2003/070760 | 8/2003 |
| WO | WO 03/105757 | 12/2003 |
| WO | WO 2003/107009 | 12/2003 |
| WO | WO 2004/016740 | 2/2004 |
| WO | WO 2004/035752 | 4/2004 |
| WO | WO 2004/039826 | 5/2004 |
| WO | WO 2004/068931 | 8/2004 |
| WO | WO 2004/092219 | 10/2004 |
| WO | WO 2004/096273 | 11/2004 |
| WO | WO 2004/113387 | 12/2004 |
| WO | WO 2005/005604 | 1/2005 |
| WO | WO 2005/035753 | 4/2005 |
| WO | WO 2005/035754 | 4/2005 |
| WO | WO 2005/035756 | 4/2005 |
| WO | WO 2005/037315 | 4/2005 |
| WO | WO 2005/047327 | 5/2005 |
| WO | WO 2005/056606 | 6/2005 |
| WO | WO 2005/059106 | 6/2005 |
| WO | WO 2005/061000 | 7/2005 |
| WO | WO 2005/067620 | 7/2005 |
| WO | WO 2005/080429 | 9/2005 |
| WO | WO 2005/090405 | 9/2005 |
| WO | WO 2005/092925 | 10/2005 |
| WO | WO 2005/112564 | 12/2005 |
| WO | WO 2005/123126 | 12/2005 |
| WO | WO 2006/004663 | 1/2006 |
| WO | WO 2006/019447 | 2/2006 |
| WO | WO 2006/023144 | 3/2006 |
| WO | WO 2006/030200 | 3/2006 |
| WO | WO 2006/030220 | 3/2006 |
| WO | WO 2006/044908 | 4/2006 |
| WO | WO 2006/047340 | 5/2006 |
| WO | WO 2006/047350 | 5/2006 |
| WO | WO 2006/050491 | 5/2006 |
| WO | WO 2006/066598 | 6/2006 |
| WO | WO 2006/067913 | 6/2006 |
| WO | WO 2006/070286 | 7/2006 |
| WO | WO 2006/071877 | 7/2006 |
| WO | WO 2006/075668 | 7/2006 |
| WO | WO 2006/082052 | 8/2006 |
| WO | WO 2006/106905 | 10/2006 |
| WO | WO 2006/109592 | 10/2006 |
| WO | WO 2006/119115 | 11/2006 |
| WO | WO 2006/121852 | 11/2006 |
| WO | WO 2007/024535 | 3/2007 |
| WO | WO 2007/043641 | 4/2007 |
| WO | WO 2007/046489 | 4/2007 |
| WO | WO 2007/058194 | 5/2007 |
| WO | WO 2007/060411 | 5/2007 |
| WO | WO 2007/061029 | 5/2007 |
| WO | WO 2007/074880 | 7/2007 |
| WO | WO 2007/076524 | 7/2007 |
| WO | WO 2007/086490 | 8/2007 |
| WO | WO 2007/092772 | 8/2007 |
| WO | WO 2007/108559 | 9/2007 |
| WO | WO 2007/114319 | 10/2007 |
| WO | WO 2007/114325 | 10/2007 |
| WO | WO 2007/116962 | 10/2007 |
| WO | WO 2007/137984 | 12/2007 |

(56) References Cited

FOREIGN PATENT DOCUMENTS

| WO | WO 2007/142325 | 12/2007 |
|---|---|---|
| WO | WO 2007/143168 | 12/2007 |
| WO | WO 2008/020079 | 2/2008 |
| WO | WO 2008/043822 | 4/2008 |
| WO | WO 2008/060785 | 5/2008 |
| WO | WO 2008/090901 | 7/2008 |
| WO | WO 2008/092117 | 7/2008 |
| WO | WO 2008/145141 | 12/2008 |
| WO | WO 2009/006338 | 1/2009 |
| WO | WO 2009/010539 | 1/2009 |
| WO | WO 2009/014263 | 1/2009 |
| WO | WO 2009/036209 | 3/2009 |
| WO | WO 2009/041062 | 4/2009 |
| WO | WO 2009/041613 | 4/2009 |
| WO | WO 2009/041621 | 4/2009 |
| WO | WO 2009/041643 | 4/2009 |
| WO | WO 2009/041734 | 4/2009 |
| WO | WO 2009/044774 | 4/2009 |
| WO | WO 2009/052439 | 4/2009 |
| WO | WO 2009/072604 | 6/2009 |
| WO | WO 2009/100309 | 8/2009 |
| WO | WO 2009/125825 | 10/2009 |
| WO | WO 2009/139822 | 11/2009 |
| WO | WO 2009/148148 | 12/2009 |
| WO | WO 2010/035769 | 4/2010 |
| WO | WO 2010/065078 | 6/2010 |
| WO | WO 2010/106812 | 9/2010 |
| WO | WO 2010/107108 | 9/2010 |
| WO | WO 2010/107109 | 9/2010 |
| WO | WO 2010/107110 | 9/2010 |
| WO | WO 2011/013786 | 2/2011 |
| WO | WO 2011/094593 | 8/2011 |
| WO | WO 2011/111007 | 9/2011 |
| WO | WO 2011/149046 | 12/2011 |
| WO | WO 2011/149051 | 12/2011 |
| WO | WO 2012/063875 | 5/2012 |
| WO | WO 2012/064627 | 5/2012 |
| WO | WO 2012/073992 | 6/2012 |
| WO | WO 2012/118750 | 9/2012 |
| WO | WO 2014/028354 | 2/2014 |
| WO | WO 2014/144080 | 9/2014 |
| WO | WO 2014/144575 | 9/2014 |
| WO | WO 2014/200018 | 12/2014 |
| WO | WO 2016/136933 | 9/2016 |
| WO | WO 2016/186154 | 11/2016 |
| WO | WO 2018/023545 | 11/2018 |

OTHER PUBLICATIONS

Jourdan et al., "An in vitro model of differentiation of memory B cells into plasmablasts and plasma cells including detailed phenotypic and molecular characterization," Blood, Dec. 2009 10:114(25):5173-81. doi:10.1182/blood-2009-07-235960.
Matsumoto et al., "Interleukin-10-Producing Plasmablasts Exert Regulatory Function in Autoimmune Inflammation," Immunity, Dec. 2014 18:41(6):1040-51.doi:10.1016/j.immuni.2014.10.016. Epub Nov. 4, 2014.
International Search Report in International Application No. PCT/JP2016/064818, dated Aug. 16, 2016, 5 pages (with English translation).
International Preliminary Report on Patentability in International Application No.PCT/JP2016/064818, dated Nov. 30, 2017, 6 pages.
U.S. Appl. No. 15/614,842, filed Jun. 6, 2017, Igawa et al.
U.S. Appl. No. 15/725,692, filed Oct. 5, 2017, Igawa et al.
Annual Report 2012, "Integrated Edition Including CSR Report," Chugai Pharmaceutical Co., Ltd., Mar. 27, 2013, 154 pages.
Adams et al., "Humanization of a recombinant monoclonal antibody to produce a therapeutic HER dimerization inhibitor, pertuzumab," Cancer Immunol. Immunother., Jun. 2006; 55:717-727.
Akira et al., "Interleukin-6 in Biology and Medicine," Adv. Immunol., Dec. 31, 1993; 54:1-78.
Algonomics—Tripole® applications [online] [retrieved on Feb. 29, 2012]. Retrieved from the Internet: http://web.archive.org/web20090221052902/http://www.algonomics.com/proteinengineering/tripole_applications.php, 2 pages (Feb. 21, 2009).
Allen et al., "Interchain disulfide bonding in human IgG2 antibodies probed by site-directed mutagenesis," Biochemistry, Apr. 2009; 48(17):3755-66.
Almagro et al., "Humanization of antibodies," Front. Biosci., Jan. 2008; 13:1619-33.
Amersham Biosciences, "Affinity Chromatography: Principles and Methods," Edition AD, 2002; pp. 16-18 & 137.
Amersham Biosciences, "Antibody Purification Handbook," Edition 18-1037-46 [online], [retrieved on Nov. 5, 2015]. Retrieved from the Internet: http://www.promix.ru/manuf/ge/chrom/lit/Antibody_Purification.pdf.
Aricha et al., "Blocking of IL-6 suppresses experimental autoimmune myasthenia gravis," J. Autoimmun. Mar. 2011; 36(2):135-41. doi:10.1016/j.jaut.2010.12.001. Epub Dec. 30, 2010.
Araki et al., "Efficacy of the anti-IL-6 receptor antibody tocilizumab in neuromyelitis optica: a pilot study," Neurology, Apr. 15, 2014;82(15):1302-6.
Araki et al., "Clinical improvement in a patient with neuromyelitis optica following therapy with the anti-IL-6 receptor monoclonal antibody tocilizumab," Mod. Rheumatol. Jul. 2013 ; 23(4) :827-31. doi: 10. 1007/s10165-012-0715-9. Epub Jul. 11, 2012.
Armour et al., "Recombinant human IgG molecules lacking Fcgamma receptor I binding and monocyte triggering activities," Eur. J. Immunol., Aug. 1999; 29(8):2613-24.
Balint et al., "Antibody engineering by parsimonious mutagenesis," Gene., Dec. 27, 1993;137(1):109-18.
Barkhof et al., "Comparison of MRI criteria at first presentation to predict conversion to clinically definite multiple sclerosis," Brain, Nov. 1997;120 ( Pt 11):2059-69.
Bartelds et al., "Clinical response to adalimumab: relationship to anti-adalimumab antibodies and serum adalimumab concentrations in rheumatoid arthritis," Ann. Rheum. Dis., Feb. 2007; 66(7):921-926.
Batra et al., "Pharmacokinetics and biodistribution of genetically engineered antibodies," Curr. Opin. Biotechnol., Dec. 2002;13(6):603-8.
Bayry et al., "Immuno affinity purification of foot and mouth disease virus type specific antibodies using recombinant protein adsorbed to polystyrene wells," J. Virol. Methods, Aug. 1999; 81:21-30.
Beck et al., "Strategies and challenges for the next generation of therapeutic antibodies," Nat. Rev. Immunol., May 2010; 10(5):345-52.
Bender et al., "Immunogenicity, efficacy and adverse events of adalimumab in RA patients," Rheumatol. Int., Jan. 2007; 27(3):269-274.
Bian et al., "Discovery of promiscuous HLA-II-restricted T cell epitopes with TEPITOPE," Methods, Dec. 2004;34(4):468-75.
Binz et al., "Engineering novel binding proteins from nonimmunoglobulin domains," Nat. Biotechnol., Oct. 2005; 23:1257-68.
Branden and Tooze, "Recognition of Foreign Molecules by the Immune System," Introduction to Protein Structure, 2d Ed., Garland Publishing, 1999; 299-323.
Brenner et al., "Errors in genome annotation," Trends in Genetics, Apr. 1999;15:132-133.
Brown et al., "Tolerance of single, but not multiple, amino acid replacements in antibody $V_H$ CDR2: a means of minimizing B cell wastage from somatic hypermutation?" J. Immunol., May 1996; 156(9):3285-91.
Brown et al., "A study of the interactions between an IgG-binding domain based on the B domain of staphylococcal protein A and rabbit IgG," Mol. Biotechnol., Aug. 1998;10(1):9-16.
Burmeister et al., "Crystal structure of the complex of rat neonatal Fc receptor with Fc," Nature, Nov. 24, 1994;372(6504):379-83.
Calbiochem® Buffers, "A guide for the preparation and use of buffers in biological systems," by Chandra Mohan, Ph.D., Copyright© 2003 EMD Biosciences, Inc., an Affiliate of Merck KGaA, Darmstadt, Germany, 37 pages.
Carter, "Bispecific human IgG by design," J. Immunol. Methods, 248:7-15 (Feb. 2001).

(56) References Cited

OTHER PUBLICATIONS

Chaparro-Riggers et al., "Increasing serum half-life and extending cholesterol lowering in vivo by engineering antibody with pH-sensitive binding to PCSK9," J. Biol Chem., 287(14):11090-7 (Mar. 2012).
Chappel et al., "Identification of a secondary Fc gamma RI binding site within a genetically engineered human IgG antibody," J. Biol. Chem., Nov. 25, 1993;268(33):25124-31.
Chappel et al., "Identification of the Fc gamma receptor class I binding site in human IgG through the use of recombinant IgG1/IgG2 hybrid and point-mutated antibodies," Proc. Natl. Acad. Sci. U.S.A., Oct. 15, 1991;88(20):9036-40.
Chau et al., "HuM291(Nuvion), a humanized Fc receptor-nonbinding antibody against CD3, anergizes peripheral blood T cells as partial agonist of the T cell receptor," Transplantation, 71(7):941-50 (Apr. 2001).
Chen et al., "Defective secretion of an immunoglobulin caused by mutations in the heavy chain complementarity determining region 2," J. Exp. Med., 180(2):577-86 (Aug. 1994).
Chen et al., "Generation and analysis of random point mutations in an antibody CDR2 sequence: many mutated antibodies lose their ability to bind antigen," J. Exp. Med., 176(3):855-66 (Sep. 1992).
Chen et al., "Selection and analysis of an optimized anti-VEGF antibody: crystal structure of an affinity-matured Fab in complex with antigen," J. Mol. Biol., Nov. 5, 1999;293(4):865-81.
Chien et al., "Significant structural and functional change of an antigen-binding site by a distant amino acid substitution: proposal of a structural mechanism," Proc. Natl. Acad. Sci. U.S.A., 86(14):5532-6 (Jul. 1989).
Chihara et al., "Autoantibody Producing Cells in Neuromyelitis Optica," Journal of Clinical and Experimental Medicine, 2012;240:534-5 (with English translation).
Chihara et al., "Interleukin 6 signaling promotes anti-aquaporin 4 autoantibody production from plasmablasts in neuromyelitis optica," Proc. Natl. Acad. Sci. U S A., Mar. 1, 2011;108(9):3701-6. doi: 10.1073/pnas.1017385108. Epub Feb. 14, 2011.
Chirino et al., "Minimizing the immunogenicity of protein therapeutics," Drug Discov. Today, 9:82-90 (Jan. 2004).
Choy et al., "Inhibiting interleukin-6 in rheumatoid arthritis," Curr. Rheumatol. Rep., 10(5):413-7 (Oct. 2008).
Christensen et al., "Systemic inflammation in progressive multiple sclerosis involves follicular T-helper, Th17- and activated B-cells and correlates with progression," PLoS One, Mar. 2013;8(3):e57820.
Chu et al., "Accumulation of succinimide in a recombinant monoclonal antibody in mildly acidic buffers under elevated temperatures," Pharm. Res., 24(6):1145-56 (Jun. 2007).
Cole et al., "Human IgG2 variants of chimeric anti-CD3 are nonmitogenic to T cells," J. Immunol., 159(7):3613-21 (Oct. 1997).
Coloma et al., "Position effects of variable region carbohydrate on the affinity and in vivo behavior of an anti-(1→6) dextran antibody," J. Immunol., Feb. 15, 1999;162(4):2162-70.
Comper and Glasgow, "Charge selectivity in kidney ultrafiltration," Kidney Int., 47:1242-51 (May 1995).
Cordoba et al., "Non-enzymatic hinge region fragmentation of antibodies in solution," J. Chromatogr. B. Analyt. Technol. Biomed. Life Sci., 818(2):115-21 (Apr. 2005).
Couto et al., "Anti-BA46 Monoclonal Antibody Mc3. Humanization Using a Novel Positional Consensus and in Vivo and in Vitro Characterization," Cancer Research, 55:1717-1722 (Apr. 1995).
Cuatrecasas et al., "Affinity Chromatography," Methods Enzymol., 1971;12:345-78.
Dall'Acqua et al., "Antibody humanization by framework shuffling," Methods, 36(1):43-60 (May 2005).
Dall'Acqua et al., "Increasing the affinity of a human IgG1 for the neonatal Fc receptor: biological consequences," J. Immunol., Nov. 1, 2002;169(9):5171-80.
Dall'Acqua et al., "Modulation of the effector functions of a human IgG1 through engineering of its hinge region," J. Immunol., 177(2):1129-38 (Jul. 2006).
Damschroder et al., "Framework shuffling of antibodies to reduce immunogenicity and manipulate functional and biophysical properties," Mol. Immunol., 44(11):3049-60 (Apr. 2007).
Datta-Mannan et al., "Monoclonal antibody clearance. Impact of modulating the interaction of IgG with the neonatal Fc receptor," J. Biol. Chem., 282(3):1709-17 (Jan. 2007).
Davies et al., "Affinity improvement of single antibody VH domains: residues in all three hypervariable regions affect antigen binding," Immunotechnology, 2(3):169-79 (Sep. 1996).
De Groot et al., "De-immunization of therapeutic proteins by T-cell epitope modification," Dev. Biol. (Basel), 122:171-94 (Jan. 2005).
De Pascalis et al., "Grafting of 'abbreviated' complementarity-determining regions containing specificity-determining residues essential for ligand contact to engineer a less immunogenic humanized monoclonal antibody," J. Immunol., 169(6):3076-84 (Sep. 2002).
Declaration of Nimish Gera, Ph.D., CV and Exhibits, dated Sep. 1, 2016, 24 pages.
Deen et al., "Structural determinants of glomerular permeability," Am. J. Physiol. Renal. Physiol., 281:F579-F596 (Oct. 2001).
Del Rio et al., "An Engineered Penicillin Acylase with Altered Surface Charge Is More Stable in Alkaline pH," Ann. NY Acad. Sci., 799:61-64 (Oct. 1996).
Deng et al., "An Agonist Murine Monoclonal Antibody to the Human c-Mpl Receptor Stimulates Megakaryocytopoiesis," Blood, 92:1981-88 (Sep. 1998).
Devanaboyina et al., "The effect of pH dependence of antibody-antigen interactions on subcellular trafficking dynamics," MAbs, 5(6):851-9 (Nov. 2013).
Dhiman et al., "Gene expression microarrays: a 21st century tool for directed vaccine design," Vaccine, Oct. 12, 2001;20(1-2):22-30.
Diaz et al., "Effects of engineering charged amino acids in the CH3 domains on antibody heavy chain dimerization," Philippine Science Letters. 2011;4(1):48-55.
Dillon et al., "Structural and functional characterization of disulfide isoforms of the human IgG2 subclass," J. Biol. Chem., 283(23):16206-15 (Jun. 2008).
Drake et al., "Chapter 5: Biophysical Considerations for Development of Antibody-Based Therapeutics," Biophysical Considerations for Development of Antibody-Based Therapeutics, Springer Springer Science & Business Media New York, 95-7 (2012).
Durkee et al., "Immunoaffinity chromatographic purification of Russell's viper venom factor X activator using elution in high concentrations of magnesium chloride," Protein Expr. Purif., Oct. 1993;4(5):405-11.
Ejima et al., "Effective elution of antibodies by arginine and arginine derivatives in affinity column chromatography," Analytical Biochem., Oct. 15, 2005;345(2):250-7.
Ejima et al., "Effects of Acid Exposure on the Conformation, Stability, and Aggregation of Monoclonal Antibodies," Proteins, Mar. 1, 2007;66(4):954-62.
Elliott et al., "Activation of the erythropoietin (EPO) receptor by bivalent anti-EPO receptor antibodies," J. Biol. Chem., 271(40):24691-7 (Oct. 1996).
Ewert et al., "Stability improvement of antibodies for extracellular and intracellular applications: CDR grafting to stable frameworks and structure-based framework engineering," Methods, 34:184-199 (Oct. 2004).
Feinberg et al., "Mechanism of pH-dependent N-acetylgalactosamine binding by a functional mimic of the hepatocyte asialoglycoprotein receptor," J. Biol. Chem., 275(45):35176-84 (Nov. 2000).
Fiedler et al., "An engineered IN-1 Fab fragment with improved affinity for the Nogo-A axonal growth inhibitor permits immunochemical detection and shows enhanced neutralizing activity," Protein Eng. Nov. 2002:15(11):931-41.
Finkelman et al., "Anti-cytokine antibodies as carrier proteins. Prolongation of in vivo effects of exogenous cytokines by injection of cytokine-anti-cytokine antibody complexes," J. Immunol., 151(3):1235-44 (Aug. 1993).
Foote et al., "Antibody framework residues affecting the conformation of the hypervariable loops," J. Mol. Biol., Mar. 20, 1992;224(2):487-99.
Fujii, "Antibody affinity maturation by random mutagenesis," Methods Mol. Biol., 248:345-59 (2004).

(56) References Cited

OTHER PUBLICATIONS

GE Healthcare. Application note 28-9277-92 AA. "High-throughput screening of elution pH for monoclonal antibodies on MabSelect SuRe using PreDictor plates" [online], [retrieved on Nov. 5, 2015]. Retrieved from the Internet: https://www.gelifesciences.com/gehcls_images/GELS/Related%20Content/Files/1314787424814/litdoc28927792AA_20110831131840.pdf.

Gen Bank Accession No. AAG00910.2, "recombinant IgG2 heavy chain, partial [*Homo sapiens*]," May 14, 2001, 1 page.

Gera et al., "Design of pH Sensitive Binding Proteins from the Hyperthermophilic Sso7d Scaffold," PLoS One, 2012;7(11):e48928. doi: 10.1371/journal.pone.0048928. Epub Nov. 7, 2012.

Gerstner et al., "Sequence plasticity in the antigen-binding site of a therapeutic anti-HER2 antibody," J. Mol. Biol., 321(5):851-62 (Aug. 2002).

Gessner et al., "The IgG Fc receptor family," Ann. Hematol., 76(6):231-248 (Jun. 1998).

Ghetie and Ward, "FcRn: the MHC class I-related receptor that is more than an IgG transporter," Immunol. Today, 18:592-598 (Dec. 1997).

Ghetie et al., "Increasing the serum persistence of an IgG fragment by random mutagenesis," Nat. Biotechnol., 15:637-640 (Jul. 1997).

Ghetie et al., "Multiple roles for the major histocompatibility complex class I-related receptor FcRn," Annu. Rev. Immunol., 18:739-766 (2000).

Glick et al., Molecular Biotechnology: Principles and Applications of Recombinant DNA, 3rd Edition, Chemical Industry Press, Mar. 2003, p. 168 (with English translation).

Gobburu et al., "Pharmacokinetics/dynamics of 5c8, a monoclonal antibody to CD154 (CD40 ligand) suppression of an immune response in monkeys," J. Pharmacol. Exp. Ther., 286:925-930 (Aug. 1998).

Goode et al., "The glomerular basement membrane charge-selectivity barrier: an oversimplified concept?" Nephrol. Dial. Transplant., 11:1714-16 (Sep. 1996).

Graves et al., "Molecular modeling and preclinical evaluation of the humanized NR-LU-13 antibody," Clin. Cancer Res., 5:899-908 (Apr. 1999).

Guerne et al., "Synovium as a source of interleukin 6 in vitro. Contribution to local and systemic manifestations of arthritis," J. Clin. Invest., 83(2):585-92 (Feb. 1989).

Gupta et al., "Affinity chromatography and co-chromatography of bispecific monoclonal antibody immunoconjugates," J. Biochem. Biophys. Methods, 51:203-216 (May 2002).

Guyre et al., "Increased potency of Fc-receptor-targeted antigens," Cancer Immunol. Immunother., 45(3-4):146-8 (Nov./Dec. 1997).

Hamers-Casterman et al., "Naturally occurring antibodies devoid of light chains," Nature, Jun. 3, 1993;363(6428):446-8.

Hanes et al., "Picomolar affinity antibodies from a fully synthetic naive library selected and evolved by ribosome display," Nat. Biotechnol., 18(12):1287-1292 (Dec. 2000).

Hanson et al., "Catalytic antibodies and their applications," Curr. Opin. Biotechnol., 16:631-636 (Dec. 2005).

He et al., "Humanization and pharmacokinetics of a monoclonal antibody with specificity for both E- and P-selectin," J. Immunol., 160:1029-35 (Jan. 1998).

Hinton et al., "An engineered human IgG1 antibody with longer serum half-life," J. Immunol., 176:346-356 (Jan. 2006).

Hinton et al., "Engineered human IgG antibodies with longer serum half-lives in primates," J.Biol Chem., Feb. 20, 2004;279(8):6213-6. Epub Dec. 29, 2003.

Hirano et al., "Excessive production of interleukin 6/B cell stimulatory factor-2 in rheumatoid arthritis," Eur. J. Immunol., 18(11):1797-801 (Nov. 1988).

Hirano et al., "Complementary DNA for a novel human interleukin (BSF-2) that induces B lymphocytes to produce immunoglobulin," Nature, 324: 73-76 (Nov. 1986).

Hirata et al., "Characterization of IL-6 Receptor Expression by Monoclonal and Polyclonal Antibodies," J. lmmunol. Nov. 1, 1989;143(9):2900-6.

Hird et al., "Tumour localisation with a radioactively labelled reshaped human monoclonal antibody," Br. J. Cancer, Nov. 1991;64(5):911-4.

Hironiwa et al., "Calcium-dependent antigen binding as a novel modality for antibody recycling by endosomal antigen dissociation," MAbs. Jan. 2016;8(1):65-73. doi: 10.1080/19420862.2015. 1110660. Epub Oct. 23, 2015.

Hong et al., "Enhanced cellular uptake and transport of polyclonal immunoglobulin G and fab after their cationization," J. Drug Target., 2000;8(2):67-77.

Holt et al., "Domain antibodies: proteins for therapy," Trends Biotechnol., 21(11):484-90 (Nov. 2003).

Hoogenboom, "Selecting and screening recombinant antibody libraries," Nat. Biotechnol., Sep. 2005; 23(9):1105-16.

Hosokawa et al., "The Response to Treatment with Interferon beta-lb in Patients with Multiple Sclerosis," Shinkei Chiryo, 2008;25:589-95 (with English translation).

Houssiau et al., "Interleukin-6 in synovial fluid and serum of patients with rheumatoid arthritis and other inflammatory arthritides," Arthritis Rheum., 31(6):784-8 (Jun. 1988).

Houzen et al., "Increased prevalence, incidence, and female predominance of multiple sclerosis in northern Japan," J. Neurol. Sci., Dec. 15, 2012;323(1-2):117-22.

Huang et al., "A Monoclonal Anti-Human IL-6 Receptor Antibody Inhibits the Proliferation of Human Myeloma Cells," Hybridoma. Oct. 1993:12(5):621-30.

Hwang et al., "Use of human germline genes in a CDR homology based approach to antibody humanization," Methods, 36:35-42 (May 2005).

Igawa et al., "Antibody optimization technologies for developing next generation antibody therapeutics," Bio. Industry, 28(7):15-21 (2011) (with English translation).

Igawa et al., "Antibody recycling by engineered pH-dependent antigen binding improves the duration of antigen neutralization," Nat. Biotechnol., Nov. 2010;28(11):1203-7. doi: 10.1038/nbt.1691. Epub Oct. 17, 2010.

Igawa et al., "Engineered monoclonal antibody with novel antigen-sweeping activity in vivo," PLoS One, 8(5):e63236 (May 2013).

Igawa et al., "Engineering the variable region of therapeutic IgG antibodies," MAbs, 3(3):243-52 (May-Jun. 2011).

Igawa et al., "Reduced elimination of IgG antibodies by engineering the variable region," Protein Eng. Des. Sel., 23(5):385-92 (May 2010).

Ishihara et al., "Accelerated purification process development of monoclonal antibodies for shortening time to clinic. Design and case study of chromatography processes," J. Chromatogr. A, 1176(1-2):149-56 (Dec. 2007).

Ishii et al., "FcRn, a critical regulator of antibody pharmacokinetics," Folia Pharmacol. Jpn., 136(5):280-284 (Nov. 2010) (with English translation).

Ito et al., "The His-probe method: effects of histidine residues introduced into the complementarity-determining regions of antibodies on antigen-antibody interactions at different pH values," FEBS Lett., 309:85-88 (Aug. 1992).

Janeway et al., Immunobiology, 5th edition. Jun. 2001: Extract from Chapter 3, pp. 93-122.

Janeway et al., Immunobiology, 5th edition. Jun. 2001: Extract from Chapter 4, pp. 123-154.

Japanese Society of Neurological Therapeutices, "Standard Neurological Therapeutics: Neuromyelitis Optica (NMO)", Nov. 2013, vol. 30, No. 6, p. 777-794, with partial English translation.

Johnson et al., "Cation exchange-HPLC and mass spectrometry reveal C-terminal amidation of an IgG1 heavy chain," Analytical Biochem., 360:75-83 (Jan. 2007).

Jones et al., "Identification and removal of a promiscuous CD4+ T cell epitope from the C1 domain of factor VIII," Thromb. Haemost., 3:991-1000 (May 2005).

Junghans et al., "The protection receptor for IgG catabolism is the beta2-microglobulin-containing neonatal intestinal transport receptor," Proc. Natl. Acad. Sci. U S A., May 28, 1996;93(11):5512-6.

Kabat et al., "Sequences of Proteins of Immunological Interest," National Institute of Health, Publ'n No. 91-3242, vol. 1 p. 647-660 (5th ed. 1991).

(56) References Cited

OTHER PUBLICATIONS

Kai et al., "Switching constant domains enhances agonist activities of antibodies to a thrombopoietin receptor," Nat. Biotechnol., 26(2):209-11 (Feb. 2008).
Kakuron III, "Section 9 Opticospinal Multiple Sclerosis," Tahatsusei Kokasho Chiryo Guideline, 2010;2010:104-9 (with English translation).
Kashmiri et al., "Generation, characterization, and in vivo studies of humanized anticarcinoma antibody CC49," Hybridoma, 14:461-473 (Oct. 1995).
Katayose et al., "MUC1-specific targeting immunotherapy with bispecific antibodies: inhibition of xenografted human bile duct carcinoma growth," Cancer Res., 56(18):4205-12 (Sep. 1996).
Khawli et al., "Improved tumor localization and radioimaging with chemically modified monoclonal antibodies," Cancer Biother. Radiopharm., 11:203-215 (Jun. 1996).
Kim et al., "Antibody engineering for the development of therapeutic antibodies," Mol. Cells, 20:17-29 (Aug. 2005).
Kim et al., "Chemical modification to reduce renal uptake of disulfide-bonded variable region fragment of anti-tac monoclonal antibody labeled with 99mTc," Bioconjugate Chem., 10:447-453 (Mar. 1999).
Kim et al., "Lowering of pI by acylation improves the renal uptake of 99mTc-labeled anti-Tac dsFv: effect of different acylating reagents," Nucl. Med. Biol., 29:795-801 (Nov. 2002).
Kishimoto, "The biology of interleukin-6," Blood, 74(1):1-10 (Jul. 1989).
Knappik et al., "Fully Synthetic Human Combinatorial Antibody Libraries (HuCAL) Based on Modular Consensus Frameworks and CDRs Randomized with Trinucleotides," J. Mol. Biol., Feb. 11, 2000;296(1):57-86.
Kobayashi et al., "A monoclonal antibody specific for a distinct region of hen egg-white lysozyme," Mol. Immunol., 19:619-30 (Apr. 1982).
Kobayashi et al., "The pharmacokinetic characteristics of glycolated humanized anti-Tac Fabs are determined by their isoelectric points," Cancer Res., 59:422-430 (Jan. 1999).
Komissarov et al., "Site-specific mutagenesis of a recombinant anti-single-stranded DNA Fab. Role of heavy chain complementarity-determining region 3 residues in antigen interaction," J. Biol. Chem., 272(43):26864-70 (Oct. 1997).
Kotake et al., "Interleukin-6 and soluble interleukin-6 receptors in the synovial fluids from rheumatoid arthritis patients are responsible for osteoclast-like cell formation," J. Bone Miner. Res., 11(1):88-95 (Jan. 1996).
Kreutz et al., "Efficient bispecific monoclonal antibody purification using gradient thiophilic affinity chromatography," J. Chromatogr. B, 714:161-170 (Sep. 1998).
Krieckaert et al., "Immunogenicity of biologic therapies—we need tolerance," Nat. Rev. Rheumatol. Oct. 2010; 6(10):558-9. doi:10.1038/nrrheum. 2010.
Kuroda et al., "Computer-aided antibody design," Protein Eng. Des. Sel., Oct. 2012;25(10):507-21. Epub Jun. 2, 2012.
Laitinen et al., "Brave new (strept)avidins in biotechnology," Trends Biotechnol., Jun. 2007;25(6):269-77. Epub Apr. 12, 2007.
Lee et al., "High-affinity human antibodies from phage-displayed synthetic Fab libraries with a single framework scaffold," J. Mol. Biol., 340(5):1073-93 (Jul. 2004).
Leong et al., "Adapting pharmacokinetic properties of a humanized anti-interleukin-8 antibody for therapeutic applications using site-specific pegylation," Cytokine, 16(3):106-19 (Nov. 2001).
Li et al., "Construction and characterization of a humanized anti-human CD3 monoclonal antibody 12F6 with effective immunoregulation functions," Immunology, Dec. 2005;116(4):487-98.
Lin et al., "Preclinical pharmacokinetics, interspecies scaling, and tissue distribution of a humanized monoclonal antibody against vascular endothelial growth factor," J. Pharmacol. Exp. Ther., 288(1):371-8 (Jan. 1999).
Linder et al., "Design of a pH-dependent cellulose-binding domain," FEBS Lett., Mar. 19, 1991;447(1):13-6.

Lindhofer et al., "Preferential Species-Restricted Heavy/Light Chain Pairing in Rat/Mouse Quadromas," J. Immunol., 155:219-225 (Jul. 1995).
Liu et al., "Heterogeneity of monoclonal antibodies," J. Pharm. Sci., 97(7):2426-47 (Jul. 2008).
Lobo et al., "Antibody pharmacokinetics and pharmacodynamics," J. Pharm. Sci., 93:2645-68 (Aug. 2004).
Lotz et al., "B Cell Stimulating Factor 2/Interleukin 6 is a Costimulant for Human Thymocytes and T Lymphocytes," J. Exp. Med., Mar. 1, 1988; 167(3): 1253-1258.
Lucchinetti et al., "Heterogeneity of multiple sclerosis lesions: implications for the pathogenesis of demyelination," Ann. Neurol., Jun. 2000;47:707-17.
Lund et al., "Expression and characterization of truncated forms of humanized L243 IgG1. Architectural features can influence synthesis of its oligosaccharide chains and affect superoxide production triggered through human Fcgamma receptor I," Eur. J. Biochem., 267:7246-57 (Dec. 2000).
MacCallum et al., "Antibody-antigen interactions: contact analysis and binding site topography," J. Mol. Biol., 262:732-45 (Oct. 1996).
Madhok et al., "Serum interleukin 6 levels in rheumatoid arthritis: correlations with clinical and laboratory indices of disease activity," Ann. Rheum. Dis., 52(3):232-4 (Mar. 1993).
Maeda et al., "pH-dependent receptor/ligand dissociation as a determining factor for intracellular sorting of ligands for epidermal growth factor receptors in rat hepatocytes," J. Control. Release, 82(1):71-82 (Jul. 2002).
Maier et al., "Assessment of fully automated antibody homology modeling protocols in molecular operating environment," Proteins. Aug. 2014;82(8):1599-610. doi: 10.1002/prot.24576. Epub Apr. 23, 2014.
Maini et al., "Double-blind randomized controlled clinical trial of the interleukin-6 receptor antagonist, tocilizumab, in European patients with rheumatoid arthritis who had an incomplete response to methotrexate," Arthritis Rheum., 54:2817-29 (Aug. 2006).
Manzke et al., "Single-step purification of bispecific monoclonal antibodies for immunotherapeutic use by hydrophobic interaction chromatography," J. Immunol. Methods, 208:65-73 (Oct. 1997).
Marshall et al., "Rational design and engineering of therapeutic proteins," Drug Discov. Today., Mar. 1, 2003;8(5):212-21.
Martin et al., "Crystal structure at 2.8 A of an FcRn/heterodimeric Fc complex: mechanism of pH-dependent binding," Mol. Cell, 7:867-877 (Apr. 2001).
Martinez et al., "Disulfide connectivity of human immunoglobulin G2 structural isoforms," Biochemistry, 47(28):7496-7508 (Jun. 2008).
Marvin et al., "Recombinant approaches to IgG-like bispecific antibodies," Acta. Pharmacol. Sin., 26:649-658 (Jun. 2005).
Marvin et al., "Redesigning an antibody fragment for faster association with its antigen," Biochemistry, 42:7077-83 (May 2003).
Maxfield et al., "Endocytic recycling," Nat. Rev. Mol. Cell Biol., 5(2):121-32 (Feb. 2004).
Maynard et al., "Antibody engineering," Annu. Rev. Biomed. Eng., 2:339-76 (2000).
Merchant et al., "An efficient route to human bispecific IgG," Nat. Biotechnol., 16:677-681 (Jul. 1998).
Mihara et al., "Tocilizumab inhibits signal transduction mediated by both mIL-6R and sIL-6R, but not by the receptors of other members of IL-6 cytokine family," Int. Immunopharmacol., 5(12):1731-40 (Nov. 2005).
Miller et al., "Differential diagnosis of suspected multiple sclerosis: a consensus approach," Mulpitle Scler., Nov. 2008;14(9):1157-74.
Montero-Julian et al., "Pharmacokinetic study of anti-interleukin-6 (IL-6) therapy with monoclonal antibodies: enhancement of IL-6 clearance by cocktails of anti-IL-6 antibodies," Blood, Feb. 15, 1995;85(4):917-24.
Muller et al., "VEGF and the Fab fragment of a humanized neutralizing antibody: crystal structure of the complex at 2.4 Å resolution and mutational analysis of the interface," Structure, Sep. 6, 1998;(9):1153-67.
Murata et al., "Anti-Digoxin Fab Variants Generated by Phage Display," Mol. Biotechnol. Jun. 2013: 54(2):269-77. doi:10.1007/s12033-012-9564-1.

(56) References Cited

OTHER PUBLICATIONS

Murtaugh et al., "A combinatorial histidine scanning library approach to engineer highly pH-dependent protein switches," Protein Sci., 20(9):1619-31 doi:10.1002/pro 696 (Aug. 2011).
Nakamura et al., "Clinical Characteristics of Multiple Sclerosis with High Peripheral Blood Plasmablast Frequency," Meeting Abstract, 54th Annual Meeting of the Japanese Society of Neurology, Tokyo, Japan, published Apr. 30, 2013 (with English translation).
Nakamura et al., "Clinical Features of Multiple Sclerosis with High Plasmablast Frequency in Peripheral Blood," Abstract for Poster Session, Multiple Sclerosis, Keystone Symposia on Molecule and Cellular Biology, Big Sky, Montana, distributed Jan. 11, 2013.
Nakamura et al., "Clinical Features of Multiple Sclerosis with High Plasmablast Frequency in Peripheral Blood," Abstract, Multiple Sclerosis, Keystone Symposia on Molecule and Cellular Biology, Big Sky, Montana, published online Dec. 11, 2012.
Nakamura et al., "Clinical Features of Multiple Sclerosis with High Plasmablast Frequency in Peripheral Blood," Poster Session, 54th Annual Meeting of the Japanese Society of Neurology, Tokyo, Japan, presented Jun. 1, 2013 (with English translation).
Nakamura et al., "Clinical Features of Multiple Sclerosis with High Plasmablast Frequency in Peripheral Blood," Poster Session, Multiple Sclerosis, Keystone Symposia on Molecular and Cellular Biology, Big Sky, Montana, presented Jan. 14, 2013.
Nakamura, et al., "Plasmablast in the pathology of multiple sclerosis," Jpn. J. Clin. Immunol., Jan. 2015;38(5):403-11. doi: 10.2177/jsci.38.403 (English abstract).
Nakamura et al., "IL-6-dependent Plasmablasts in Pathological Conditions of Relapsing-Remitting Multiple Sclerosis," Jap. J. Clin. Immunol., 2013;36:345, W5-5 (with English translation).
Nesterova et al., "Glypican-3 as a novel target for an antibody-drug conjugate," AACR Abstract No. 656, Los Angeles, CA (Apr. 4-18, 2007).
Newman et al, "Modification of the Fc Region of a Primatized IgG Antibody to Human CD4 Retains Its Ability to Modulate CD4 Receptors but Does Not Deplete CD4 T Cells in Chimpanzees," Clin. Immunol. Feb. 2001;98(2):164-74.
Nishimoto et al., "Anti-interleukin 6 receptor antibody treatment in rheumatic disease," Ann. Rheum. Dis., 59 Suppl 1:i21-7 (Nov. 2000).
Nishimoto et al., "Clinical studies in patients with Castleman's disease, Crohn's disease, and rheumatoid arthritis in Japan," Clin. Rev. Allergy Immunol., 28(3):221-30 (Jun. 2005).
Nishimoto et al., "Humanized antihuman IL-6 receptor antibody, tocilizumab," Handb. Exp. Pharmacol., (181):151-60 (2008).
Nishimoto et al., "Humanized anti-interleukin-6 receptor antibody treatment of multicentric Castleman disease," Blood, 106:2627-32 (Oct. 2005).
Nishimoto et al., "Interleukin 6: from bench to bedside," Nat. Clin. Pract. Rheumatol., 2(11):619-26 (Nov. 2006).
Nishimoto, "Humanized anti-IL-6 Receptor Antibody (Tocilizumab)," Nihon Rinsho, 65(7):1218-26 (2007) (with English translation).
Nordlund et al., "Introduction of histidine residues into avidin subunit interfaces allows pH-dependent regulation of quaternary structure and biotin binding," FEBS Lett., Dec. 18, 2003;555(3):449-54.
Novick et al., "Monoclonal Antibodies to the Soluble Human IL-6 Receptor: Affinity Purification, ELISA, and Inhibition of Ligand Binding," Hybridoma. Feb. 1991;10(1) :137-46.
Ober et al., "Visualizing the Site and Dynamics of IgG Salvage by the MHC Class I-Related Receptor, FcRn," J. Immunol. Feb. 15, 2004;172(4):2021-9.
Ohno et al., "Antigen-binding specificities of antibodies are primarily determined by seven residues of VH," Proc. Natl. Acad. Sci. U.S.A., 82(9):2945-9 (May 1985).
Ohsugi et al., "Success Story of Pre-market Approved Pipeline," Pharm. Stage, 7(5):13-18 (2007)(English translation included).
Okabe, "Proprietary Innovative Antibody Engineering Technologies in Chugai Pharmaceutical," Dec. 18, 2012, 78 pages.
Onda et al., "Lowering the Isoelectric Point of the Fv Portion of Recombinant Immunotoxins Leads to Decreased Nonspecific Animal Toxicity without Affecting Antitumor Activity," Cancer Res., 61:5070-77 (Jul. 2001).
Ono et al., "The humanized anti-HM1.24 antibody effectively kills multiple myeloma cells by human effector cell-mediated cytotoxicity," Mol. Immunol., 36(6):387-95 (Apr. 1999).
Osbourn et al., "Generation of a panel of related human scFv antibodies with high affinities for human CEA," Immunotechnology, Sep. 1996:2(3):181-96.
Ozhegov et al., Tolkovyi Slovar Russkogo iazyka: 2004, p. 292 (with an English translation of the relevant passage defining "control").
Padlan et al., "Structure of an antibody-antigen complex: crystal structure of the HyHEL-10 Fab-lysozyme complex," Proc. Natl. Acad. Sci. USA, 86:5938-5942 (Aug. 1989).
Pakula et al., "Genetic Analysis of Protein Stability and Function," Ann. Rev. Genet., 23:289-310 (Jan. 1989).
Palladino et al., "Anti-TNF-alpha therapies: the next generation," Nat. Rev. Drug Discov., Sep. 2003;2(9):736-46.
Pancook et al., "In Vitro Affinity Maturation of Human IgM Antibodies Reactive with Tumor-Associated Antigens," Hybrid. Hybridomics. Oct. 2001:20(5-6):383-96.
Pardridge et al., "Enhanced endocytosis in cultured human breast carcinoma cells and in vivo biodistribution in rats of a humanized monoclonal antibody after cationization of the protein,"J. Pharmacol. Exp. Ther., 286(1):548-54 (Jul. 1998).
Pardridge et al., "Enhanced cellular uptake and in vivo biodistribution of a monoclonal antibody following cationization," J. Pharm. Sci., Aug. 1995;84(8):943-8.
Pavlinkova et al., "Charge-modified single chain antibody constructs of monoclonal antibody CC49: Generation, characterization, pharmacokinetics, and biodistribution analysis," Nucl. Med. Biol., 26:27-34 (Jan. 1999).
Pavlou et al., "The therapeutic antibodies market to 2008," Eur. J. Pharm. Biopharm., 59:389-396 (Apr. 2005).
Pejchal et al., "A Conformational Switch in Human Immunodeficiency Virus gp41 Revealed by the Structures of Overlapping Epitopes Recognized by Neutralizing Antibodies," J. Virol. Sep. 2009; 83 (17):8451-62. doi:10.1128/JVI.00685-09. Epub Jun. 10, 2009.
Philippovich, "Fundamentals of Biochemistry," edition Higher School, Moscow, p. 31 (1969).
Pini et al., "Design and use of a phage display library Human antibodies with subnanomolar affinity against a marker of angiogenesis eluted from a two-dimensional gel," J. Biol. Chem., 273(34):21769-76 (Aug. 1998).
Poduslo et al., "Polyamine modification increases the permeability of proteins at the blood—nerve and blood brain barriers," J. Neurochem., 66:1599-1609 (Apr. 1996).
Pokrovsky, vol. 1 A-Infant, Soviet Encyclopedia, p. 146 (1991) (with English translation).
Polman et al., "Diagnostic Criteria for Multiple Sclerosis: 2010 Revisions to the McDonald Criteria," Ann. Neurol., Feb. 2011;69(2):292-302. doi: 10.1002/ana.22366.
Pons et al., "Energetic analysis of an antigen/antibody interface: alanine scanning mutagenesis and double mutant cycles on the HyHEL-10/lysozyme interaction," Protein Sci., 8(5):958-68 (May 1999).
Presta et al., "Molecular engineering and design of therapeutic antibodies," Curr. Opin. Immunol., 20(4):460-70. doi: 10.1016/j.coi.2008.06.012 (Aug. 2008).
Presta, "Engineering of therapeutic antibodies to minimize immunogenicity and optimize function," Adv. Drug Deliv. Rev., 58(5-6):640-56 (Aug. 2006).
Rajpal et al., "A general method for greatly improving the affinity of antibodies by using combinatorial libraries," Proc. Natl. Acad. Sci. USA, 102:8466-71 (Jun. 2005).
Raposo et al., "Epitope-specific anitbody response is controlled by immunoglobulin Vh polymorphisms," J. Exp. Med. Mar. 10, 2014:211 (3):405-11. doi:10.1084/jem.20130968. Epub Feb. 17, 2014.

(56) References Cited

OTHER PUBLICATIONS

Rathanaswami et al., "Demonstration of an in vivo generated sub-picomolar affinity fully human monoclonal antibody to interleukin-8," Biochem. Biophys. Res. Commun., 334:1004-13.(Sep. 2005).
Reddy et al., "Elimination of Fc receptor-dependent effector functions of a modified IgG4 monoclonal antibody to human CD4," J. Immunol., 164(4):1925-33 (Feb. 2000).
Reichert et al., "Development trends for monoclonal antibody cancer therapeutics," Nat. Rev. Drug Discov., 6(5):349-56 (May 2007).
Reichert et al., "Monoclonal antibody successes in the clinic," Nat. Biotechnol., 23:1073-78 (Sep. 2005).
Reichert, "Antibodies to watch in 2014," mAbs, 6(4): 799-802 (Jul./Aug. 2014).
Reimann et al., "A humanized form of a CD4-specific monoclonal antibody exhibits decreased antigenicity and prolonged plasma half-life in rhesus monkeys while retaining its unique biological and antiviral properties," AIDS Res Hum Retroviruses, Jul. 20, 1997;13(11):933-43.
Reist et al., "Human IgG2 constant region enhances in vivo stability of anti-tenascin antibody 81C6 compared with its murine parent," Clin Cancer Res., Oct. 1998;4(10):2495-502.
Rich et al., "Grading the commercial optical biosensor literature—Class of 2008: 'The Mighty Binders'," J. Mol. Recognit., 23(1):1-64 (Jan./Feb. 2010). doi: 10.1002/jmr.1004.
Roitt et al., Immunology, M. Mir, p. 110 (2000) (with English translation).
Roitt et al., Immunology, M., Mir, (2000), pp. 110-111 (in Russian, with what is believed to be a published English equivalent of those pages taken from Roitt et al., "Antibody Structure and Function," Immunology, Fifth Ed., (1998), pp. 80-81).
Rojas et al., "Formation, distribution, and elimination of infliximab and anti-infliximab immune complexes in cynomolgus monkeys," J. Pharmacol. Exp. Ther., May 2005;313(2):578-85. Epub Jan. 12, 2005.
Roopenian et al., "FcRn: the neonatal Fc receptor comes of age," Nat. Rev. Immunol., Sep. 2007;7(9):715-25. Epub Aug. 17, 2007.
Rothe et al., "Ribosome display for improved biotherapeutic molecules," Expert. Opin. Biol. Ther., 6:177-187 (Feb. 2006).
Rudikoff et al., "Single amino acid substitution altering antigen-binding specificity," Proc. Natl. Acad. Sci. U.S.A., 79(6):1979-83 (Mar. 1982).
Sack et al., "Interleukin-6 in synovial fluid is closely associated with chronic synovitis in rheumatoid arthritis," Rheumatol. Int., 13(2):45-51 (Jun. 1993).
Salfeld et al., "Isotype selection in antibody engineering," Nat. Biotechnol., 25:1369-72 (Dec. 2007).
Sal-Man et al., "Arginine mutations within a transmembrane domain of Tar, an *Escherichia coli* aspartate receptor, can drive homodimer dissociation and heterodimer association in vivo," Biochem. J., 385:29-36 (Jan. 2005).
Sarkar et al., "Rational cytokine design for increased lifetime and enhanced potency using pH-activated 'histidine switching'," Nat. Biotechnol., Sep. 2002;20(9):908-13. Epub Aug. 5, 2002.
Sato et al., "Reshaping a human antibody to inhibit the interleukin 6-dependent tumor cell growth," Cancer Res., 53:851-856 (Feb. 1993).
Schaeffer et al., "The Rat Glomerular Filtration Barrier Does Not Show Negative Charge Selectivity," Microcirculation, 9:329-342 (Oct. 2002).
Schier et al., "Isolation of Picomolar Affinity Anti-c-erbB-2 Single-chain Fv by Molecular Evolution of the Complementarity Determining Regions in the Center of the Antibody Binding Site," J. Mol. Biol. Nov. 8, 1996:263(4):551-67.
Schmitz et al., "Phage display: a molecular tool for the generation of antibodies—a review," Placenta., 21 Suppl A:S106-12 (Mar.-Apr. 2000).
Schroeder et al., "Similarity and divergence in the development and expression of the mouse and human antibody repertoires," Dev. Comp. Immunol., Jan. 2006;30(1-2):119-35.
Schroter et al., "A generic approach to engineer antibody pH-switches using combinatorial histidine scanning libraries and yeast display," MAbs., Jan.-Feb. 2015;7(1):138-51. doi: 10.4161/19420862.2014.985993.
Sebba et al., "Tocilizumab: the first interleukin-6-receptor inhibitor," Am. J. Health Syst. Pharm., Aug. 1, 2008;65(15):1413-8. doi: 10.2146/ajhp070449.
Segal et al., "Bispecific antibodies in cancer therapy," Curr. Opin. Immunol., 11:558-562 (Oct. 1999).
Sharifi et al., "Improving monoclonal antibody pharmacokinetics via chemical modification," Quarterly J. Nucl. Med., Dec. 1998;42(4):242-9.
Shaul, "Exploring the charge space of protein-protein association: a proteomic study," Proteins, 60:341-352 (Aug. 2005).
Shields et al., "High resolution mapping of the binding site on human IgG1 for Fc gamma RI, Fc gamma RII, Fc gamma RIII, and FcRn and design of IgG1 variants with improved binding to the Fc gamma R," J. Biol. Chem., 276:6591-6604 (2001) (Epub Nov. 28, 2000).
Shimizu et al., "IFNβ-1b may severely exacerbate Japanese optic-spinal MS in neuromyelitis optica spectrum," Neurology, Oct. 19, 2010;75(16):1423-7.
Shire et al., "Challenges in the development of high protein concentration formulations," J. Pharm. Sci., 93:1390-1402 (Jun. 2004).
Sigma-Aldrich, "Product Information: Monoclonal Anti-Flag ® M1, Clone M1 produced in mouse, purified immunoglobulin," Sigma-Aldrich.com, Catalog No. F3040. Retrieved from the Internet on Nov. 5, 2013 at: http://www.sigmaaldrich.com/content/dam/sigma-aldrich/docs/Sigma/Datasheet/f3040dat.pdf.
Singer et al., Genes & Genomes, 1991;67-69.
Smolen et al., "Interleukin-6: a new therapeutic target," Arthritis Res. Ther., Jul. 2006;8 Suppl 2:S5. Epub Jul. 28, 2006.
Smith et al., "The challenges of genome sequence annotation or 'The devil is in the details'," Nature Biotechnology, Nov. 1997;15:1222-1223.
Spiess et al., "Bispecific antibodies with natural architecture produced by co-culture of bacteria expressing two distinct half-antibodies," Nat. Biotechnol. Aug. 1, 2013;31(8):753-8. doi: 10.1038/nbt.2621. Epub Jul. 7, 2013.
Srivastava et al., "Potassium channel KIR4.1 as an immune target in multiple sclerosis," New Engl. J. Med., Jul. 12, 2012;367:115-23.
Stearns et al., "The interaction of a Ca2+-dependent monoclonal antibody with the protein C activation peptide region. Evidence for obligatory Ca2+ binding to both antigen and antibody," J. Biol. Chem., Jan. 15, 1988;263(2):826-32.
Stewart et al., "Site-directed mutagenesis of a catalytic antibody: an arginine and a histidine residue play key roles," Biochemistry, 33(8):1994-2003 (Mar. 1994).
Strand et al., "Biologic therapies in rheumatology: lessons learned, future directions," Nat. Rev. Drug Discov., 6:75-92 (Jan. 2007).
Sun et al., "Coexpression of Gas6/Axl in human ovarian cancers," Oncology, 66(6):450-7 (Jan. 2004).
Tabrizi et al., "Elimination mechanisms of therapeutic monoclonal antibodies," Drug Discov. Today, Jan. 2006;11(1-2):81-8.
Taga et al., "Receptors for B Cell Stimulatory Factor 2," J. Exp. Med. Oct. 1, 1987; 166(4): 967-981.
Taga et al., "Interleukin-6 Triggers the Association of Its Receptor with a Possible Signal Transducer, gp130," Cell, Aug. 11, 1989; 58(3): 873-581.
Takkinen et al., "Affinity and Specificity Maturation by CDR Walking," Antibody Engineering, Springer Lab Manuals, pp. 540-545 (2001).
Tamura et al., "Soluble interleukin-6 receptor triggers osteoclast formation by interleukin 6," Proc. Natl. Acad. Sci. USA, 90(24):11924-8 (Dec. 1993).
Tan et al., "Engineering the isoelectric point of a renal cell carcinoma targeting antibody greatly enhances scFv solubility," Immunotechnology, 4(2):107-114 (Oct. 1998).
Tarditi et al., "Selective high-performance liquid chromatographic purification of bispecific monoclonal antibodies," J. Chromatogr., 599:13-20 (May 1992).

(56) References Cited

OTHER PUBLICATIONS

Teeling et al., "The biological activity of human CD20 monoclonal antibodies is linked to unique epitopes on CD20," J. Immunol., 177(1):362-71 (Jul. 2006).
Ten Kate et al., "Effect of isoelectric point on biodistribution and inflammation: imaging with indium-111-labelled IgG," Eur. J. Nucl. Med., 17:305-309 (Jan. 1990).
Thies et al., "The alternatively folded state of the antibody C(H)3 domain," J Mol. Biol., Jun. 22, 2001;309(5):1077-85.
Tintoré et al., "Isolated demyelinating syndromes: comparison of different MR imaging criteria to predict conversion to clinically definite multiple sclerosis," AJNR Am. J. Neuroradiol., Apr. 2000;21(4):702-6.
Tsubaki et al., "C-terminal modification of monoclonal antibody drugs: amidated species as a general product-related substance," Int. J. Biol. Macromol., 52:139-47. doi: 10.1016/j.ijbiomac.2012.09. 016. Epub Sep. 25, 2012.
Tsuchiya, Credit Suisse Seminar, "Therapeutic Antibody," at Fuji-Gotemba Laboratories, p. 21 (2006), with English translation.
Tsurushita et al., "Design of humanized antibodies: From anti-Tac to Zenapax," Methods,36:69-83 (May 2005).
Vaisitti et al., "Cationization of monoclonal antibodies: another step towards the 'magic bullet'?," J. Biol. Regul. Homeost. Agents, 19(3-4):105-12 (Jul.-Dec. 2005).
Vajdos et al., "Comprehensive functional maps of the antigen-binding site of an anti-ErbB2 antibody obtained with shotgun scanning mutagenesis," J. Mol. Biol., 320(2):415-28 (Jul. 2002).
Van Walle et al., "Immunogenicity screening in protein drug development," Expert. Opin. Biol. Ther., 7(3):405-418 (Mar. 2007).
Vaughn et al., "Structural basis of pH-dependent antibody binding by the neonatal Fc receptor," Structure, 6(1):63-73 (Jan. 1998).
Verhoeyen et al., "Construction of a reshaped HMFG1 antibody and comparison of its fine specificity with that of the parent mouse antibody," Immunology, Mar. 1993;78(3):364-70.
Verhoeyen et al., "Monoclonal Antibodies in Clinical Oncology," 1991, Edited by AA Epenetos, Chapter 5, pp. 37-43, Chapman and Hall.
Wally et al., "Identification of a novel substitution in the constant region of a gene coding for an amyloidogenic kappal light chain," Biochim Biophys Acta., May 31, 1999;1454(1):49-56.
Wang et al., "Antibody structure, instability, and formulation," J. Pharm. Sci., Jan. 2007;96(1):1-26.
Wang et al., "Polyethylene Glycol-modified Chimeric Toxin Composed of Transforming Growth Factor alpha and Pseudomonas Exotoxin," Cancer Res., 53:4588-4594 (Oct. 1993).
Ward et al., "A calcium-binding monoclonal antibody that recognizes a non-calcium-binding epitope in the short consensus repeat units (SCRs) of complement C1r," Mol. Immunol., Jan. 1992;29(1):83-93.
Waubant et al., "Clinical characteristics of responders to interferon therapy for relapsing MS," Neurology, Jul. 22, 2003;61(2):184-9.
Wiens et al., "Mutation of a single conserved residue in VH complementarity-determining region 2 results in a severe Ig secretion defect," J. Immunol., 167(4):2179-86 (Aug. 2001).
Wiens et al., "Somatic mutation in VH complementarity-determining region 2 and framework region 2: differential effects on antigen binding and Ig secretion," J. Immunol., 159(3):1293-302 (Aug. 1997).
Wikipedia, "Chaotropic agent" [online], [retrieved on Nov. 2, 2015]. Retrieved from the Internet: https://en.wikipedia.org/wiki/Chaotropic_agent.
Wingerchuk et al., "Revised diagnostic criteria for neuromyelitis optica," Neurology, May 23, 2006;66(10):1485-9.
Wingerchuk et al., "International consensus diagnostic criteria for neuromyelitis optica spectrum disorders," Neurology, Jul. 14, 2015;85(2):177-89. doi: 10.1212/WNL.0000000000001729. Epub Jun. 19, 2015.
Wojciak et al., "The crystal structure of sphingosine-1-phosphate in complex with a Fab fragment reveals metal bridging of an antibody and its antigen," Proc. Natl. Acad. Sci. U.S.A., 106(42):17717-22 (Oct. 2009).
Wu et al., "Development of motavizumab, an ultra-potent antibody for the prevention of respiratory syncytial virus infection in the upper and lower respiratory tract," J. Mol. Biol., 368:652-665 (May 2007).
Wu et al., "Humanization of a murine monoclonal antibody by simultaneous optimization of framework and CDR residues," J. Mol. Biol., 294(1):151-62 (Nov. 1999).
Wu et al., "Stepwise in vitro affinity maturation of Vitaxin, an αvβ33-specific humanized mAb," Proc. Natl. Acad. Sci. USA. May 26, 1998 ; 95(11):6037-42.
Wypych et al., "Human IgG2 antibodies display disulfide-mediated structural isoforms," J. Biol. Chem., 283(23):16194-16205 (Jun. 2008).
Xiang et al., "Study of B72.3 combining sites by molecular modeling and site-directed mutagenesis," Protein Eng., 13(5):339-44 (May 2000).
Yamamoto et al., "Molecular studies of pH-dependent ligand interactions with the low-density lipoprotein receptor," Biochemistry, 47(44):11647-52 (Nov. 2008).
Yamasaki et al., "Pharmacokinetic analysis of in vivo disposition of succinylated proteins targeted to liver nonparenchymal cells via scavenger receptors: importance of molecular size and negative charge density for in vivo recognition by receptors," J. Pharmacol. Exp. Ther., 301:467-477 (May 2002).
Yamasaki et al., "Cloning and Expression of the Human Interleukin-6 (BSF-2/IFNβ 2) Receptor," Science. Aug. 12, 1988:241 (4867):825-8.
Yang et al., "CDR walking mutagenesis for the affinity maturation of a potent human anti-HIV-1 antibody into the picomolar range," J. Mol. Biol., 254(3):392-403 (Dec. 1995).
Yang et al., "Tailoring structure-function and pharmacokinetic properties of single-chain Fv proteins by site-specific PEGylation," Protein Eng., 16:761-770 (Oct. 2003).
Yeung et al., "Engineering human IgG1 affinity to human neonatal Fc receptor: impact of affinity improvement on pharmacokinetics in primates," J. Immunol., Jun. 15, 2009;182(12):7663-71. doi: 10.4049/jimmunol.0804182.
Yokota et al., "Clinical study of tocilizumab in children with systemic-onset juvenile idiopathic arthritis," Clin. Rev. Allergy Immunol., 28(3):231-8 (Jun. 2005).
Zalevsky et al., "Enhanced antibody half-life improves in vivo activity," Nat. Biotechnol., 28(2):157-9 (Feb. 2010).
Zhou et al., "Interfacial metal and antibody recognition," Proc Natl Acad Sci U S A., 102(41):14575-80 (Oct. 2005).
Zhu et al., "MHC class I-related neonatal Fc receptor for IgG is functionally expressed in monocytes, intestinal macrophages, and dendritic cells," J. Immunol., 166(5):3266-76 (Mar. 2001).
Zuckier et al., "Chimeric human-mouse IgG antibodies with shuffled constant region exons demonstrate that multiple domains contribute to in vivo half-life," Cancer Res., 58:3905-08 (Sep. 1998).
Zwick et al., "The long third complementarity-determining region of the heavy chain is important in the activity of the broadly neutralizing anti-human immunodeficiency virus type 1 antibody 2F5," J. Virol., 78(6):3155-61 (Mar. 2004).
International Search Report for App. Ser. No. PCT/JP2016/055768, dated May 17, 2016, 8 pages.
International Preliminary Report on Patentability for App. Ser. No. PCT/JP2016/055768, dated Sep. 8, 2017, 9 pages.
Cruse et al., Atlas of Immunology, CRC Press LLC, 2004, excerpt from Chapter 3, "Antigens and Immunogens", p. 109.
Decision of the EPO Opposition Division for EP 2 006 381 on Jul. 25, 2018, 17 pages.
Sequence alignments and modification scheme (document filed during Oral Proceedings in EPO opposition for EP 2 006 381 mentioned in minutes of the Oral Proceedings posted by EPO on Jul. 25, 2018), 3 pages.
Van Den Abbeele et al., "Antigen-Binding Site Protection During Radiolabeling Leads to a Higher Immunoreactive Fraction," J Nucl Med, Jan. 1991, 32(1):116-22.

(56) References Cited

OTHER PUBLICATIONS

U.S. Appl. No. 13/524,528, Igawa et al., filed Jun. 15, 2012.
U.S. Pat. No. 9,228,017, Igawa et al., issued Jan. 5, 2016.
U.S. Appl. No. 14/680,250, Igawa et al., filed Apr. 7, 2015.
U.S. Appl. No. 13/595,139, Igawa et al., filed Aug. 27, 2012.
U.S. Appl. No. 15/952,945, filed Apr. 13, 2018, Igawa et al.
U.S. Appl. No. 15/952,951, filed Apr. 13, 2018, Igawa et al.
U.S. Appl. No. 15/988,348, filed May 24, 2018, Igawa et al.
U.S. Appl. No. 16/041,976, filed Jul. 23, 2018, Igawa et al.
Balint et al., "Alterations of the peripheral B cell compartment in pediatric-onset multiple sclerosis," Journal of Neurology, May 2011, vol. 258, Suppl 1, pp. S202, Abstract No. P732.
Besada et al., "Potential patient benefit of a subcutaneous formulation of a tocilizumab for the treatment of rheumatoid arthritis: a critical review," Patient Preference and Adherence, Aug. 1, 2014, 8:1051-9. doi: 10.2147/PPA. S34958. eCollection 2014.
Canfield et al., "The Binding Affinity of Human IgG for its High Affinity Fc Receptor Is Determined by Multiple Amino Acids in the CH2 Domain and Is Modulated by the Hinge Region," J Exp Med, Jun. 1, 1991, 173(6):1483-91.
Dall'Acqua et al., "Properties of Human IgG1s Engineered for Enhanced Binding to the Neonatal Fc Receptor (FcRn)", J Biol Chem. Aug. 18, 2006;281(33):23514-24. Epub Jun. 21, 2006.
EPO Register Extract EP 1915397 (document submitted in EP opposition and posted by EPO on Feb. 2, 2018); 4 pages.
GE Healthcare, Biacore, Sensor Surface Handbook BR-1005-71, Edition AB, Feb. 2005, pp. 1-100.
Geneseq Accession No. AEM45140, Feb. 22, 2007, "Light chain constant region of therapeutic human IgG antibody".
Geneseq Accession No. ARZ17615, Aug. 21, 2008, "Human antibody IgG2 heavy chain constant region SEQ ID No. 36".
Hotzel et al., "A strategy for risk mitigation of antibodies with fast clearance," MAbs. Nov.-Dec. 2012;4(6):753-60. doi: 10.4161/mabs. 22189.
Huizinga et al., "Sarilumab, a fully human monoclonal antibody against IL-6Rα in patients with rheumatoid arthritis and an inadequate response to methotrexate: efficacy and safety results from the randomised SARIL-RA-MOBILITY Part A trial," Ann Rheum Dis., Sep. 2014, 73(9):1626-34. doi: 10. 1136/annrheumdis-2013-204405. Epub Dec. 2, 2013.
King, "Applications and Engineering of Monoclonal Antibodies," Taylor & Francis, ISBN 0-203-21169-3, pp. 1-236 (2005).
Mellman, "The importance of being acid: the role of acidification in intracellular membrane traffic," J Exp Biol, Nov. 1992, 172, 39-45.
Okiyama et al., "Therapeutic Effects of Interleukin-6 Blockade in a Murine Model of Polymyositis That Does Not Require Interleukin-17A," Arthritis & Rheumatism, Aug. 2009, 60(8):2505-2512.
Ryman et al., "Pharmacokinetics of Monoclonal Antibodies," CPT Pharmacometrics Syst Pharmacol. Sep. 2017;6(9):576-588. doi: 10.1002/psp4.12224. Epub Jul. 29, 2017.
Summary of information about antibodies in Examples of patent (document submitted in EP opposition and posted by EPO on Apr. 13, 2018); 3 pages.
Written Submissions by Opponent 1 (Alexion Pharmaceuticals, Inc.) in Opposition of EP 2006381 dated Apr. 13, 2018, 19 pages.
Written Submissions by Opponent 2 (Novo Nordisk A/S) in Opposition of EP 2006381 dated Apr. 13, 2018, 14 pages.
Written Submissions by Opponent 3 (name Unknown) in Opposition of EP 2006381 dated Apr. 13, 2018, 16 pages.
Wu et al., "Ultra-potent Antibodies Against Respiratory Syncytial Virus: Effects of Binding Kinetics and Binding Valence on Viral Neutralization," J Mol Biol. Jul. 1, 2005;350(1):126-44.
Yarilin, Fundamentals of Immunology M:Medicina, 1999, p. 169-72, 354-8 (with English translation) 21 pages.
Yarilin, Fundamentals of Immunology M:Medicina, 1999, pp. 172-174 (with English translation), 8 pages.
Interleukin 6, Wikipedia, Feb. 22. 2019, XP055598802, (URL:https://protect-us.mimecast.com/s/6UxpCmZ28nsApI8JuGhTki?domain=en.wikipedia.org), retrieved on Jun. 24, 2019, 20 pages.
U.S. Pat. No. 8,562,911, Igawa et al., issued Oct. 22, 2013.

U.S. Appl. No. 15/263,4617, Igawa et al., filed Sep. 13, 2016 (abandoned).
U.S. Pat. No. 9,228,017, Igawa et al., dated Jan. 5, 2016.
U.S. Appl. No. 14/962,293, Igawa et al., filed Dec. 8, 2015.
U.S. Pat. No. 10,253,091, Igawa et al., issued Nov. 22, 2011.
U.S. Appl. No. 13/575,139, Igawa et al., filed Aug. 27, 2012 (abandoned).
U.S. Appl. No. 13/990,158, Igawa et al., filed Mar. 28, 2014 (abandoned).
U.S. Appl. No. 15/952,945, Igawa etal., filed Apr. 13, 2018.
Aboud-Pirak et al., "Binding and Endocytosis of a Monoclonal Antibody to a High Molecular Weight Human Milk Fat Globule Membrane-associated Antigen by Cultured MCF-7 Breast Carcinoma Cells," Cancer Res, Jun. 1, 1988, 48(11):3188-96.
ACTEMRA (tocilizumab), Highlights of Prescribing Information, as revised in Aug. 2017 (1 page).
Anchin et al., "Recognition of Superpotent Sweetener Ligands by a Library of Monoclonal Antibodies," J Mol Recognit, Sep-Oct. 1997, 10(5):235-42.
Ando et al., "Tocilizumab, a Proposed Therapy for the Cachexia of Interleukin 6-Expressing Lung Cancer," PLOS One, Jul. 10, 2014 9(7):e102436. doi: 10.1371/journal.pone.0102436. eCollection 2014.
Barrabes et al., "Effect of sialic acid content on glycoprotein p*I* analyzed by two-dimensional electrophoresis," Electrophoresis, Sep. 2010, 31(17):2903-12. doi: 10.1002/elps.200900764.
Binding data for Rituximab (submitted by the Opponent during EP opposition procedure for EP 2 708 558 and posted by EPO on Jan. 15, 2019), 6 pages.
Chang et al., "Practical Approaches to Protein Formulation Development," Pharm Biotechnol, 2002, 13:1-25.
Chugai NMO Clinical Trial Webinar, Sakura Star Study, dated Dec. 12, 2014, downloaded on Sep. 5, 2019 from https://s3.amazonaws.com-gjcf-wp-uploads/wp-contert/uploads/2016/05/16162202/12_12_14_Chugai/Webinar_PPT_Complete_Deck_FINAL.pdf, 18 pages.
Chugai Pharmaceutical, A phase I, multiple-dose study of SA237, Study JapicCTI-No. 121786; submitted to Clinicaltrials.jp on Jan. 31, 2014; downloaded from clinicaltrials.jp archive on Sep. 5, 2019 as https://www.clinicaltrials.jp/cti-use/trial/Show.jsp, 5 pages.
Chugai Pharmaceutical, A phase I, multiple-dose study of SA237, Study JapicCTI-No. 121786; submitted to Clinicaltrials.jp on Jun. 19, 2012; downloaded from clinicaltrials.jp archive on Sep. 5, 2019 as https://www.clinicaltrials.jp/cti-user/trials/Show.jsp, 5 pages.
Chugai Pharmaceutical, A phase I, multiple-dose study of SA237, Study JapicCTI-No. 121786; submitted to Clinicaltrials.jp on Mar. 19, 2012; downloaded from clinicaltrials.jp archive on Sep. 5, 2019 as http://www.clinicaltrials.jp/cti-user/tri al/Show.jsp, 5 pages.
Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 1; submitted to ClinicalTrials.gov on Jan. 6, 2014; downloaded from ClinicalTrials.gov archive on Sep. 4, 2019 as http://www.clinicaltrials.gov/ct2/history/NCT0202884?V_1=View#StudyPageTop, 6 pages.
Chugai Pharmaceutical, Efficacy and Safety Study of Satralizumab (SA237) as Add-on Therapy to Treat Participants With Neuromyelitis Optica (Nmo) and Nmo Spectrum Disorder (Nmosd), Study NCT02028884, version 2; submitted to ClinicalTrials.gov on Feb. 25, 2014; downloaded from ClinicalTrials.gov archive on Sep. 4, 2019 as http://www.clinicaltrials.gov/ct2/history/NCT0202884?V_2=View#StudyPageTop, 6 pages.
Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 3; submitted to ClinicalTrials.gov on Sep. 4, 2015; downloaded from ClinicalTrials.gov archive on Sep. 4, 2019 as http://www.clinicaltrials.gov/ct2/history/NCT0202884?V_3=View#StudyPageTop, 6 pages.
Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 4; submitted to ClinicalTrials.gov on Dec.

(56) References Cited

OTHER PUBLICATIONS 8, 2015; downloaded from ClinicalTrials.gov archive on Sep. 4, 2019 as http://www.clinicaltrials.gov/ct2/history/NCT0202884?V_4=View#StudyPageTop, 6 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 1; submitted to ClinicalTrials.gov on Feb. 25, 2014; downloaded from ClinicalTrials.gov archive on Sep. 4, 2019 as http://www.clinicaltrials.gov/ct2/history/NCT0202884?V_1=View#StudyPageTop, 6 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 2; submitted to ClinicalTrials.gov on Jul. 22, 2014; downloaded from ClinicalTrials.gov archive on Sep. 5, 2019 as http://www.clinicaltrials.gov/ct2/history/NCT0202884?V_2=View#StudyPageTop, 6 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 3; submitted to ClinicalTrials.gov on Dec. 15, 2014; downloaded from ClinicalTrials.gov archive on Sep. 5, 2019 as http://www.clinicaltrials.gov/ct2/history/NCT0202884?V_3=View#StudyPageTop, 7 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 4; submitted to ClinicalTrials.gov on Feb. 5, 2015; downloaded from ClinicalTrials.gov archive on Sep. 5, 2019 as http://www.clinicaltrials.gov/ct2/history/NCT0202884?V_4=View#StudyPageTop, 8 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 5; submitted to ClinicalTrials.gov on Feb. 6, 2015; downloaded from ClinicalTrials.gov archive on Sep. 5, 2019 as http://www.clinicaltrials.gov/ct2/history/NCT0202884?V_5=View#StudyPageTop, 8 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 6; submitted to ClinicalTrials.gov on Mar. 4, 2015; downloaded from ClinicalTrials.gov archive on Sep. 5, 2019 as http://www.clinicaltrials.gov/ct2/history/NCT0202884?V_6=View#StudyPageTop, 9 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 7; submitted to ClinicalTrials.gov on Apr. 1, 2015; downloaded from ClinicalTrials.gov archive on Sep. 5, 2019 as http://www.clinicaltrials.gov/ct2/history/NCT0202884?V_7=View#StudyPageTop, 9 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 8; submitted to ClinicalTrials.gov on May 7, 2015; downloaded from ClinicalTrials.gov archive on Sep. 5, 2019 as http://www.clinicaltrials.gov/ct2/history/NCT0202884?V_8=View#StudyPageTop, 9 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 9; submitted to ClinicalTrials.gov on Jun. 5, 2015; downloaded from ClinicalTrials.gov archive on Sep. 5, 2019 as http://www.clinicaltrials.gov/ct2/history/NCT0202884?V_9=View#StudyPageTop, 9 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 10; submitted to ClinicalTrials.gov on Jul. 7, 2015; downloaded from ClinicalTrials.gov archive on Sep. 5, 2019 as http://www.clinicaltrials.gov/ct2/history/NCT0202884?V_10=View#StudyPageTop, 9 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 11; submitted to ClinicalTrials.gov on Aug. 3, 2015; downloaded from ClinicalTrials.gov archive on Sep. 5, 2019 as http://www.clinicaltrials.gov/ct2/history/NCT0202884?V_11=View#StudyPageTop, 10 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 12; submitted to ClinicalTrials.gov on Sep. 3, 2015; downloaded from ClinicalTrials.gov archive on Sep. 5, 2019 as http://www.clinicaltrials.gov/ct2/history/NCT0202884?V_12=View#StudyPageTop, 10 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 13; submitted to ClinicalTrials.gov on Oct. 5, 2015; downloaded from ClinicalTrials.gov archive on Sep. 5, 2019 as http://www.clinicaltrials.gov/ct2/history/NCT0202884?V_13=View#StudyPageTop, 10 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 14; submitted to ClinicalTrials.gov on Dec. 8, 2015; downloaded from ClinicalTrials.gov archive on Sep. 5, 2019 as http://www.clinicaltrials.gov/ct2/history/NCT0202884?V_14=View#StudyPageTop, 10 pages.
Costa et al., "Efficacy of tocilizumab in a patient with refractory psoriatic arthritis," Clin Rheumatol, Sep. 2014, 33(9):1355-7.
Decision of the Opposition Division in EP 2 275 443, dated Apr. 26, 2018 (submitted on May 24, 2019 by the Patentee during EPO Opposition Procedure for EP 2 202 245), 29 pages.
Declaration of Taichi Kuramochi (submitted on May 24, 2019 by the Patentee during EPO Opposition Procedure for EP 2 202 245), 11 pages.
Declaration of Dr. Anette Henriksen, signed Apr. 17, 2019 (submitted by the Opponent during EPO opposition procedure for EP 2 006 381), 4 pages.
Declaration by Madhusudan Natarajan, Ph.D. (submitted by the Opponent during EP opposition procedure for EP 2 708 558 and posted by EPO on Jan. 15, 2019), 3 pages.
F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and Nmo spectrum disorder (NMOSD), Study EudraCT 2013-003752-21 in Germany; submitted to clinicaltrialsregister.eu on Dec. 20, 2013; downloaded from clinicaltrialsregister.eu archive on Sep. 5, 2019 as https://www.clinicaltriaisregister.eu/ctr-search/trial/2013-003752-21/DE, 7 pages.
F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and Nmo spectrum disorder (NMOSD), Study EudraCT 2013-003752-21 in Hungary; submitted to clinicaltrialsregister.eu on Feb. 25, 2015; downloaded from clinicaltrialsregister.eu archive on Sep. 5, 2019 as https://www.clinicaltriaisregister.eu/ctr-search/trial/2013-003752-21/HU, 6 pages.
F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Italy; submitted to clinicaltrialsregister.eu on Feb. 6, 2014; downloaded from clinicaltrialsregister.eu archive on Sep. 5, 2019 as https://www.clinicaltriaisregister.eu/ctr-search/trial/2013-003752-21/IT, 5 pages.
F. Hoffmann-La Roche Ltd., A multicenter, randomized, addition to baseline treatment, double-blind, placebo-controlled, Phase 3 study to evaluate the efficacy and safety of Satralizumab (SA237) in

(56) References Cited

OTHER PUBLICATIONS patients with neuromyelitis optica (NMO) and NMO spectrum disorder (NMOSD), Study EudraCT 2013-003752-21 in Poland; submitted to clinicaltrialsregister.eu on Oct. 15, 2013; downloaded from clinicaltriaisregister.eu archive on Sep. 5, 2019 as https://www.clinicaltriaisregister.eu/ctr-search/trial/2013-003752-21/GB, 7 pages.
F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Spain; submitted to clinicaltrialsregister.eu on Mar. 11, 2015; downloaded from clinicaltriaisregister.eu archive on Sep. 5, 2019 as https://www.clinicaltriaisregister.eu/ctr-search/trial/2013-003752-21/ES, 7 pages.
F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in the United Kingdom; submitted to clinicaltrialsregister.eu on Oct. 15, 2013; downloaded from clinicaltrialsregister.eu archive on Sep. 5, 2019 as https://www.clinicaltriaisregister.eu/ctr-search/trial/2013-003752-21/GB, 6 pages.
F. Hoffmann-La Roche Ltd., A Multicenter, Randomized, Double-blind, Placebo-controlled, Phase 3 Study to Evaluate the Efficacy and Safety of Satralizumab (SA237) as Monotherapy in Patients With Neuromyelitis Optica (NMO) and Neuromyelitis Optica Spectrum Disorder (NMOSD), Study EudraCT 2015-005431-41 in Croatia; submitted to clinicaltrialsregister.eu on Dec. 15, 2016; downloaded from clinicaltrialsregister.eu archive on Sep. 5, 2019 as https://www.clinicaltriaisregister.eu/ctr-search/trial/2015-005431-41/HR, 6 pages.
F. Hoffmann-La Roche Ltd., A Multicenter, Randomized, Double-blind, Placebo-controlled, Phase 3 Study to Evaluate the Efficacy and Safety of Satralizumab (SA237) as Monotherapy in Patients With Neuromyelitis Optica (NMO) and Neuromyelitis Optica Spectrum Disorder (NMOSD), Study EudraCT 2015-005431-41 in Poland; submitted to clinicaltrialsregister.eu on Apr. 7, 2016; downloaded from clinicaltrialsregister.eu archive on Sep. 5, 2019 as https://www.clinicaltriaisregister.eu/ctr-search/trial/2015-005431-41/PL, 6 pages.
Ferl et al., "A Predictive Model of Therapeutic Monoclonal Antibody Dynamics and Regulation by the Neonatal Fc Receptor (FcRn)," Ann Biomed Eng, Nov. 2005, 33(11):1640-52; and Erratum, Oct. 2011, 39(10):2668.
Fisher et al., "Affinity purification of antibodies using antigens immobilized on solid supports," Biochem Soc Trans, Apr. 1988, 16(2):134-8.
Furuya et al., "Interleukin-6 as a Potential Therapeutic Target for Pulmonary Arterial Hypertension," Int J Rheumatol, Aug. 2010, 2010:720305:1-8. doi: 10.1155/2010/720305. Epub Aug. 2, 2010.
Gopferich et al., Chapter 15 "Drug Delivery from Bioerodible Polymers," in Formulation and Delivery of Proteins and Peptides, American Chemical Society, eds. Cleland et al., 1994, pp. 242-277.
Granted claims of EP 2 275 443 (submitted on May 24, 2019 by the Patentee during EPO Opposition Procedure for EP 2 202 245), 1 page.
Hashizume et al., "Tocilizumab, a humanized anti-interleukin-6 receptor antibody, improved anemia in monkey arthritis by suppressing IL-6-induced hepcidin production," Rheumatol Int, May 2010, 30(7):917-23. doi: 10.1007/s00296-009-1075-4. Epub Jul. 29, 2009.
Honda et al., "Marginal zone B cells exacerbate endotoxic shock via interleukin-6 secretion induced by Fca/mR-coupled TLR4 signalling," Nat Commun, May 5 2016, 7:11498. doi: 10.1038/ncomms11498.
Hughes-Jones et al., "The Effect of pH and Ionic Strength on the Reaction between Anti-D and Erythrocytes," Immunology, Jan. 1964, 7:72-81.
Huse et al., "Purification of antibodies by affinity chromatography," J Biochem Biophys Methods, May 31, 2002, 51(3):217-31.

Iijima et al., "Tocilizumab improves systemic rheumatoid vasculitis with necrotizing crescentic glomerulonephritis," Mod Rheumatol, Jan. 2015, 25(1):138-42. doi: 0.3109/14397595.2013.874748. Epub Feb. 18, 2014.
Jain et al., "Engineering antibodies for clinical applications," Trends Biotechnol, Jul. 2007, 25(7):307-16. Epub May 21, 2007.
Kamata et al., "Comparison of pH and Ionic Strength Dependence of Interactions between Monoclonal Antibodies and Bovine β-Lactoglobulin," Biosci Biotechnol Biochem, Jan. 1996, 60(1):25-9.
King, Applications and Engineering of Monoclonal Antibodies, Chapter 2 "Antibody Engineering: Design for Specific Applications," 1998, pp. 27-75.
Kishimoto, "Interleukin-6 and its Receptor in Autoimmunity," J Autoimmun, Apr. 1992, 5 Suppl A:123-32.
Kondo et al., "A case of overlap syndrome successfully treated with tocilizumab: a hopeful treatment strategy for refractory dermatomyositis?," Rheumatology (Oxford), Oct. 2014, 53(10):1907-8. doi: 10.1093/rheumatology/keu234. Epub May 23, 2014.
Kranz et al., "Mechanisms of Ligand Binding by Monoclonal Anti-fluorescyl Antibodies," J Biol Chem, Jun. 25, 1982, 257(12):6987-95.
Mihara et al., "Anti-interleukin 6 receptor antibody inhibits murine AA-amyloidosis," J Rheumatol, Jun. 2004, 31(6):1132-8.
Mori et al., "Novel models of cancer-related anemia in mice inoculated with IL-6-producing tumor cells," Biomed Res, Feb. 2009, 30(1):47-51.
Motozawa et al., "Unique circumferential peripheral keratitis in relapsing polychondritis," Medicine (Baltimore), Oct. 2017, 96(41):e7951. doi: 10.1097/MD.0000000000007951.
Narazaki et al., "Therapeutic effect of tocilizumab on two patients with polymyositis,"Rheumatology (Oxford), Jul. 2011, 50(7):1344-6. doi: 10.1093/rheumatology/ker152. Epub Apr. 2011.
Narhi et al., "Effect of Three Elution Buffers on the Recovery and Structure of Monoclonal Antibodies," Anal Biochem, Nov. 15, 1997, 253(2):236-45.
Originally Filed Claims of EP Application No. 13195713.6 (EP Publication No. 2 708 558)(submitted by the Opponent during EP opposition procedure for EP 2 708 558 amd posted by EPO on Jan. 15, 2019), 2 pages.
Originally Filed Description of Ep Application No. 13195713.6 (EP Publication No. 2708558)(submitted by the Opponent during EP opposition procedure for EP 2 708 558 amd posted by EPO on Jan. 15, 2019), 153 pages..
Patel et al., "A Forgotten Cause of Kidney Injury in Chronic Myelomonocytic Leukemia," Am J Kidney Dis, Jul. 2009, 54(1):159-64. doi: 10.1053/j.ajkd.2008.11.013. Epub Jan. 29, 2009.
Product Information Sheet from SIGMA—H-Y Medium (1998) and document establishing that it was published in 1998 (submitted by the Opponent during EP opposition procedure for EP 2 708 558 and posted by EPO on Jan. 15, 2019), 4 pages.
Promega Protocols and Applications Guide, 1991, 2nd Edition (submitted by the Opponent during EP opposition procedure for EP 2 708 558 and posted by EPO on Jan. 14, 2019), 3 pages.
Raso, "Intracellular Targeting Using Bispecific Antibodies," Methods in Molecular Medicine, vol. 25: Drug Targeting: Strategies, Principles, and Applications, 2000, pp. 37-50.
Raso et al., "Intracellular Targeting with Low pH-triggered Bispecific Antibodies," J Biol Chem, Oct. 31, 1997, 272(44):27623-8.
Raso et al., "Antibodies Capable of Releasing Diphtheria Toxin in Response to the Low pH Found in Endosomes," J Biol Chem, Oct. 31, 1997, 272(44):27618-22.
Reverberi et al., "Factors affecting the antigen-antibody reaction," Blood Transfus, Nov. 2007, 5(4):227-40. doi: 10.2450/2007.0047-07.
Rituximab biologic license application approval, dated Nov. 26, 1997 (submitted by the Opponent during EP opposition procedure for EP 2 708 558 and posted by EPO on Jan. 15, 2019), 2 pages.
Rituximab (Wikipedia), accessed on Oct. 24, 2018 (submitted by the Opponent during EP opposition procedure for EP 2 708 558 and posted by EPO on Jan. 15, 2019), 7 pages.

(56) References Cited

OTHER PUBLICATIONS

Rituximab product information, IDEC, 1997 (submitted by the Opponent during EP opposition procedure for EP 2 708 558 and posted by EPO on Jan. 15, 2019), 2 pages.
Sada et al., "Effect of histidine residues in antigenic sites on pH dependence of immuno-adsorption equilibrium," Appl Microbiol Biotechnol, Feb. 1988, 27:528-32.
Serada et al., "IL-6 blockade inhibits the induction of myelin antigen-specific Th17 cells and Th1 cells in experimental autoimmune encephalomyelitis," Proc Natl Acad Sci USA, Jul. 1, 2008, 105(26):9041-6. doi: 10.1073/pnas.0802218105. Epub Jun. 24, 2008.
Shadduck et al., "Fractionation of Antibodies to L-Cell Colony-Stimulating Factor by Affinity Chromatography," Blood, Jun. 1979, 53(6):1182-90.
Shima et al., "Tocilizumab, a humanized anti-interleukin-6 receptor antibody, ameliorated clinical symptoms and MRI findings of a patient with ankylosing spondylitis," Mod Rheumatol, Aug. 2011, 21(4):436-9. doi: 10.1007/s10165-011-0416-9. Epub Feb. 9, 2011.
Shimizu et al., "Successful treatment with tocilizumab for refractory scleritis associated with relapsing polychondritis," Scand J Rheumatol, Sep. 2017, 46(5):418-419. doi: 10.1080/03009742.2016.1275774. Epub Jan. 25, 2017.
Silpa-Archa et al., "Outcome of tocilizumab treatment in refractory ocular inflammatory diseases," Acta Ophthalmol, Sep. 2016, 94(6):e400-6. doi: 10.1111/aos.13015. Epub Mar. 24, 2016.
Supplemental Material to Raposo et al., "Epitope-specific antibody response is controlled by immunoglobulin VH polymorphisms," J Exp Med, Mar. 10, 2014, 211(3):405-11. doi: 10.1084/jem.20130968. Epub Feb. 17, 2014 (submitted on May 24, 2019 by the Patentee during EPO Opposition Procedure for EP 2 202 245), 4 pages.
Suzuki et al., "Anti-murine IL-6 receptor antibody inhibits IL-6 effects in vivo," Immunol Lett, Sep. 1991, 30(1):17-21.
Venturi et al., "The Monoclonal Antibody 1F6 Identifies a pH-dependent Conformational Change in the Hydrophilic NH2 Terminus of NhaA Na+/H+ Antiporter of *Escherichia coli*," J Biol Chem, Feb. 18, 2000, 275(7):4734-42.
Wang, "Instability, stabilization, and formulation of liquid protein pharmaceuticals," Int J Pharm, Aug. 20, 1999, 185(2):129-88.
U.S. Pat. No. 8,562,991, Igawa et al., issued Oct. 22, 2013.
U.S. Appl. No. 13/524,528, Igawa et al., filed Jun. 15, 2012 (abandoned).
U.S. Appl. No. 14/520,423, Igawa et al., filed Oct. 22, 2014.
U.S. Appl. No. 16/838,415, Igawa et al., filed Apr. 2, 2020.
U.S. Pat. No. 9,688,762, Igawa et al., issued Jun. 27, 2017.
U.S. Appl. No. 15/614,842, Igawa et al., filed Jun. 6, 2017.
U.S. Appl. No. 12/680,112, Igawa et al., filed Jun. 23, 2010 (abandoned).
U.S. Appl. No. 13/959,489, Igawa et al., filed Aug. 5, 2013 (abandoned).
U.S. Appl. No. 15/263,617, Igawa et al., filed Sep. 13, 2016 (abandoned).
U.S. Appl. No. 16/041,976, Igawa et al., filed Jul. 23, 2018.
U.S. Pat. No. 9,228,017, Igawa et al., filed Jan. 5, 2016.
U.S. Pat. No. 10,066,018, Igawa et al., issued Sep. 4, 2018.
U.S. Appl. No. 13/257,145, Igawa et al., filed Nov. 22, 2011 (abandoned).
U.S. Pat. No. 10,253,091, Igawa et al., issued Apr. 9, 2019.
U.S. Appl. No. 16/298,032, Igawa et al., filed Mar. 11, 2019.
U.S. Appl. No. 15/575,027, Yamamura et al., filed Nov. 17, 2017.
U.S. Appl. No. 12/936,587, Igawa et al., filed Jan. 3, 2011 (abandoned).
U.S. Appl. No. 13/595,139, Igawa et al., filed Aug. 27, 2012 (abandoned).
U.S. Pat. No. 9,868,948, Igawa et al., issued Jan. 16, 2018.
U.S. Pat. No. 9,890,377, Igawa et al., issued Feb. 13, 2018.
U.S. Appl. No. 12/295,039, Igawa et al., filed Jan. 20, 2009.
U.S. Pat. No. 9,096,651, Igawa et al., issued Aug. 4, 2015.
U.S. Pat. No. 9,828,429, Igawa et al., issued Nov. 28, 2017.
U.S. Appl. No. 15/725,692, Igawa et al., filed Oct. 5, 2017.
U.S. Appl. No. 15/900,158, Igawa et al., filed Mar. 28, 2014 (abandoned).
U.S. Appl. No. 15/988,348, Igawa et al., filed May 24, 2018.
U.S. Appl. No. 14/897,498, Yamura et al., filed Dec. 10, 2015.
U.S. Pat. No. 10,472,623, Igawa et al., issued Nov. 12, 2019.
U.S. Appl. No. 15/952,951, Igawa etal., filed Apr. 13, 2018.
U.S. Appl. No. 16/361,498, Igawa etal., filed Mar. 22, 2019.
U.S. Appl. No. 16/609,053, Matsuoka et al., filed Oct. 28, 2019.
U.S. Appl. No. 16/756,404, Fujimoto et al., filed Apr. 15, 2020.
Curtiss, "Selectivity and Specificity Are the Keys to Cost-Effective Use of Omalizumab for Allergic Asthma," J Manag Care Pharm, Nov.-Dec. 2005, 11(9):774-6.
Edwards et al., "The Remarkable Flexibility of the Human Antibody Repertoire; Isolation of Over One Thousand Different Antibodies to a Single Protein, BLyS," J Mol Biol, Nov. 14, 2003 334(1):103-118.
Expert Declaration of Joachim Boucneau, signed Mar. 11, 2020 (submitted by the Opponents in Mar. 2020 in Oppositions of EP 2 708 558 and EP 2 708 559).
Guidance on the use of International Nonproprietary Names (INNs) for Pharmaceutical Substances, World Health Organization, 2017, 55 pages. (submitted by Opponents in Mar. 2020 in Oppositions of EP 2 708 558 and EP 2 708 559)
Igawa et al., "pH-dependent antigen-binding antibodies as a novel therapeutic modality," Biochim Biophys Acta, Nov. 2014, 1844(11):1943-1950. doi: 10.1016/j.bbapap.2014.08.003. Epub Aug. 12, 2014.
Kussie et al., "A Single Engineered Amino Acid Substitution Changes Antibody Fine Specificity," J Immunol, Jan. 1, 1994, 152:146-152.
Lloyd et al., "Modelling the human immune response: performance of a $10^{11}$ human antibody repertoire against a broad panel of therapeutically relevant antigens," Protein Engineering, Design & Selection, Oct. 29, 2009, 22:159-168.
Rich et al., "A global benchmark study using affinity-based biosensors," Anal Biochem, Mar. 15, 2009, 386(2):194-216. doi: 10.1016/j.ab.2008.11.021. Epub Nov. 27, 2008.
Roche Media Release, dated Jan. 5, 2011, 4 pages, retrieved from the internet <https://www.roche.com/media/releases.med-cor-2011-01-05.htm>, (submitted by Opponents in Mar. 2020 in Oppositions of EP 2 708 558 and EP 2 708 559).
Van et al., Adalimumab in Crohn's Disease, Biologics, Dec. 2007, 1(4):355-65.
Yu et al., "Development and Validation of a Cell-Based Fluorescent Method for Measuring Antibody Affinity," J Immunol Methods, Mar. 2017, 442:49-53. doi: 10.1016/j jim.2016.12.004. Epub Dec. 24 2016.
U.S. Pat. No. 10,066,018, Igawa et al., issued Sep. 22, 2011.
Araki et al., "Emerging Disease-modifying Therapies for Neuromyelitis Optica Spectrum Disorder," The Medical Frontline, 2016, 71(6):1159-1167 (with English translation).
Hisanaga et al., "Neuro-Behcet disease and neuro-Sweet disease," Clinical Neurology, Dec. 31, 2011, 52:1234-1236 (with English abstract).
Ishikawa et al., "Dna microarray analysis of SLE related genes that respond to IL-6 blockade with tocilizumab, an anti-IL-6 receptor monoclonal antibody," Annals of the Rheumatic Diseases, 2006, 65(suppl 2):474.
Jacob et al., "Detrimental role of granulocyte-colony stimulating factor in neuromyelitis optica: clinical case and histological evidence," Mult Scler, Dec. 2012, 18(12):1801-1803. doi: 10.1177/1352458512443994. Epub Apr. 11, 2012.
Kakita et al., "Isolation of a Human Monoclonal Antibody with Strong Neutralizing Activity against Diphtheria Toxin," Infection and Immunity, Jun. 2006, 74(6):3682-3683.
Nishimoto et al., "Expressions of immune response related genes were normalized after tocilizumab treatment in rheumatoid arthritis (Ra) patients," Annals of the Rheumatic Diseases, 2013, 71(suppl 3):380.
Perez-Sanchez et al., "Diagnostic potential of NETosis-derived products for disease activity, atherosclerosis and therapeutic effectiveness in Rheumatoid Arthritis patients," J of Autoimmun, Aug. 2017, 82:31-40. doi: 10.1016/j.jaut.2017.04.007. Epub Apr. 29, 2017.

(56) References Cited

OTHER PUBLICATIONS

Ruiz-Limon et al., "Tocilizumab improves the proatherothrombotic profile of rheumatoid arthritis patients modulating endothelial dysfunction, NETosis, and inflammation," Transl Res, 2017 May 2017, 183:87-103. doi: 10.1016/j.trsl.2016.12.003. Epub Dec. 9, 2016.

Saadoun et al., "Neutrophil Protease Inhibition Reduces Neuromyelitis Optica-Immunoglobulin G-Induced Damage in Mouse Brain," Ann Neurol, Mar. 2012, 71(3):323-333. doi: 10.1002/ana.22686. Epub Feb. 28, 2012.

Tanaka et al., "Therapeutic Targeting of the Interleukin-6 Receptor," Annu Rev Pharmacol Toxicol, 2012, 52:199-219. doi: 10.1146/annurev-pharmtox-010611-134715. Epub 2011 Sep 9.

Yamamura, "Anti-Il-6 receptor therapy for neuromyelitis optica," Neurological Therapeutics 31 Oct. 2016, 33(5):5120 (with English translation).

Yamamura, "Anti-Il-6 receptor therapy for neuromyelitis optica," Presentation given at the 34th Annual Meeting of Japanese Society of Neurological Therapeutic, 2016 Nov 4, 62 pp. (with English translation).

Yamamura, "Treatment failures in Nmo are due to specific immunologic mechanisms," Meeting of the 9th Annual International Roundtable Conference on Nmo, 2017 Mar 13, 17 pages.

\* cited by examiner

OBSERVATION AND TESTING SCHEDULE (PRIMARY EVALUATION PERIOD)

| WEEK | 0 | 0 | 1 | 2 | 4 | 8 | 12 | 16 | 20 | 24 | 28 | 32 |
|---|---|---|---|---|---|---|---|---|---|---|---|---|
| DAY | 1 | 4 | 8 | 15 | 29 | 57 | 85 | 113 | 141 | 169 | 197 | 225 |
| PERMISSIBLE RANGE | | ±1 | ±2 | ±3 | ±3 | ±3 | ±3 | ±3 | ±3 | ±3 | ±3 | ±3 |
| SA237 ADMINISTRATION | ● | | | ● | ● | ● | ● | ● | | | | |
| ADVERSE EVENT | ←─────────────────────────────────────────→ | | | | | | | | | | | |
| PREGNANCY TEST (SERUM OR URINE) | ● | | | ● | ● | ● | ● | ● | ● | ● | ● |
| ANTI-CCP ANTIBODY, RHEUMATOID FACTOR | ● | | | | | | | | ● | | | |
| VITAL SIGN | ● | | | ● | ● | ● | ● | ● | ● | | | |
| BODY WEIGHT | ● | | | | | | | | ● | | | |
| ELECTROCARDIOGRAM | ● | | ● | | | | | | ● | | | |
| CHEST X-RAY (OR CHEST CT) | | | | | | | | | ● | | | |
| TENDER AND SWOLLEN JOINT COUNT | ● | | | | ● | ● | ● | ● | ● | | | |
| VAS SUBJECTS/PHYSICIAN | ● | | | | ● | ● | ● | ● | ● | | | |
| JHAQ | ● | | | | ● | ● | ● | ● | ● | | | |
| CRP | ● | | | ● | ● | ● | ● | ● | ● | ● | ● | ● |
| ESR | ● | | | | ● | ● | ● | ● | ● | | | |
| MMP-3 | ● | | | | ● | ● | ● | ● | ● | | | |
| HEMATOLOGICAL EXAMINATION | ● | | | ● | ● | ● | ● | ● | ● | | | |
| BLOOD COAGULATION EXAMINATION | ● | | | ● | ● | ● | ● | ● | ● | | | |
| BLOOD BIOCHEMICAL EXAMINATION | ● | | | ● | ● | ● | ● | ● | ● | | | |
| URINALYSIS | ● | | | ● | ● | ● | ● | ● | ● | | | |
| COMPLEMENT ACTIVITY | ● | | | | ● | ● | ● | ● | ● | | | |
| ANTI-SA237 ANTIBOODY | ● | | | | ● | ● | ● | ● | ● | ● | ● | ● |
| PHARMACOKINETICS | ● | ● | ● | ● | ● | ● | ● | ● | ● | ● | ● | ● |
| IL-6 | ● | | | ● | ● | ● | ● | ● | ● | | | |
| SOLUBLE IL-6 RECEPTOR | ● | | | ● | ● | ● | ● | ● | ● | ● | ● | ● |

FIG. 4

OBSERVATION AND TESTING SCHEDULE (EXTENSION PERIOD AND FOLLOW-UP PERIOD)

| WEEK | 0 | 0 | 1 | 2 | 4 | 8 | 12 | 16 | 20 | 24 | 32 |
|---|---|---|---|---|---|---|---|---|---|---|---|
| DAY | 1 | 4 | 8 | 15 | 29 | 57 | 85 | 113 | 141 | 169 | 225 |
| PERMISSIBLE RANGE | | ±1 | ±2 | ±3 | ±7 | ±7 | ±7 | ±7 | ±7 | ±7 | ±7 |
| SA237 ADMINISTRATION | ● | | | ● | ● | ● | ● | ● | ● | | |
| ADVERSE EVENT | ←  |   |   |   |   |   |   |   |   |   | → |
| PREGNANCY TEST (SERUM OR URINE) | ● | | | | ● | ● | ● | ● | ● | ● | |
| ANTI-CCP ANTIBODY, RHEUMATOID FACTOR | | | | | | | | | | ● | |
| VITAL SIGN | ● | | | ● | ● | ● | ● | ● | ● | ● | |
| BODY WEIGHT | ● | | | | | | | | | ● | |
| ELECTROCARDIOGRAM | ● | | | | | | | | | ● | |
| CHEST X-RAY (OR CHEST CT) | | | | | | | | | | ● | |
| TENDER AND SWOLLEN JOINT COUNT | ● | | | | ● | ● | ● | ● | ● | ● | |
| VAS SUBJECTS/PHYSICIAN | ● | | | | ● | ● | ● | ● | ● | ● | |
| JHAQ | ● | | | | ● | ● | ● | ● | ● | ● | |
| CRP | ● | | | ● | ● | ● | ● | ● | ● | ● | ● |
| ESR | ● | | | | ● | ● | ● | ● | ● | ● | |
| MMP-3 | ● | | | | ● | ● | ● | ● | ● | ● | |
| HEMATOLOGICAL EXAMINATION | ● | | | ● | ● | ● | ● | ● | ● | ● | ● |
| BLOOD COAGULATION EXAMINATION | ● | | | ● | ● | ● | ● | ● | ● | ● | ● |
| BLOOD BIOCHEMICAL EXAMINATION | ● | | | ● | ● | ● | ● | ● | ● | ● | ● |
| URINALYSIS | ● | | | ● | ● | ● | ● | ● | ● | ● | ● |
| ANTI-SA237 ANTIBOODY | ● | | | | ● | ● | ● | ● | ● | ● | ● |
| PHARMACOKINETICS | ● | ● | ● | ● | ● | ● | ● | ● | ● | ● | ● |
| IL-6 | ● | | | ● | ● | ● | ● | ● | ● | ● | ● |
| SOLUBLE IL-6 RECEPTOR | ● | | | ● | ● | ● | ● | ● | ● | ● | ● |

FIG. 5

SEQUENCE LISTING

<160> NUMBER OF SEQ ID NOS: 4

<210> SEQ ID NO 1
<211> LENGTH: 119
<212> TYPE: PRT
<213> ORGANISM: Artificial
<220> FEATURE:
<223> OTHER INFORMATION: An artificially synthesized polypeptide
      sequence

<400> SEQUENCE: 1

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser
        115

<210> SEQ ID NO 2
<211> LENGTH: 107
<212> TYPE: PRT
<213> ORGANISM: Artificial
<220> FEATURE:
<223> OTHER INFORMATION: An artificially synthesized polypeptide
      sequence

<400> SEQUENCE: 2

Asp Ile Gln Met Thr Gln Ser Pro Ser Ser Leu Ser Ala Ser Val Gly
1               5                   10                  15

Asp Ser Val Thr Ile Thr Cys Gln Ala Ser Thr Asp Ile Ser Ser His
            20                  25                  30

Leu Asn Trp Tyr Gln Gln Lys Pro Gly Lys Ala Pro Glu Leu Leu Ile
        35                  40                  45

Tyr Tyr Gly Ser His Leu Leu Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu
            100                 105

<210> SEQ ID NO 3
<211> LENGTH: 443
<212> TYPE: PRT
<213> ORGANISM: Artificial
<220> FEATURE:
<223> OTHER INFORMATION: An artificially synthesized polypeptide
      sequence

<400> SEQUENCE: 3

```
Gln Val Gln Leu Gln Glu Ser Gly Pro Gly Leu Val Lys Pro Ser Glu
 1               5                  10                  15

Thr Leu Ser Leu Thr Cys Ala Val Ser Gly His Ser Ile Ser His Asp
             20                  25                  30

His Ala Trp Ser Trp Val Arg Gln Pro Pro Gly Glu Gly Leu Glu Trp
         35                  40                  45

Ile Gly Phe Ile Ser Tyr Ser Gly Ile Thr Asn Tyr Asn Pro Ser Leu
 50                  55                  60

Gln Gly Arg Val Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
            195                 200                 205

Ser Asn Thr Lys Val Asp Lys Thr Val Glu Arg Lys Ser Cys Val Glu
210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Phe Arg Val Val Ser Val Leu
290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415
```

```
Glu Gly Asn Val Phe Ser Cys Ser Val Met His Glu Ala Leu His Ala
            420                 425                 430

His Tyr Thr Gln Lys Ser Leu Ser Leu Ser Pro
        435                 440

<210> SEQ ID NO 4
<211> LENGTH: 214
<212> TYPE: PRT
<213> ORGANISM: Artificial
<220> FEATURE:
<223> OTHER INFORMATION: An artificially synthesized polypeptide
      sequence

<400> SEQUENCE: 4

Asp Ile Gln Met Thr Gln Ser Pro Ser Ser Leu Ser Ala Ser Val Gly
1               5                   10                  15

Asp Ser Val Thr Ile Thr Cys Gln Ala Ser Thr Asp Ile Ser Ser His
            20                  25                  30

Leu Asn Trp Tyr Gln Gln Lys Pro Gly Lys Ala Pro Glu Leu Leu Ile
        35                  40                  45

Tyr Tyr Gly Ser His Leu Leu Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

COMPOSITION FOR TREATING IL-6-RELATED DISEASES

CROSS-REFERENCE TO RELATED APPLICATIONS

This application is the National Stage of International Application Serial No. PCT/JP2016/055768, filed on Feb. 26, 2016, which claims the benefit of Japanese Application Serial No. 2015-037933, filed on Feb. 27, 2015.

TECHNICAL FIELD

The present invention relates to pharmaceutical compositions or dosage regimen used for treating IL-6-related diseases.

BACKGROUND ART

Interleukin-6 (IL-6) is a cytokine also referred to as B cell stimulating factor 2 (BSF2) or interferon β2. IL-6 was discovered as a differentiation factor involved in the activation of B lymphoid cells (Non-patent Document 1), and it was later found to be a multifunctional cytokine that affects the functions of a variety of cells (Non-patent Document 2). IL-6 has been reported to induce maturation of T lymphoid cells (Non-patent Document 3).

IL-6 transmits its biological activity via two types of proteins on cells. One of them is the IL-6 receptor, which is a ligand-binding protein that has a molecular weight of approximately 80 kD to which IL-6 binds (Non-patent Documents 4 and 5). The IL-6 receptor exists as a soluble IL-6 receptor, which is mainly composed of its extracellular region, in addition to a membrane-bound form expressed on the cell membrane and penetrates through the cell membrane.

The other one is membrane protein gp130, which has a molecular weight of about 130 kDa and is involved in non-ligand-binding signal transduction. The biological activity of IL-6 is transmitted into a cell through formation of an IL-6/IL-6 receptor complex by IL-6 and the IL-6 receptor, followed by binding of the complex with gp130 (Non-patent Document 6).

IL-6 inhibitors are substances that inhibit the transmission of IL-6 biological activity. So far, antibodies against IL-6 (anti-IL-6 antibodies), antibodies against the IL-6 receptor (anti-IL-6 receptor antibodies), antibodies against gp130 (anti-gp130 antibodies), IL-6 variants, partial peptides of IL-6 or the IL-6 receptor, and such have been known.

There are several reports regarding the anti-IL-6 receptor antibodies (Non-patent Documents 7 and 8, and Patent Documents 1-3). One of them is a humanized PM-1 antibody obtained by transplanting the complementarity determining region (CDR) of mouse antibody PM-1 (Non-patent Document 9) into a human antibody (Patent Document 1).

Tocilizumab, which is an anti-IL-6 receptor antibody, is currently used to treat inflammatory diseases such as rheumatoid arthritis and Castleman's disease (Non-patent Document 10), and it has been also confirmed to be effective for diseases such as neuromyelitis optica (NMO) (Non-patent Document 11).

Therapeutic effects of IL-6 antibodies on myasthenia gravis have been reported as well (Non-patent Document 12).

Humanized antibodies such as tocilizumab are first-generation antibody pharmaceuticals. Second-generation antibody pharmaceuticals are currently being developed by improving the drug efficacy, convenience, and cost of the first-generation antibody pharmaceuticals (Patent Document 2). As a second-generation antibody pharmaceutical, SA237, a new anti-IL-6 receptor antibody, has been produced by applying improvement technologies such as those for enhancing effector function, antigen-binding capacity, pharmacokinetics, and stability, or those for reducing immunogenic risks, and is already entered into clinical trials.

Although many antibody treatments are currently being performed, attenuation of therapeutic effects due to the development of anti-antibodies has been confirmed in alemtuzumab. In order to prevent this attenuation, it has been reported to be effective to administer a non-cell-binding mutant that can be administered in high doses, instead of inducing immunological tolerance by administering a high dose of alemtuzumab (Non-patent Document 13).

The prior-art documents related to the invention of this application are shown below.

PRIOR ART DOCUMENTS

Non-Patent Document

[Non-patent Document 1] Hirano, T. et al., Nature (1986) 324, 73-76
[Non-patent Document 2] Akira, S. et al., Adv. in Immunology (1993) 54, 1-78
[Non-patent Document 3] Lotz, M. et al., J. Exp. Med. (1988) 167, 1253-1258
[Non-patent Document 4] Taga, T. et al., J. Exp. Med. (1987) 166, 967-981
[Non-patent Document 5] Yamasaki, K. et al., Science (1988) 241, 825-828
[Non-patent Document 6] Taga, T. et al., Cell (1989) 58, 573-581
[Non-patent Document 7] Novick, D. et al., Hybridoma (1991) 10, 137-146
[Non-patent Document 8] Huang, Y W. et al., Hybridoma (1993) 12, 621-630
[Non-patent Document 9] Hirata, Y et al., J. Immunol. (1989) 143, 2900-2906
[Non-patent Document 10] Nishimoto, N. et al., Blood. 2005 Oct. 15; 106(8):2627-32
[Non-patent Document 11] Araki et al., Mod. Rheumatol. (2013) 23(4), 827-831
[Non-patent Document 12] Aricha, R. et al., J. Autoimmun. (2011) 36(2), 135-141
[Non-patent Document 13] Charlotte L. et al., Nature Reviews Rheumatology (2010) 6, 558-559

Patent Document

[Patent Document 1] International Patent Application Publication No. WO 92-19759
[Patent Document 2] International Patent Application Publication No. WO 2010/035769

SUMMARY OF THE INVENTION

Problems to be Solved by the Invention

Even with SA237 (an antibody having the heavy chain sequence of SEQ ID NO: 3 and the light chain sequence of SEQ ID NO: 4), which is produced by applying technologies for reducing immunogenicity, in a Phase I study (SA-001JP) of subcutaneously administering a single dose of 120 mg of SA237 to healthy adult male subjects, anti-SA237 antibodies were generated in 54.2% of the cases (39 out of 72 cases) and an immunogenic problem occurred. An objective of the present invention is to suppress anti-antibody generation and provide more effective pharmaceutical compositions or dosage regimen to be used in the treatment of IL-6-related diseases.

Means for Solving the Problems

To solve the above-mentioned problems, the present inventors focused on immunological tolerance, and discovered that anti-antibody generation can be suppressed by administering a pharmaceutical composition with a predetermined administration method and dose.

More specifically, the present inventors discovered that anti-antibody generation can be suppressed by using a pharmaceutical composition administered at a predetermined dose and administration method to treat IL-6-related diseases, and thereby completed the present invention.

Specifically, the present invention includes the following:
[1] A pharmaceutical composition for use in treating an IL-6-related disease comprising an IL-6 inhibitor as an active ingredient, wherein the pharmaceutical composition is routinely administered after a short-interval dosing period where the same dose as the routine dose is administered multiple times at a shorter interval than the routine dosing interval.
[2] The pharmaceutical composition of [1], wherein the routine dosing interval is three to five weeks.
[3] The pharmaceutical composition of [1], wherein the routine dosing interval is four weeks.
[4] The pharmaceutical composition of any one of [1] to [3], wherein the dosing interval during the short-interval dosing period where the dose is administered multiple times at a shorter interval than the routine dosing interval is one to two weeks.
[5] The pharmaceutical composition of any one of [1] to [3], wherein the dosing interval during the short-interval dosing period where the dose is administered multiple times at a shorter interval than the routine dosing interval is two weeks.
[6] The pharmaceutical composition of any one of [1] to [5], wherein the short-interval dosing period is four weeks from the initial administration.
[7] The pharmaceutical composition of any one of [1] to [6], wherein the routine dose is 50 mg to 800 mg per administration.
[8] The pharmaceutical composition of any one of [1] to [7], wherein the routine dose is 120 mg per administration.
[9] The pharmaceutical composition of any one of [1] to [8], wherein the IL-6 inhibitor is an IL-6 receptor antibody.
[10] The pharmaceutical composition of [9], wherein the IL-6 receptor antibody is a chimeric antibody, a humanized antibody, or a human antibody.
[11] The pharmaceutical composition of [9], wherein the IL-6 receptor antibody comprises a heavy-chain variable region having the sequence of SEQ ID NO: 1 and a light-chain variable region having the sequence of SEQ ID NO: 2.
[12] The pharmaceutical composition of [9], wherein the IL-6 receptor antibody comprises a heavy chain having the sequence of SEQ ID NO: 3 and a light chain having the sequence of SEQ ID NO: 4.
[13] The pharmaceutical composition of [9], wherein the IL-6 receptor antibody is SA237.
[14] The pharmaceutical composition of any one of [1] to [13], wherein the IL-6-related disease is rheumatoid arthritis, juvenile idiopathic arthritis, systemic-onset juvenile idiopathic arthritis, Castleman's disease, systemic lupus erythematosus (SLE), lupus nephritis, Crohn's disease, lymphoma, ulcerative colitis, anemia, vasculitis, Kawasaki disease, Still's disease, amyloidosis, multiple sclerosis, transplantation, age-related macular degeneration, ankylosing spondylitis, psoriasis, psoriatic arthritis, chronic obstructive pulmonary disease (COPD), IgA nephropathy, osteoarthritis, asthma, diabetic nephropathy, GVHD, endometriosis, hepatitis (NASH), myocardial infarction, arteriosclerosis, sepsis, osteoporosis, diabetes, multiple myeloma, prostate cancer, kidney cancer, B-cell non-Hodgkin's lymphoma, pancreatic cancer, lung cancer, esophageal cancer, colon cancer, cancer cachexia, cancer nerve invasion, myocardial infarction, myopic choroidal neovascularization, idiopathic choroidal neovascularization, uveitis, chronic thyroiditis, delayed hypersensitivity, contact dermatitis, atopic dermatitis, mesothelioma, polymyositis, dermatomyositis, panuveitis, anterior uveitis, intermediate uveitis, scleritis, keratitis, orbital inflammation, optic neuritis, diabetic retinopathy, proliferative vitreoretinopathy, dry eye, postoperative inflammation, neuromyelitis optica, myasthenia gravis, or pulmonary hypertension.
[15] The pharmaceutical composition of any one of [1] to [14], wherein the pharmaceutical composition is a formulation for subcutaneous administration.
[16] A method for treating an IL-6-related disease comprising administering an IL-6 inhibitor, wherein the IL-6 inhibitor is administered routinely after a short-interval dosing period where the same dose as the routine dose is administered multiple times at a shorter interval than the routine dosing interval.
[17] An IL-6 inhibitor for use in treating an IL-6-related disease, wherein the IL-6 inhibitor is administered routinely after a short-interval dosing period where the same dose as the routine dose is administered multiple times at a shorter interval than the routine dosing interval.
[18] Use of an IL-6 inhibitor for the manufacture of a medicament for the treatment of an IL-6-related disease, wherein the IL-6 inhibitor is administered routinely after a short-interval dosing period where the same dose as the routine dose is administered multiple times at a shorter interval than the routine dosing interval.

Effects of the Invention

The pharmaceutical composition or regimen of the present invention can solve the immunogenic problem of anti-drug antibody generation, and provide a pharmaceutical composition with less patient burden since it does not expose the patient to high doses.

BRIEF DESCRIPTION OF THE DRAWINGS

FIG. 1a shows changes in the SA237 concentration during the primary evaluation period, FIG. 1b shows changes in the SA237 concentration during the extension period, and FIG. 1c shows changes in the serum SA237 concentration up to week 8.

FIG. 2a shows changes in the sIL-6R concentration during the primary evaluation period, and FIG. 2b shows change in the serum sIL-6R concentration during the extension period.

FIG. 3a shows changes in the CRP concentration during the primary evaluation period, and FIG. 3b shows changes in the CRP concentration during the extension period.

FIG. 4 is a table illustrating an observation and testing schedule for the primary evaluation period.

FIG. 5 is a table illustrating an observation and testing schedule for the extension period and follow-up period.

MODE FOR CARRYING OUT THE INVENTION

Figure 1:
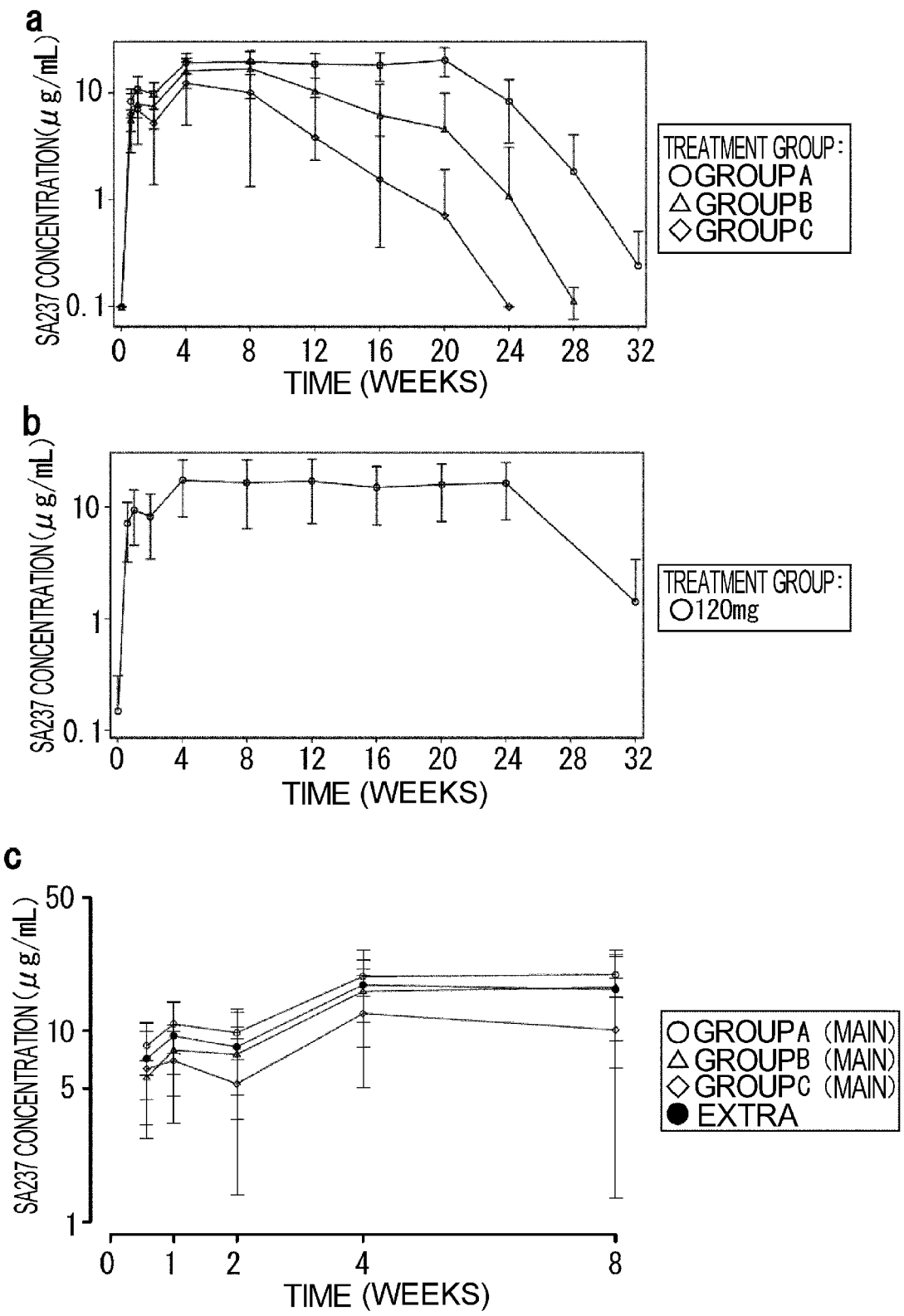
FIG. 1 indicates changes in the mean value (and standard deviation) of the serum SA237 concentration.

Herein below, the present invention will be described in detail.

The present invention relates to pharmaceutical compositions or dosage regimen to be used in the treatment of IL-6-related diseases.

"IL-6 inhibitors" of the present invention are substances that block signal transduction by IL-6, and inhibit the biological activities of IL-6. IL-6 inhibitors are preferably substances that have inhibitory effects against binding to any one of IL-6, IL-6 receptor, and gp130.

Examples of an IL-6 inhibitor of the present invention include, but are not particularly limited to, anti-IL-6 antibodies, anti-IL-6 receptor antibodies, anti-gp130 antibodies, IL-6 variants, soluble IL-6 receptor variants, or partial peptides of IL-6 or IL-6 receptor, and low-molecular-weight substances showing a similar activity. Examples of an IL-6 inhibitor of the present invention may be preferably IL-6 receptor-recognizing antibodies.

The origin of the antibodies of the present invention is not particularly limited, but it is preferably a mammal and more preferably human.

An anti-IL-6 antibody used in the present invention can be obtained as either a polyclonal or monoclonal antibody using known methods. A monoclonal antibody derived from a mammal is particularly preferred for the anti-IL-6 antibody used in the present invention The monoclonal antibodies derived from a mammal include those produced by a hybridoma and those produced by a host transformed with an expression vector containing an antibody gene using genetic engineering methods. By binding to IL-6, this antibody inhibits the binding of IL-6 to an IL-6 receptor, and blocks transduction of the IL-6 biological activity into cells.

Examples of such an antibody include the MH166 antibody (Matsuda, T. et al., Eur. J. Immunol. (1988) 18, 951-956) and the SK2 antibody (Sato, K. et al., The abstracts of the 21st Annual Meeting of the Japanese Society for Immunology (1991) 21, 166).

Basically, hybridomas that produce an anti-IL-6 antibody can be produced using known techniques as below. Specifically, the hybridomas can be produced by performing immunization by a conventional immunization method using IL-6 as a sensitizing antigen, fusing the resulting immune cells with known parent cells by a conventional cell fusion method, and then screening for cells that produce monoclonal antibodies using a conventional screening method.

Specifically, anti-IL-6 antibodies can be produced as below. Human IL-6 to be used as a sensitizing antigen for obtaining antibodies can be obtained by, for example, using the IL-6 gene and/or amino acid sequences disclosed in Eur. J. Biochem (1987) 168, 543-550; J. Immunol. (1988)140, 1534-1541; and Agr. Biol. Chem. (1990)54, 2685-2688.

After an appropriate host cell is transformed with a known expression vector system inserted with an IL-6 gene sequence, the target IL-6 protein is purified from the inside of the host cell or from the culture supernatant using a known method. This purified IL-6 protein may be used as a sensitizing antigen. Alternatively, a fusion protein of the IL-6 protein and another protein may be used as a sensitizing antigen.

An anti-IL-6 receptor antibody used in the present invention can be obtained as either a polyclonal or monoclonal antibody using known methods. A monoclonal antibody derived from a mammal is particularly preferred for the anti-IL-6 receptor antibody used in the present invention. The monoclonal antibodies derived from a mammal include those produced by a hybridoma and those produced by a host transformed with an expression vector containing an antibody gene using genetic engineering methods. By binding to an IL-6 receptor, this antibody inhibits the binding of IL-6 to an IL-6 receptor, and blocks transduction of the IL-6 biological activity into cells.

Examples of such an antibody include the MR16-1 antibody (Tamura, T. et al. Proc. Natl. Acad. Sci. USA (1993) 90, 11924-11928), PM-1 antibody (Hirata, Y et al., J. Immunol. (1989) 143, 2900-2906), AUK12-20 antibody, AUK64-7 antibody, and AUK146-15 antibody (International Patent Application Publication No. WO 92-19759). Among them, the PM-1 antibody is listed as an example of a preferred monoclonal antibody against the human IL-6 receptor, and the MR16-1 antibody is listed an example of a preferred monoclonal antibody against the mouse IL-6 receptor.

Basically, hybridomas that produce an anti-IL-6 receptor monoclonal antibody can be produced using known techniques as below. Specifically, the hybridomas can be produced by performing immunization by a conventional immunization method using an IL-6 receptor as a sensitizing antigen, fusing the resulting immune cells with known parent cells by a conventional cell fusion method, and then screening for cells that produce monoclonal antibodies using a conventional screening method.

Specifically, anti-IL-6 receptor antibodies can be produced as below. A human IL-6 receptor or mouse IL-6 receptor to be used as a sensitizing antigen for obtaining antibodies can be obtained by, for example, using the IL-6 receptor gene and/or amino acid sequences respectively disclosed in European Patent Application Publication No. EP 325474 and Japanese Patent Application Kokai Publication No. (JP-A) H03-155795 (unexamined, published Japanese patent application).

There are two types of IL-6 receptor proteins: one expressed on the cell membrane and the other separated from the cell membrane (soluble IL-6 receptor) (Yasukawa, K. et al., J. Biochem. (1990) 108, 673-676). The soluble IL-6 receptor is essentially composed of the extracellular region of the IL-6 receptor bound to the cell membrane, and differs from the membrane-bound IL-6 receptor in that it lacks the transmembrane region or both the transmembrane and intracellular regions. Any IL-6 receptor may be employed as the IL-6 receptor protein, as long as it can be used as a sensitizing antigen for producing an anti-IL-6 receptor antibody to be used in the present invention.

After an appropriate host cell is transformed with a known expression vector system inserted with an IL-6 receptor gene sequence, the target IL-6 receptor protein is purified from the inside of the host cell or from the culture supernatant using a known method. This purified IL-6 receptor protein may be used as a sensitizing antigen. Alternatively, a cell expressing the IL-6 receptor or a fusion protein of the IL-6 receptor protein and another protein may be used as a sensitizing antigen.

An anti-gp130 antibody used in the present invention can be obtained as either a polyclonal or monoclonal antibody using known methods. A monoclonal antibody derived from a mammal is particularly preferred for the anti-gp130 antibody used in the present invention. The monoclonal antibodies derived from a mammal include those produced by a hybridoma and those produced by a host transformed with an expression vector containing an antibody gene using a genetic engineering method. By binding to gp130, this antibody inhibits the binding of an IL-6/IL-6-receptor complex to gp130, and blocks transduction of the IL-6 biological activity into cells.

Examples of such an antibody include the AM64 antibody (JP-A (Kokai) H03-219894), 4B11 and 2H4 antibodies (U.S. Pat. No. 5,571,513), and the B-S12 and B-P8 antibodies (JP-A (Kokai) H08-291199).

Basically, hybridomas that produce an anti-gp130 monoclonal antibody can be produced using known techniques as below. Specifically, the hybridomas can be produced by performing immunization by a conventional immunization method using gp130 as a sensitizing antigen, fusing the resulting immune cells with known parent cells by a conventional cell fusion method, and then screening for cells that produce monoclonal antibodies using a conventional screening method.

Specifically, the monoclonal antibodies can be produced as below. For example, gp130 to be used as a sensitizing antigen for obtaining antibodies can be obtained by using the gp130 gene and/or amino acid sequences disclosed in European Patent Application Publication No. EP 411946.

After an appropriate host cell is transformed with a known expression vector system inserted with a gp130 gene sequence, the target gp130 protein is purified from the inside of the host cell or from the culture supernatant using a known method. This purified gp130 protein may be used as a sensitizing antigen. Alternatively, a gp130-expressing cell or a fusion protein of the gp130 protein and another protein may be used as a sensitizing antigen.

Mammals to be immunized with a sensitizing antigen are not particularly limited, but are preferably selected in consideration of the compatibility with parent cells used for cell fusion. Typically, rodents such as mice, rats, and hamsters are used.

Animals are immunized with a sensitizing antigen according to known methods. Typically, immunization is performed by, for example, intraperitoneal or subcutaneous injection of the sensitizing antigen to a mammal. Specifically, it is preferable to dilute or suspend the sensitizing antigen in phosphate-buffered saline (PBS), physiological saline, and such, to an appropriate volume, and mix it with an appropriate amount of a conventional adjuvant such as Freund's complete adjuvant if desired and emulsify, and then administer to the mammal every four to 21 days for several times. An appropriate carrier may also be used for immunization with the sensitizing antigen.

After immunizing the mammal in this manner, and confirming that the serum level of a desired antibody has increased, immunized cells are removed from the mammal and subjected to cell fusion. Spleen cells are particularly preferred as the immunized cells to be subjected to cell fusion.

Myeloma cells from mammals are used as parent cells to be fused with the immunized cells. So far, various known cell lines such as P3X63Ag8.653 (Kearney, J. F. et al., J. Immunol (1979) 123, 1548-1550), P3X63Ag8U.1 (Current Topics in Microbiology and Immunology (1978) 81, 1-7), NS-1 (Kohler, G. and Milstein, C., Eur. J. Immunol. (1976) 6, 511-519), MPC-11 (Margulies, D. H. et al., Cell (1976) 8, 405-415), SP2/0 (Shulman, M. et al., Nature (1978) 276, 269-270), F0 (de St. Groth, S. F. et al., J. Immunol. Methods (1980) 35, 1-21), S194 (Trowbridge, I. S., J. Exp. Med. (1978) 148, 313-323), and R210 (Galfre, G. et al., Nature (1979) 277, 131-133) are suitably used.

Basically, cell fusion of the aforementioned immune cells with myeloma cells can be performed according to known methods such as the method of Milstein et al. (Kohler, G. and Milstein, C., Methods Enzymol. (1981) 73, 3-46).

More specifically, the cell fusion is performed, for example, in a conventional nutrient culture medium in the presence of a cell fusion promoter. For example, polyethylene glycol (PEG) or Sendai virus (HVJ) is used as the fusion promoter, and if desired, an adjuvant such as dimethyl sulfoxide can be further added for use in improving the fusion efficiency.

The ratio of immune cells to myeloma cells used is preferably, for example, 1 to 10 immune cells for each myeloma cell. The culture medium used for the cell fusion is, for example, an RPMI1640 or MEM culture medium suitable for the proliferation of the myeloma cell lines. Other conventional culture media used for this type of cell culture can also be used. Furthermore, serum supplements such as fetal calf serum (FCS) can also be used in combination.

For cell fusion, the fusion cells (hybridomas) of interest are formed by thoroughly mixing predetermined amounts of the aforementioned immune cell and myeloma cell in the aforementioned culture medium, adding a PEG solution (for example, a solution of PEG with an average molecular weight of about 1,000 to 6,000) pre-heated to about 37° C., usually at a concentration of 30% to 60% (w/v), and then mixing them. Then, cell fusion agents and such that are unsuitable for the growth of hybridomas can be removed by repeating the operation of sequentially adding an appropriate culture medium and removing the supernatant by centrifugation.

The hybridomas are selected by culturing in a general selection culture medium, for example, the HAT culture medium (a culture medium containing hypoxanthine, aminopterin, and thymidine). Culturing in the HAT culture medium is continued for a sufficient period, generally from several days to several weeks, to kill cells other than the hybridomas of interest (unfused cells). Then, a standard limiting dilution method is performed to screen for and clone hybridomas that produce an antibody of interest.

Besides obtaining the hybridomas by immunizing non-human animals with an antigen, desired human antibodies having a binding activity to a desired antigen or antigen-expressing cell can be obtained by sensitizing a human lymphocyte with a desired antigen protein or antigen-expressing cell in vitro, and fusing the sensitized B lymphocyte with a human myeloma cell such as U266 (see, Japanese Patent Application Kokoku Publication No. (JP-B) H01-59878 (examined, approved Japanese patent application published for opposition)). Further, an antigen or antigen-expressing cell may be administered to a transgenic animal having a repertoire of human antibody genes, and then a desired human antibody may be obtained following the aforementioned method (see, International Patent Application Publication Nos. WO 93/12227, WO 92/03918, WO 94/02602, WO 94/25585, WO 96/34096, and WO 96/33735).

The hybridomas prepared as such that produce monoclonal antibodies can be subcultured in a conventional culture medium and stored in liquid nitrogen for a long period.

To obtain monoclonal antibodies from the hybridomas, the following methods may be employed: culturing the hybridomas according to conventional methods and obtaining the antibodies as a culture supernatant or proliferating the hybridomas by administering them to a compatible mammal and obtaining the antibodies from ascites; and so on. The former method is suitable for obtaining antibodies with high purity, and the latter is suitable for large-scale antibody production.

For example, hybridomas that produce anti-IL-6 receptor antibodies can be prepared by the method disclosed in JP-A (Kokai) H03-139293. Such a preparation can be carried out by injecting hybridomas that produce PM-1 antibodies into the abdominal cavity of a BALB/c mouse, obtaining ascites, and then purifying the PM-1 antibodies from the ascites; or by culturing the hybridomas in an appropriate medium (such as an RPMI 1640 medium containing 10% fetal bovine serum, and 5% BM-Condimed H1 (Boehringer Mannheim); the hybridoma SFM medium (GIBCO-BRL); or the PFHM-II medium (GIBCO-BRL)) and then purifying the PM-1 antibodies from the culture supernatant.

Recombinant antibodies can be used as the monoclonal antibodies of the present invention, wherein the recombinant antibodies are produced using genetic recombination techniques by cloning an antibody gene from a hybridoma, inserting the gene into an appropriate vector, and then introducing the vector into a host (see, for example, Borrebaeck, C. A. K. and Larrick, J. W., THERAPEUTIC MONOCLONAL ANTIBODIES, Published in the United Kingdom by MACMILLAN PUBLISHERS LTD, 1990).

More specifically, mRNAs coding for antibody variable (V) regions are isolated from cells that produce antibodies of interest, such as hybridomas. mRNAs can be isolated by preparing total RNAs according to known methods, such as the guanidine ultracentrifugation method (Chirgwin, J. M. et al., Biochemistry (1979) 18, 5294-5299) and the AGPC method (Chomczynski, P. et al., Anal. Biochem. (1987) 162, 156-159), and preparing mRNAs using an mRNA Purification Kit (Pharmacia) and such. Alternatively, mRNAs can be directly prepared using the QuickPrep mRNA Purification Kit (Pharmacia).

cDNAs of the antibody V regions are synthesized from the obtained mRNAs using reverse transcriptase. cDNAs may be synthesized using the AMV Reverse Transcriptase First-strand cDNA Synthesis Kit and such. Further, to synthesize and amplify the cDNAs, the 5'-RACE method (Frohman, M. A. et al., Proc. Natl. Acad. Sci. USA (1988) 85, 8998-9002; Belyaysky, A. et al., Nucleic Acids Res. (1989) 17, 2919-2932) using 5'-Ampli FINDER RACE Kit (Clontech) and PCR may be used. A DNA fragment of interest is purified from the obtained PCR products and then ligated with a vector DNA. Then, a recombinant vector is prepared by using the above, and introduced into *Escherichia coli* and such, and then its colonies are selected to prepare a desired recombinant vector. The nucleotide sequence of the DNA of interest is confirmed by a known method such as the dideoxy method.

When a DNA encoding the V region of the antibody of interest is obtained, the DNA is ligated with a DNA encoding the constant region (C region) of a desired antibody, and inserted into an expression vector. Alternatively, a DNA encoding an antibody V region may be inserted into an expression vector comprising a DNA of an antibody C region.

To produce an antibody to be used in the present invention, an antibody gene is inserted into an expression vector such that it is expressed under the control of an expression-regulating region such as an enhancer and promoter, as described below. Then, the antibody can be expressed by transforming a host cell with this expression vector.

In the present invention, artificially modified recombinant antibodies, for example, chimeric antibodies, humanized antibodies, or human antibodies can be used, for example, to reduce heteroantigenicity against humans. These modified antibodies can be prepared using known methods.

A chimeric antibody can be obtained by ligating a DNA encoding an antibody V region obtained as above with a DNA encoding a human antibody C region, inserting it into an expression vector, and introducing the vector into a host to produce the chimeric antibody (see, European Patent Application Publication No. EP 125023; International Patent Application Publication No. WO 92-19759). This known method can be used to obtain chimeric antibodies useful for the present invention.

Humanized antibodies are also referred to as reshaped human antibodies or antibodies made into the human type. They are produced by transplanting the complementarity determining regions (CDRs) of an antibody from a non-human mammal (for example, a mouse) into the CDRs of a human antibody. General methods for this gene recombination are also known (see, European Patent Application Publication No. EP 125023, International Patent Application Publication No. WO 92-19759).

More specifically, DNA sequences designed to ligate the CDRs of a mouse antibody with the framework regions (FRs) of a human antibody are synthesized by PCR from several oligonucleotides produced to contain overlapping portions at their termini. The obtained DNA is ligated with a DNA encoding a human antibody C region and inserted into an expression vector, and the expression vector is introduced into a host to produce the humanized antibody (see, European Patent Application Publication No. EP 239400, International Patent Application Publication No. WO 92-19759).

Human antibody FRs to be ligated via the CDRs are selected so that the CDRs form satisfactory antigen binding sites. The amino acid(s) within the framework regions of the antibody variable regions may be substituted as necessary so that the CDRs of the reshaped human antibody form appropriate antigen binding sites (Sato, K. et al., Cancer Res. (1993) 53, 851-856).

Human antibody C regions are used for the chimeric and humanized antibodies. Examples of human antibody C regions include Cγ, and for example, Cγ1, Cγ2, Cγ3, or Cγ4 may be used. Furthermore, to improve the stability of the antibodies or their production, the human antibody C regions may be modified.

Chimeric antibodies are composed of the variable region of an antibody derived from a non-human mammal and the C region derived from a human antibody; and humanized antibodies are composed of the CDRs of an antibody derived from a non-human mammal and the framework regions and C regions derived from a human antibody. Their antigenicity in the human body is reduced, and thus they are useful as antibodies for use in the present invention.

Preferred specific examples of humanized antibodies for use in the present invention include a humanized PM-1 antibody (see, International Patent Application Publication No. WO 92-19759).

Furthermore, in addition to the aforementioned methods for obtaining human antibodies, techniques for obtaining human antibodies by panning using a human antibody library are also known. For example, the variable region of a human antibody can be expressed on a phage surface as a single chain antibody (scFv) by using the phage display method, and antigen-binding phages can then be selected. By analyzing the genes of the selected phages, the DNA sequence encoding the variable region of the human antibody which binds to the antigen can be determined. Once the DNA sequence of an scFv which binds to the antigen is revealed, an appropriate expression vector comprising the sequence can be prepared to obtain a human antibody. These methods are already known, and the publications, WO 92/01047, WO 92/20791, WO93/06213, WO 93/11236, WO 93/19172, WO 95/01438, and WO 95/15388, can be used as references.

The antibody gene constructed as described above can be expressed according to known methods. When a mammalian cell is used, the antibody gene can be expressed by using a DNA in which a commonly used effective promoter gene, the antibody gene to be expressed, and a poly A signal on the 3' side (downstream) of the antibody gene are operatively linked together, or by using a vector comprising the DNA. Examples of a promoter/enhancer include the human cytomegalovirus immediate early promoter/enhancer.

Furthermore, other promoters/enhancers that can be used for expressing the antibodies for use in the present invention include viral promoters/enhancers from retroviruses, polyoma viruses, adenoviruses, simian virus 40 (SV40), and such; and mammalian cell-derived promoters/enhancers such as human elongation factor 1α (HEF1α).

The expression can be easily performed, for example, by following the method in Mulligan et al. (Mulligan, R. C. et al., Nature (1979) 277, 108-114) when using the SV40 promoter/enhancer, or by following the method in Mizushima et al. (Mizushima, S. and Nagata S., Nucleic Acids Res. (1990) 18, 5322) when using the HEF1α promoter/enhancer.

When E. coli is used, the antibody gene can be expressed by operatively linking a commonly used effective promoter gene, a signal sequence for antibody secretion, and the antibody gene to be expressed. Examples of the promoter include a lacZ promoter and an araB promoter. A lacZ promoter can be used according to the method of Ward et al. (Ward, E. S. et al., Nature (1989) 341, 544-546; Ward, E. S. et al., FASEB J. (1992) 6, 2422-2427); and an araB promoter can be used according to the method of Better et al. (Better, M. et al., Science (1988) 240, 1041-1043).

When the antibody is produced into the periplasm of E. coli, the pel B signal sequence (Lei, S. P. et al., J. Bacteriol. (1987) 169, 4379-4383) may be used as a signal sequence for antibody secretion. The antibody produced into the periplasm is isolated, and then appropriately refolded the antibody structure to be used (see, for example, WO 96/30394).

As the replication origin, those derived from SV40, polyoma virus, adenovirus, bovine papilloma virus (BPV) and such may be used. In addition, to increase the gene copy number in a host cell system, the expression vector may comprise the aminoglycoside phosphotransferase (APH) gene, thymidine kinase (TK) gene, E. coli xanthine-guanine phosphoribosyltransferase (Ecogpt) gene, dihydrofolate reductase (dhfr) gene, and such, as a selection marker.

Any production system may be used to prepare the antibodies for use in the present invention. The production systems for antibody preparation include in vitro and in vivo production systems. In vitro production systems include those using eukaryotic cells or those using prokaryotic cells.

When eukaryotic cells are used, the production systems include those using animal cells, plant cells, or fungal cells. Such animal cells include (1) mammalian cells such as CHO, COS, myeloma, baby hamster kidney (BHK), HeLa, and Vero; (2) amphibian cells such as Xenopus oocytes; and (3) insect cells such as sf9, sf21, and Tn5. Known plant cells include cells derived from Nicotiana tabacum, which may be cultured in callus. Known fungal cells include yeasts such as Saccharomyces (e.g., Saccaromyces cerevisiae) and mold fungi such as Aspergillus (e.g., Aspergillus niger).

When prokaryotic cells are used, production systems include those using bacterial cells. Known bacterial cells include E. coli and Bacillus subtilis.

Antibodies can be obtained by introducing the antibody gene of interest into these cells by transformation, and then culturing the transformed cells in vitro. Cells are cultured according to known methods. For example, DMEM, MEM, RPMI 1640, or IMDM may be used as the culture medium, and serum supplements such as fetal calf serum (FCS) may be used in combination. Alternatively, cells introduced with the antibody gene may be transferred into the abdominal cavity and such of an animal to produce the antibodies in vivo.

Meanwhile, in vivo production systems include those using animals or those using plants. When using animals, production systems include those using mammals or insects.

Mammals that can be used include goats, pigs, sheep, mice, and bovines (Vicki Glaser, SPECTRUM Biotechnology Applications, 1993). Further, insects that can be used include silkworms. When using plants, tobacco and such may be used.

An antibody gene is introduced into these animals or plants, and the antibodies are produced in the body of the animals or plants and then recovered. For example, an antibody gene can be prepared as a fusion gene by inserting it into the middle of a gene encoding a protein uniquely produced into milk, such as goat β casein. DNA fragments comprising the fusion gene, which includes the inserted antibody gene, are injected into goat embryos, and the embryos are introduced into female goats. The desired antibodies are obtained from milk produced by transgenic goats born from the goats that received the embryos, or their progenies. When appropriate, the transgenic goats may be given hormones to increase the volume of milk containing the desired antibodies that they produce (Ebert, K. M. et al., Bio/Technology (1994) 12, 699-702).

When silkworms are used, the silkworms are infected with a baculovirus inserted with the antibody gene of interest, and the desired antibodies are obtained from the body fluids of these silkworms (Maeda, S. et al., Nature (1985) 315, 592-594). Moreover, when tobacco is used, the antibody gene of interest is inserted into a plant expression vector such as pMON530, and the vector is introduced into bacteria such as Agrobacterium tumefaciens. This bacterium is used to infect tobacco such as Nicotiana tabacum, and then the desired antibody is obtained from the leaves of this tobacco (Julian, K.-C. Ma et al., Eur. J. Immunol. (1994) 24, 131-138).

When producing antibodies using in vitro or in vivo production systems as described above, DNAs encoding an antibody heavy chain (H chain) and light chain (L chain) may be inserted into separate expression vectors, and a host is then co-transformed with the vectors. Alternatively, the H chain-encoding DNA and L chain-encoding DNA may be inserted into a single expression vector for transforming a host (see International Patent Application Publication No. WO 94-11523).

The antibodies used in the present invention may be antibody fragments or modified products thereof, as long as they can be suitably used in the present invention. For example, antibody fragments include Fab, F(ab')2, Fv, and single chain Fv (scFv) in which the Fvs of the H and L chains are linked via an appropriate linker.

Specifically, the antibody fragments are produced by treating antibodies with enzymes such as papain or pepsin, or alternatively, by constructing genes encoding these antibody fragments and introducing them into expression vectors, and then expressing the vectors in appropriate host cells (see, for example, Co, M. S. et al., J. Immunol. (1994) 152, 2968-2976; Better, M. & Horwitz, A. H., Methods in Enzymology (1989) 178, 476-496; Plueckthun, A. & Skerra, A., Methods in Enzymology (1989) 178, 497-515; Lamoyi, E., Methods in Enzymology (1989) 121, 652-663; Rousseaux, J. et al., Methods in Enzymology (1989) 121, 663-666; and Bird, R. E. et al., TIBTECH (1991) 9, 132-137).

An scFv can be obtained by linking the H-chain V region and the L-chain V region of an antibody. In this scFv, the H-chain V region and the L-chain V region are linked via a linker, preferably via a peptide linker (Huston, J. S. et al., Proc. Natl. Acad. Sci. USA (1988) 85, 5879-5883). The V regions of the H and L chains in an scFv may be derived from any of the antibodies described above. Peptide linkers for linking the V regions include, for example, an arbitrary single chain peptide consisting of 12 to 19 amino acid residues.

A DNA encoding an scFv can be obtained by amplifying a DNA portion that encodes the desired amino acid sequence in template sequences with PCR using a primer pair which defines the termini of the portion, wherein a DNA encoding an H chain or an H-chain V region and a DNA encoding an L chain or an L-chain V region of the aforementioned antibodies are used as the templates, and then further amplifying the amplified DNA portion with a DNA that encodes a peptide linker portion and a primer pair that defines both ends of the linker so that it may be linked to each of the H and L chains.

Once an scFv-encoding DNA has been prepared, an expression vector comprising the DNA and a host transformed with the expression vector can be obtained according to conventional methods. In addition, an scFv can be obtained according to conventional methods by using the host.

Similar to the above, the antibody fragments can be produced by obtaining their genes, expressing them, and then using a host. An "antibody" as used herein encompasses such antibody fragments.

Antibodies bound to various molecules such as polyethylene glycol (PEG) may also be used as modified antibodies. An "antibody" as used herein encompasses such modified antibodies. These modified antibodies can be obtained by chemically modifying the obtained antibodies. Such methods are already established in the art.

Antibodies produced and expressed as above can be isolated from the inside or outside of the cells or from the hosts, and then purified to homogeneity. The antibodies for use in the present invention can be isolated and purified by affinity chromatography. Columns used for the affinity chromatography include protein A columns and protein G columns. Carriers used for the protein A columns include HyperD, POROS, and Sepharose F.F. Other methods used for the isolation and/or purification of ordinary proteins may be used without limitation.

For example, the antibodies used for the present invention may be isolated and purified by appropriately selecting and combining chromatographies other than the above-described affinity chromatography, filtration, ultrafiltration, salting-out, dialysis, and such. Examples of chromatographies include ion-exchange chromatography, hydrophobic chromatography, and gel filtration. These chromatographies can be applied to high performance liquid chromatography (HPLC). Alternatively, reverse phase HPLC may be used.

The concentration of the antibodies obtained as above can be determined by absorbance measurement, ELISA, and such. Specifically, when using absorbance measurement, the concentration can be determined by appropriately diluting the antibody solution with PBS(−), measuring its absorbance at 280 nm, and calculating the concentration by using the conversion factor 1.35 OD/1 mg/ml. Alternatively, when using ELISA, the concentration can be determined as below. Specifically, 100 µl of goat anti-human IgG (TAG) diluted to 1 µg/ml with 0.1 M bicarbonate buffer (pH 9.6) is added to a 96-well plate (Nunc) and incubated overnight at 4° C. to immobilize the antibody. After blocking, 100 µl of an appropriately diluted antibody to be used in the present invention or an appropriately diluted sample comprising the antibody, or human IgG (CAPPEL) as a standard is added, and the plate is incubated for one hour at room temperature. After washing, 100 µl of 5,000× diluted alkaline phosphatase-labeled anti-human IgG (BIO SOURCE) is added, and the plate is incubated for one hour at room temperature. After another wash, the substrate solution is added, the plate is incubated, and absorbance at 405 nm is measured using Microplate Reader Model 3550 (Bio-Rad) to calculate the concentration of the antibody of interest.

The IL-6 variants used in the present invention are substances that have binding activity to an IL-6 receptor and which do not transmit IL-6 biological activity. That is, the IL-6 variants compete with IL-6 for binding to an IL-6 receptor, but do not transmit IL-6 biological activity, and thus block IL-6-mediated signal transduction.

The IL-6 variants are produced by introducing mutation(s) by substituting amino acid residue(s) in the amino acid sequence of IL-6. Any IL-6 from which the IL-6 variant is derived can be used, but human IL-6 is preferred, considering antigenicity and such.

More specifically, the amino acid substitutions are performed by predicting the secondary structure of IL-6 from the IL-6 amino acid sequence using known molecular modeling programs such as WHATIF (Vriend et al., J. Mol. Graphics (1990) 8, 52-56), and further assessing the influence of the substituted amino acid residue(s) on the whole molecule. After determining the appropriate amino acid residue(s) to be substituted, mutation(s) are introduced by a commonly performed PCR method using a vector comprising a nucleotide sequence encoding a human IL-6 gene as a template to cause amino acid substitution(s), and the gene encoding the IL-6 variant is thereby obtained. If needed, this gene is inserted into an appropriate expression vector, and the IL-6 variant can be obtained according to the aforementioned methods for expression, production, and purification of recombinant antibodies.

Specific examples of the IL-6 variants are disclosed in Brakenhoff et al., J. Biol. Chem. (1994) 269, 86-93; Savino et al., EMBO J. (1994) 13, 1357-1367; WO 96-18648; and WO 96-17869.

Partial peptides of IL-6 or the IL-6 receptor to be used in the present invention are substances that have a binding activity to the IL-6 receptor or IL-6, respectively, and which do not transmit the IL-6 biological activities. That is, the partial peptides of IL-6 or the IL-6 receptor bind to and capture the IL-6 receptor or IL-6, and thereby specifically inhibit binding of IL-6 to the IL-6 receptor. As a result, the IL-6 biological activities are not transmitted, and thus, IL-6-mediated signal transduction is blocked.

Partial peptides of IL-6 or the IL-6 receptor are peptides that are composed of the whole amino acid sequence of the region of the IL-6 or IL-6 receptor amino acid sequence or a part thereof involved in the binding between IL-6 and the IL-6 receptor. Such peptides are usually composed of 10 to 80, preferably 20 to 50, more preferably 20 to 40 amino acid residues.

Partial peptides of IL-6 or the IL-6 receptor can be produced by specifying the region of the IL-6 or IL-6 receptor amino acid sequence involved in the binding between IL-6 and the IL-6 receptor, and applying generally known methods such as genetic engineering techniques and peptide synthesis methods to the whole amino acid sequence of the specified region or a portion thereof.

To prepare a partial peptide of IL-6 or an IL-6 receptor by genetic engineering methods, a DNA sequence encoding the desired peptide is inserted into an expression vector, and then the peptide can be obtained by applying the aforementioned methods for expressing, producing, and purifying recombinant antibodies.

To produce a partial peptide of IL-6 or an IL-6 receptor by peptide synthesis methods, generally used peptide synthesis methods such as solid phase synthesis methods and liquid phase synthesis methods may be used.

Specifically, the peptides can be synthesized according to the method described in "The sequel of Development of Pharmaceuticals (Zoku Iyakuhin no Kaihatsu), Vol. 14, Peptide Synthesis (ed. Haruaki Yajima, 1991, Hirokawa Shoten)". As a solid phase synthesis method, the following method and such can be employed: binding the amino acid corresponding to the C terminus of the peptide to be synthesized to a support that is insoluble in organic solvents, and then elongating the peptide strand by alternately repeating (1) the reaction of condensing amino acids whose α-amino groups and branch chain functional groups are protected with appropriate protecting groups, one at a time in a C terminus to N terminus direction; and (2) the reaction of removing the protecting groups from the α-amino groups of the resin-bound amino acids or peptides. Solid-phase peptide synthesis is broadly classified into the Boc method and the Fmoc method, depending on the type of protecting groups used.

After synthesizing the peptide of interest as above, deprotection reaction and cleavage reaction of the peptide strand from the support are carried out. For the cleavage reaction of the peptide strand, hydrogen fluoride or trifluoromethane sulfonic acid is generally used for the Boc method, and TFA is generally used for the Fmoc method. In the Boc method, for example, the protected peptide-bound resin is treated with hydrogen fluoride in the presence of anisole. Then, the peptide is recovered by removing the protecting groups and cleaving the peptide from its support. By freeze-drying the recovered peptide, a crude peptide can be obtained. In the Fmoc method, the deprotection reaction and the cleavage reaction of the peptide strand from the support can be performed in TFA and such by operations similar to those described above.

The obtained crude peptides can be separated and purified by applying HPLC. Elution may be performed under optimum conditions using a water-acetonitrile solvent system, which is generally used for protein purification. The fractions corresponding to the peaks of the obtained chromatographic profile are collected and freeze-dried. Peptide fractions purified this way are identified by molecular weight analysis via mass spectrum analysis, amino acid composition analysis, amino acid sequence analysis, and such.

Specific examples of the partial peptides of IL-6 and the IL-6 receptor are disclosed in JP-A (Kokai) H02-188600, JP-A (Kokai) H07-324097, JP-A (Kokai) H08-311098, and US Patent Publication No. US5210075.

The antibodies used in the present invention may be conjugate antibodies that are bound to various molecules such as polyethylene glycol (PEG), radioactive substances, and toxins. Such conjugate antibodies can be obtained by chemically modifying the obtained antibodies. Methods for antibody modification have been already established in this field. Accordingly, the term "antibody" as used herein encompasses such conjugate antibodies.

In the present invention, "IL-6-related disease" refers to a disease related to IL-6, and examples include rheumatoid arthritis, juvenile idiopathic arthritis, systemic-onset juvenile idiopathic arthritis, Castleman's disease, systemic lupus erythematosus (SLE), lupus nephritis, Crohn's disease, lymphoma, ulcerative colitis, anemia, vasculitis, Kawasaki disease, Still's disease, amyloidosis, multiple sclerosis, transplantation, age-related macular degeneration, ankylosing spondylitis, psoriasis, psoriatic arthritis, chronic obstructive pulmonary disease (COPD), IgA nephropathy, osteoarthritis, asthma, diabetic nephropathy, GVHD, endometriosis, hepatitis (NASH), myocardial infarction, arteriosclerosis, sepsis, osteoporosis, diabetes, multiple myeloma, prostate cancer, kidney cancer, B-cell non-Hodgkin's lymphoma, pancreatic cancer, lung cancer, esophageal cancer, colon cancer, cancer cachexia, cancer nerve invasion, myocardial infarction, myopic choroidal neovascularization, idiopathic choroidal neovascularization, uveitis, chronic thyroiditis, delayed hypersensitivity, contact dermatitis, atopic dermatitis, mesothelioma, polymyositis, dermatomyositis, panuveitis, anterior uveitis, intermediate uveitis, scleritis, keratitis, orbital inflammation, optic neuritis, diabetic retinopathy, proliferative vitreoretinopathy, dry eye, post-operative inflammation, neuromyelitis optica, myasthenia gravis, and pulmonary hypertension.

In the present invention, "routine dosing interval" refers to a dosing interval generally used for the above-mentioned pharmaceuticals (pharmaceutical compositions of the present invention), for example, a dosing interval for routine administration that may be described in a package insert as "subsequent doses should be administered at four-week intervals" and such. The routine dosing interval in the present invention is not particularly limited, but examples include one day to 24 weeks, preferably two weeks to eight weeks, more preferably three to five weeks, and even more preferably four weeks. The routine dosing intervals may have a certain range.

In the present invention, "routine dose" is a dose commonly used for the above-mentioned pharmaceuticals (pharmaceutical compositions of the present invention), for example, a generally administered dose that may be described in a package insert as "generally, a single dose is 8 mg per kg body weight". The routine dose in the present invention is not particularly limited, but the dose per administration may be, for example, two to 20 mg IL-6 inhibitor per kg body weight (2-20 mg/kg) or 50 mg to 800 mg IL-6 inhibitor, preferably two to eight mg IL-6 inhibitor per kg body weight (2-8 mg/kg) or 80 to 160 mg IL-6 inhibitor, or more preferably 8 mg IL-6 inhibitor per kg body weight (8 mg/kg) or 120 mg IL-6 inhibitor.

In the present invention, "short-interval dosing period" refers to an administration period for inducing immunological tolerance against drugs (pharmaceutical compositions of the present invention) to suppress the generation of anti-drug antibodies due to immunogenicity. The short-interval dosing period in the present invention refers to a period where the same dose as the routine dose is administered multiple times at a shorter interval than the routine dosing interval. Although the short-interval period is not particularly limited as long as it is a period where immunological tolerance is induced, the period is preferably one to eight weeks from the initial administration, and more preferably four weeks from the initial administration. "The same dose as the routine dose" includes doses that provide the same blood concentration of IL-6 inhibitor as a routine dose. "Shorter interval than the routine dosing interval" is not particularly limited as long as it is shorter than a routine dosing interval, and is preferably one half of a routine dosing interval, for example, two weeks when the routine dosing interval is four weeks. For example, the short-interval dosing period may have a certain range such as one to two weeks. "(Being) administered multiple times" refers to two or more administrations including the initial administration, and is preferably two to five administrations including the initial administration, more preferably three administrations including the initial administration. Whether immunological tolerance has been induced can be determined by observing whether the generation of anti-drug antibodies is suppressed.

"Routine administration" in the present invention refers to an administration commonly used for the above-mentioned pharmaceuticals (pharmaceutical compositions of the present invention), for example, an administration at the above-described "routine dose" and "routine dosing interval".

Preferred examples of an "IL-6 receptor antibody" of the present invention include tocilizumab which is a humanized anti-IL-6 receptor IgG1 antibody, and humanized anti-IL-6 receptor antibodies produced by modifying the variable and constant regions of tocilizumab, specifically, an antibody containing a heavy-chain variable region comprising the sequence of SEQ ID NO: 1 and a light-chain variable region comprising the sequence of SEQ ID NO: 2. A more preferable example is an antibody containing a heavy chain comprising the sequence of SEQ ID NO: 3 (heavy chain of SA237) and a light chain comprising the sequence of SEQ ID NO: 4 (light chain of SA237). SA237 is particularly preferred.

Such antibodies can be obtained according to the methods described in WO2010/035769, WO2010/107108, WO2010/106812, and such. Specifically, antibodies can be produced using genetic recombination techniques known to those skilled in the art, based on the sequence of the above-mentioned IL-6 receptor antibody (see, for example, Borrebaeck C A K and Larrick J W, THERAPEUTIC MONOCLONAL ANTIBODIES, Published in the United Kingdom by MACMILLAN PUBLISHERS LTD, 1990). A recombinant antibody can be obtained by cloning a DNA encoding the antibody from a hybridoma or an antibody-producing cell such as an antibody-producing sensitized lymphocyte, inserting the DNA into an appropriate vector, and introducing the vector into a host (host cell) to produce the antibody.

Such antibodies can be isolated and purified using isolation and purification methods conventionally used for antibody purification, without limitation. For example, the antibodies can be isolated and purified by appropriately selecting and combining column chromatography, filtration, ultrafiltration, salting-out, solvent precipitation, solvent extraction, distillation, immunoprecipitation, SDS-polyacrylamide gel electrophoresis, isoelectric focusing, dialysis, recrystallization, and such.

In the present invention, the routine administration period starts from the final administration of the short-interval dosing period. More specifically, the final administration in the short-interval dosing period is followed by a routine dosing interval, and then the first administration in the routine administration period is carried out.

The pharmaceutical composition of the present invention is preferably a pharmaceutical composition in which the same dose of an IL-6 inhibitor as the routine dose is administered two to five times with one to three-week intervals from the initial administration in the short-interval dosing period, and then the IL-6 inhibitor is administered with two to eight-week intervals starting from the final administration in the short-interval dosing period using a routine dose of 50 mg to 800 mg per administration; or more preferably a pharmaceutical composition in which SA237 is administered three times at the same dose as the routine dose with two-week intervals from the initial administration in the short-interval dosing period (that is, at week 0, week 2, and week 4), and then SA237 is administered routinely with eight-week intervals starting from the final administration in the short-interval dosing period (that is, at week 12, week 20, week 28 and so on with eight-week intervals, counting from the initial administration in the short-interval dosing period) using a routine dose of 120 mg per administration.

The preferred administration schedule for the IL-6 inhibitor can be adjusted, for example, by appropriately extending the administration interval by monitoring the conditions of the disease and changes in the blood test values.

Pharmaceutical compositions of the present invention used for therapeutic or preventive purposes can be formulated to produce freeze-dried formulations or solution formulations by mixing, if necessary, with suitable pharmaceutically acceptable carriers, vehicles, and such. The suitable pharmaceutically acceptable carriers and vehicles include, for example, sterilized water, physiological saline, stabilizers, excipients, antioxidants (such as ascorbic acid), buffers (such as phosphate, citrate, histidine, and other organic acids), antiseptics, surfactants (such as PEG and Tween), chelating agents (such as EDTA), and binders. Other low-molecular-weight polypeptides, proteins such as serum albumin, gelatin, and immunoglobulins, amino acids such as glycine, glutamine, asparagine, glutamic acid, aspartic acid, methionine, arginine, and lysine, sugars and carbohydrates such as polysaccharides and monosaccharides, and sugar alcohols such as mannitol and sorbitol may also be contained. When preparing an aqueous solution for injection, physiological saline and isotonic solutions comprising glucose and other adjuvants such as D-sorbitol, D-mannose, D-mannitol, and sodium chloride may be used; and appropriate solubilizers such as alcohol (for example, ethanol), polyalcohols (such as propylene glycol and PEG), and nonionic surfactants (such as polysorbate 80, polysorbate 20, poloxamer 188, and HCO-50) may be used in combination. By mixing hyaluronidase into the formulation, a larger fluid volume can be administered subcutaneously (Expert Opin. Drug Deliv. 2007 July; 4(4): 427-40). Furthermore, syringes may be prefilled with the pharmaceutical composition of the present invention. Solution formulations can be prepared according to the method described in WO2011/090088.

If necessary, the pharmaceutical compositions of the present invention may be encapsulated in microcapsules (e.g., those made of hydroxymethylcellulose, gelatin, and poly(methylmetacrylate)), or incorporated into colloidal drug delivery systems (e.g., liposomes, albumin microspheres, microemulsion, nanoparticles, and nanocapsules) (see, for example, "Remington's Pharmaceutical Science 16th edition", Oslo Ed. (1980)). Methods for preparing the pharmaceutical agents as controlled-release pharmaceutical agents are also known, and such methods may be applied to the pharmaceutical compositions of the present invention (Langer et al., J. Biomed. Mater. Res. 15: 267-277 (1981); Langer, Chemtech. 12: 98-105 (1982); U.S. Pat. No. 3,773, 919; European Patent Application Publication No. EP 58,481; Sidman et al., Biopolymers 22: 547-556 (1983); and EP 133,988).

The pharmaceutical composition of the present invention can be administered to a patient via any appropriate route. For example, it can be administered to a patient intravenously by bolus injection or by continuous infusion, intramuscularly, intraperitoneally, intracerebrospinally, transdermally, subcutaneously, intraarticularly, sublingually, intrasynovially, orally, by inhalation, locally, or externally, for a certain period of time. Intravenous administration or subcutaneous administration is preferred.

All prior art references cited herein are incorporated by reference into the present specification.

EXAMPLES

Herein below, the present invention will be specifically described with reference to the Examples, but it is not to be construed as being limited thereto.

Example 1

Preparation of IL-6 Inhibitors

SA237, the IL-6 receptor antibody described in the patent document, WO2010/035769 (an antibody containing a heavy chain having the sequence of SEQ ID NO: 26 of WO 2010/035769 (SEQ ID NO: 3 of the present specification) and a light chain having the sequence of SEQ ID NO: 29 of WO 2010/035769 (SEQ ID NO: 4 of the present specification) in WO2010/035769), was produced according to the description in the aforementioned patent document. The produced antibody was used to prepare formulations for subcutaneous administration by the method in the patent document of WO2011/090088.

Example 2

Examination by Single Subcutaneous Administration to Japanese and Caucasian Healthy Adult Male Subjects (SA001JP)

Safety, tolerability, pharmacokinetics, and bioavailability of SA237 when administered subcutaneously to Japanese and Caucasian healthy adult male subjects were evaluated. In this study, SA237 was administered subcutaneously or intravenously by drip infusion to 48 Japanese individuals, and administered subcutaneously to 24 Caucasian individuals. The safety and tolerability at a single administration of SA237 were mostly satisfactory in 24 cases. The absolute bioavailability of SA237 for 60 mg and 120 mg subcutaneous administrations were 64.6% and 69.4%, respectively. Development of anti-SA237 antibodies was observed in 39 out of 72 subjects administered with SA237.

Example 3

Open-Label, Parallel-Group Comparative Study by Multiple Subcutaneous Administration to Japanese Rheumatoid Arthritis Patients (SA-105JP)

Patients fulfilling the following criteria were selected as the subjects:
(1) Diagnosed with rheumatoid arthritis (RA) according to the 1987 American College of Rheumatology (ACR) criteria;
(2) RA disease duration for six months or more;
(3) Showed a C-reactive protein (CRP) level above the upper limit of the laboratory reference range in a test performed within two weeks prior to initiating administration of the investigational medicinal product (IMP);
(4) Aged 20 years or older at the time of informed consent;
(5) Signed the informed consent form in person;
(6) Has not received treatment with methotrexate (MTX) later than or at 16 weeks prior to initiating administration of the IMP;
(7) Has not received treatment with leflunomide later than or at 12 weeks prior to initiating administration of the IMP (or later than or at four weeks prior to initiating administration of the investigational agent, if a standard cholestyramine treatment or drug elimination has been carried out with activated charcoal);
(8) Has not received treatment with DMARD or immunosuppressive agents other than those described above later than or at four weeks prior to initiating administration of the investigational agent; and
(9) Has not received treatment exceeding 10 mg per day as prednisolone equivalence, later than or at two weeks prior to initiating administration of the investigational agent.

The subjects were randomized into three groups (groups A, B, and C) according to the central registration method, and the open label, parallel-group comparative study was performed (see Table 1). The randomization was stratified by body weight. This clinical study comprises a primary evaluation period, an extension period, and a follow-up period.

In the primary evaluation period, 120 mg of SA237 was administered at week 0, week 2, and week 4; and 120 mg, 60 mg, and 30 mg of SA237 were administered to groups A, B, and C, respectively, from week 8 up to week 16 with four-week intervals. Thereafter, in principle, groups A, B, and C were observed up to weeks 32, 28, and 24, respectively, at which time the serum SA237 concentrations were expected to be undetectable level in each of the groups (the observation included anti-SA237 antibody measurements).

In the extension period, 120 mg of SA237 was administered at week 0, week 2, and week 4; and 120 mg of SA237 was administered from week 8 up to 20 weeks with four-week intervals, and observation was continued up to week 32.

The test drug was in the form of a vial filled with 1.0 mL of a solution containing 120 mg of SA237. The solution contained L-histidine, L-arginine, L-aspartic acid, and polyoxyethylene (160) polyoxypropylene (30) glycol as additives, and was adjusted to pH 5.5 to 6.5. In principle, the drug was subcutaneously administered to the abdominal area.

TABLE 1

NUMBER OF CASES

|  | GROUP A | GROUP B | GROUP C | TOTAL |
| --- | --- | --- | --- | --- |
| NUMBER OF TARGETED CASES | 10 | 10 | 10 | 30 |
| NUMBER OF REGISTERED CASES | 11 | 11 | 11 | 33 |
| ALLOCATED CASES | 11 | 11 | 11 | 33 |
| ADMINISTERED CASES | 11 | 11 | 11 | 33 |
| CASES SUBJECTED TO PHARMACOKINETIC ANALYSIS | 11 | 11 | 11 | 33 |
| POPULATION SUBJECTED TO EFFECTIVENESS ANALYSIS (FULL ANALYSIS SET (FAS)) | 11 | 11 | 11 | 33 |
| POPULATION SUBJECTED TO EFFECTIVENESS ANALYSIS (PER PROTOCOL SET (PPS)) | 9 | 9 | 9 | 27 |
| CASES SUBJECTED TO SAFETY ANALYSIS | 11 | 11 | 11 | 33 |

In the pharmacokinetic and pharmacodynamic evaluations, and in the examination of efficacy (in the full analysis set (FAS)) and safety of repeatedly administering SA237 to RA patients, the background of the subjects in the respective 11-case groups (33 cases in total) subjected to each analysis was 59.0 to 65.0-years of age (median range for each of the groups; the same applies hereafter) and 50.30 to 57.90 kg body weight. The percentage of female in each group was high, and was 81.8% in group A (9/11 cases), 90.9% in group B (10/11 cases), and 63.6% in group C (7/11 cases). Subjects who received the investigational agent until the end of the primary evaluation period were 10/11 cases (90.9%) in group A, 10/11 cases (90.9%) in group B, and 9/11 cases (81.8%) in group C; and subjects who could be observed for the whole duration (the primary evaluation period and the extension period) were 10/11 cases (90.9%) in group A, 7/11 cases (63.6%) in group B, and 7/11 cases (63.6%) in group C.

(1) Pharmacokinetics

Evaluation method: Observation and testing were carried out according to the tables shown in FIGS. 4 and 5. Where it is not particularly specified, evaluations were carried out prior to administration of the investigational agent. Even if the defined primary evaluation period had not reached completion, when the evaluation was carried out on or after the day of initial administration of the extension period, the subsequent observation and testing for the primary evaluation period were determined to be unnecessary. The testing periods were defined as below.

Primary evaluation period: In principle, the observation and testing period starting from the first day of administration of the investigational agent up to weeks 32, 28, and 24 for groups A, B, and C, respectively, at which time the serum SA237 concentrations were expected to be eliminated. However, in the case when the serum SA237 concentration was confirmed undetectable level and administration in the extension period was started before the end of the above period, the primary evaluation period would be set to the period until the observation and testing before the first administration in the extension period.

Extension period: Starting from the initial administration in the extension period following completion of the primary evaluation period, and up to the observation and testing on week 24 of the extension period.

Post-observation period: Starting from completion of observation and testing on week 24 of the extension period and up to week 32.

Results: Graphs indicating pharmacokinetics in this study are shown in FIG. 1. The trough levels of the serum SA237 concentration were roughly constant from week 4 and onwards in both the primary evaluation period for group A and in the extension period. On the other hand, the serum SA237 concentrations in groups B and C during the primary evaluation period decreased from week 8 and onwards. Since the primary evaluation period and the extension period did not show significant differences in the serum SA237 concentration and $AUC_{0-2W}$ up to week 8, the pharmacokinetics did not change when SA237 administration was interrupted and then resumed.

(2) Pharmacodynamic Evaluations

Figure 2:
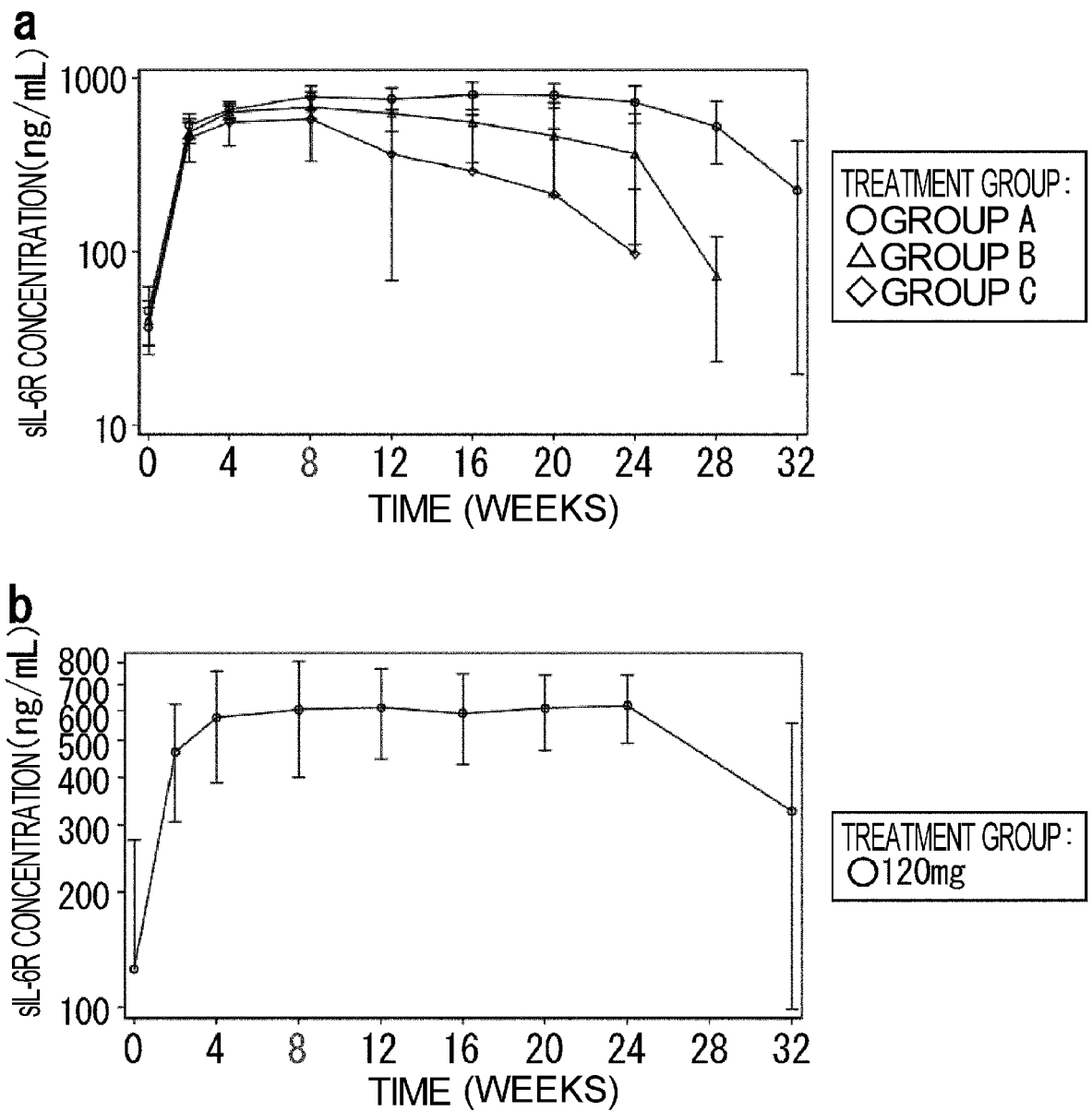
FIG. 2 indicates changes in the mean value (and standard deviation) of the serum sIL-6R concentration which is pharmacodynamic marker of SA237.
Figure 3:
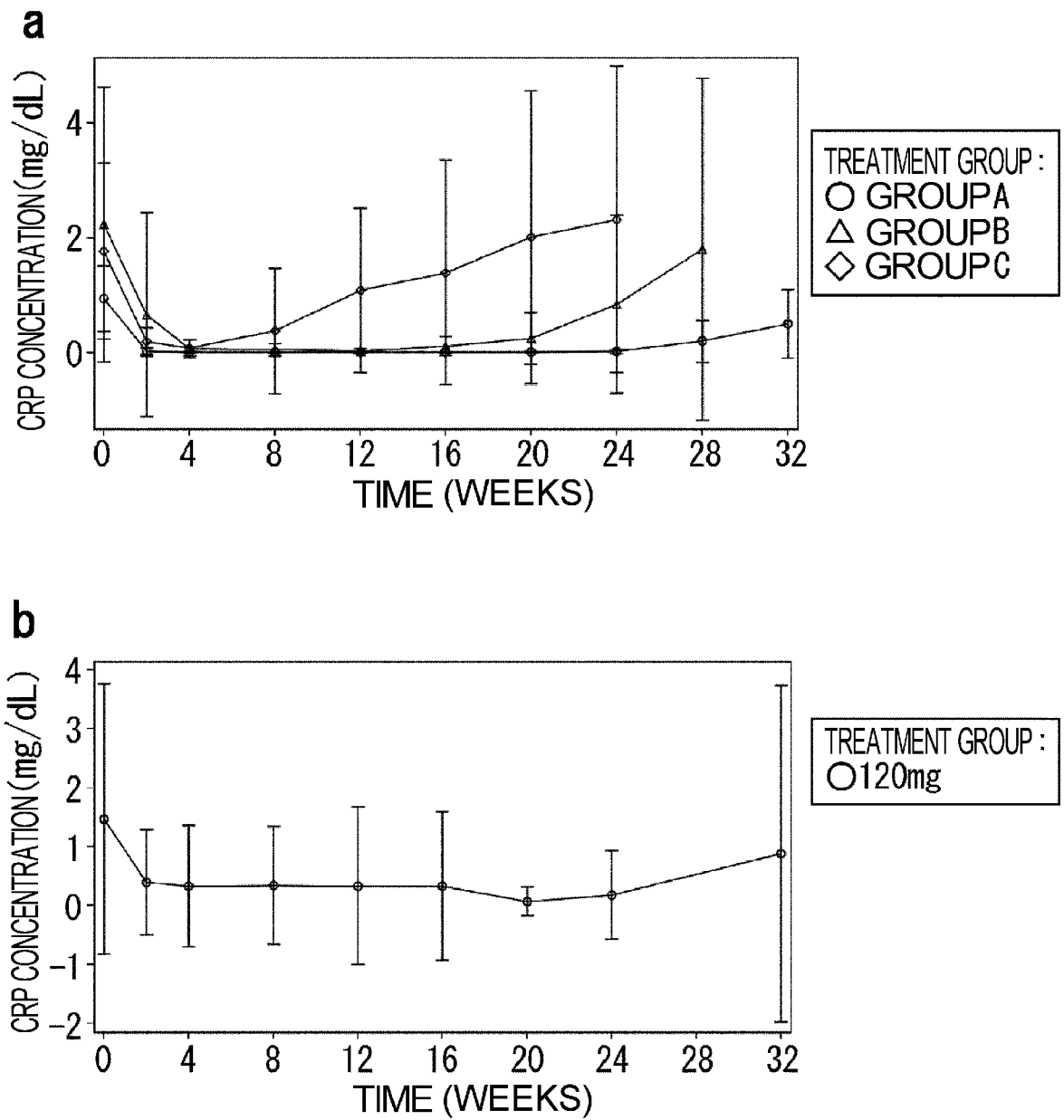
FIG. 3 indicates change in the mean value (and standard deviation) of the serum CRP concentration which is pharmacodynamic maker of SA237.

Results: Graphs from pharmacodynamic evaluations in this study are shown in FIGS. 2 and 3. From week 8 to week 20 in group A during the primary evaluation period, and from week 8 to week 24 during the extension period, where the serum SA237 concentration was maintained at a constant level, and the serum sIL-6R concentration was also maintained at a roughly constant level. On the other hand, from week 8 and onwards in groups B and C during the primary evaluation period, the serum concentration of sIL-6R, which is a PD marker for IL-6 inhibition, decreased along with the reduction in the SA237 concentration.

During the primary evaluation period, CRP, which is a PD marker for IL-6 inhibition, was lower than the lower limit of quantification (0.005 mg/dL) from week 4 to week 20 in approximately half of the subjects in group A, and the mean also remained low around 0.01 mg/dL. The value increased to 0.1 mg/dL or higher from week 16 and onwards in group B and from week 8 and onwards in group C. Percentage of CRP normalization (0.3 mg/dL or less) also showed a trend similar to the shift in the mean. The percentages at week 4 for each of the groups were 81.8% to 90.9%; and subsequently, when the percentages at week 20 were compared to those of week 8, group A did not show change from 100%, group B showed a change from 81.8% to 80.0% and was about the same, and group C showed a decrease from 90.9% to 33.3%. In most subjects and time points, CRP was considered to be decreased from the baseline level, as long as the serum SA237 concentration is quantifiable (0.2 µg/mL).

(3) Efficacy

Evaluation method: DAS28 (Modified disease activity score based on 28 joint counts) is an indicator for evaluating the activity of rheumatoid arthritis, which is calculated from the following equation using the tender joint count (TJC) and swollen joint count (SJC) in the 28 joints, ESR, and the "patient global assessment". The change in the DAS28 from the start of administration until the final day of observation was examined. Summary statistics (mean, standard deviation, median, minimum value, and maximum value) were calculated for each group and each period. Furthermore, the rate of clinical remission was calculated.

| TWENTY EIGHT JOINTS EXAMINED FOR DAS28 | |
| --- | --- |
| JOINT REGIONS | JOINT COUNT |
| SHOULDER JOINTS | 2 |
| ELBOW JOINTS | 2 |
| WRISTS | 2 |
| KNUCKLES (EXCLUDING DIP JOINTS) | 20 |
| KNEE JOINTS | 2 |
| Modified DAS based on 28 Joint Count = DAS28 | |
| DAS28 = $0.56 \sqrt{TJC} + 0.28 \sqrt{SJC} + 0.7 \times \ln ESR + 0.014 \times GH$ | |

ACR 20%, 50%, and 70% improvement criteria (ACR20, ACR50, and ACR70) were evaluated as below.

| ACR IMPROVEMENT CRITERIA |
| --- |
| Among the seven parameters shown below, ACR20 has a positive outcome when ≥20% improvement in tender or swollen joint counts were achieved as well as ≥20% improvement in three of the other five parameters. ACR50 and ACR70 have positive outcomes when 50% and 70% improvements in the above parameters for ACR20 were achieved, respectively. |

| | |
| --- | --- |
| (1) | SWOLLEN JOINT COUNT (66 JOINTS) |
| (2) | TENDER JOINT COUNT (68 JOINTS) |
| (3) | PAIN ASSESSMENT BY THE PATIENT |
| (4) | GENERAL HEALTH ASSESSMENT BY THE PATIENT |
| (5) | GENERAL HEALTH ASSESSMENT BY THE PHYSICIAN |
| (6) | EVALUATION OF ACTIVITY OF DAILY LIVING BY THE PATIENT (JAPANESE HEALTH ASSESSMENT QUESTIONNAIRE (JHAQ)) |
| (7) | CRP OR ESR |

Results: The time course of DAS28 scores in the primary evaluation period, which indicates the efficacy in this examination, are shown below in Table 4.

TABLE 4

| STATISTICAL VALUES OF DAS28 IN EACH VISIT | GROUP A 120 mg (N = 11) | GROUP B 60 mg (N = 11) | GROUP C 30 mg (N = 11) |
| --- | --- | --- | --- |
| CHANGE FROM THE BASELINE AT WEEK 4 | | | |
| n | 11 | 11 | 11 |
| MEAN | −1.85 | −1.95 | −1.46 |
| STANDARD DEVIATION | 0.71 | 1.06 | 0.71 |
| AT WEEK 8 | | | |
| n | 11 | 11 | 11 |
| MEAN | −2.73 | −2.93 | −2.35 |
| STANDARD DEVIATION | 1.12 | 1.40 | 0.74 |
| AT WEEK 12 | | | |
| n | 11 | 11 | 11 |
| MEAN | −2.94 | −2.67 | −2.19 |
| STANDARD DEVIATION | 1.22 | 1.59 | 1.15 |
| AT WEEK 16 | | | |
| n | 11 | 11 | 11 |
| MEAN | −3.13 | −2.56 | −1.66 |
| STANDARD DEVIATION | 1.33 | 1.79 | 1.68 |
| AT WEEK 20 | | | |
| n | 11 | 11 | 11 |
| MEAN | −3.29 | −2.63 | −1.25 |
| STANDARD DEVIATION | 1.34 | 1.92 | 1.73 |

DAS28 showed improvement in week 8. After the beginning of administration of different doses (at week 8) in the primary evaluation period, group A showed further improvement in DAS28, group B did not show a significant change, and group C showed a tendency to return to the baseline score.

The frequency of 20% improvement as per ACR criteria was 70.0% to 81.8% in each of the groups at week 8, the frequency of 50% improvement was 40.0% to 50.0%, and the frequency of 70% improvement was 18.2% to 30.0%. At week 20 compared to at week 8, the 20% improvement frequency was maintained in groups A and B, but decreased in group C. The 50% and 70% improvement frequencies at week 20 in group A increased to 72.7% (8/11 cases) and 54.5% (6/11 cases), respectively, compared to the values at week 8; however, no significant changes were observed in groups B and C.

(4) Immunogenicity and Pharmacokinetics, Pharmacodynamic Evaluation, Efficacy and Safety in the Antibody-Positive Cases Anti-SA237 antibodies were detected in one single case for each of groups B and C, that is, 2/33 cases in total. In these two cases, the serum SA237 concentration during the extension period after the anti-SA237 antibodies were detected was lower than the lower limit of quantification, and from the time that antibodies were detected and onwards, the increase in the soluble IL-6 receptor (sIL-6R) concentration and decrease in the CRP concentration due to SA237 administration were not observed, and DAS28, CDAI, and SDAI were increased. An adverse event, which was mild diabetes, was observed in one out of these two cases after the antibodies were detected. This adverse event was not an allergic reaction, but was an exacerbation of complications. A safety problem was not observed in repeatedly administering SA237 to both of the subjects after the antibodies were detected.

(5) Conclusion

When 120 mg of SA237 was administered to RA patients three times with two-week intervals, followed by three 120-mg administrations with 4-week intervals from week 8 and onwards, a stable serum drug concentration was maintained from week 4 to four weeks after the final administration. This resulted in high serum sIL-6R concentration and low CRP, and stable improvement of all items for efficacy evaluation including DAS28. The incidence of an anti-SA237 antibody for the entire clinical study was 6.1% (2/33 cases), and in the cases where an anti-SA237 antibody was detected, the serum SA237 concentration was found to decrease after detection of the anti-SA237 antibody, but safety problems were not observed and the immunogenicity was considered acceptable. Accordingly, there were no safety concern in this administration regimen.

INDUSTRIAL APPLICABILITY

The pharmaceutical compositions or regimen of the present invention can solve the immunogenic problem of anti-drug antibody generation, decrease side-effects, and provide a pharmaceutical composition which presents higher therapeutic effects with less patient burden since it does not expose the patient to high doses.

The invention claimed is:

1. A method of treating an IL-6-related disease with an anti-IL-6 receptor antibody comprising a heavy chain variable region comprising the amino acid sequence of SEQ ID NO: 1 and a light chain variable region comprising the amino acid sequence of SEQ ID NO: 2, the method comprising:

administering, during an initial period, two to five sequential doses of the antibody to a human patient who has the IL-6-related disease, wherein the doses administered during the initial period are spaced by a first dosing interval that is in the range of one to two weeks, and wherein each dose is a selected dosage amount of the antibody that does not vary and is in the range of 50 mg to 800 mg;

after the final dose administration of the initial period, waiting a second dosing interval that is twice the length of the first dosing interval and then administering a dose of the antibody in the selected dosage amount.

2. The method of claim 1, wherein multiple consecutive doses are administered after the final dose administration of the initial period, and are spaced by the second dosing interval.

3. The method of claim 2, wherein the first dosing interval is two weeks, and the second dosing interval is four weeks.

4. The method of claim 1, wherein the antibody comprises a heavy chain comprising the amino acid sequence of SEQ ID NO: 3 and a light chain comprising the amino acid sequence of SEQ ID NO: 4.

5. The method of claim 4, wherein the first dosing interval is two weeks, and the second dosing interval is four weeks.

6. The method of claim 1, wherein the initial period is four weeks in length and the first dosing interval is two weeks in length.

7. The method of claim 1, wherein the IL-6-related disease is rheumatoid arthritis or juvenile idiopathic arthritis.

8. The method of claim 7, wherein the first dosing interval is two weeks, and the second dosing interval is four weeks.

9. The method of claim 1, wherein the antibody is SA237.

10. The method of claim 9, wherein the first dosing interval is two weeks, and the second dosing interval is four weeks.

11. The method of claim 1, wherein the first dosing interval is two weeks.

12. The method of claim 1, wherein a total of three doses are administered during the initial period, the first dosing interval is two weeks, and the second dosing interval is four weeks.

13. The method of claim 12, wherein the selected dosage amount is 120 mg.

14. The method of claim 1, wherein the selected dosage amount is 120 mg.

15. The method of claim 14, wherein the first dosing interval is two weeks, and the second dosing interval is four weeks.

16. The method of claim 1, wherein each administration is an intravenous administration.

17. The method of claim 1, wherein each administration is a subcutaneous administration.

18. The method of claim 17, wherein the first dosing interval is two weeks, and the second dosing interval is four weeks.

19. The method of claim 1, wherein the IL-6-related disease is selected from the group consisting of rheumatoid arthritis, juvenile idiopathic arthritis, systemic-onset juvenile idiopathic arthritis, Castleman's disease, systemic lupus erythematosus (SLE), lupus nephritis, Crohn's disease, lymphoma, ulcerative colitis, anemia, vasculitis, Kawasaki disease, Still's disease, amyloidosis, multiple sclerosis, transplantation, age-related macular degeneration, ankylosing spondylitis, psoriasis, psoriatic arthritis, chronic obstructive pulmonary disease (COPD), IgA nephropathy, osteoarthritis, asthma, diabetic nephropathy, graft-versus-host disease (GVHD), endometriosis, hepatitis (NASH), myocardial infarction, arteriosclerosis, sepsis, osteoporosis, diabetes, multiple myeloma, prostate cancer, kidney cancer, B-cell non-Hodgkin's lymphoma, pancreatic cancer, lung cancer, esophageal cancer, colon cancer, cancer cachexia, cancer nerve invasion, myocardial infarction, myopic choroidal neovascularization, idiopathic choroidal neovascularization, uveitis, chronic thyroiditis, delayed hypersensitivity, contact dermatitis, atopic dermatitis, mesothelioma, polymyositis, dermatomyositis, panuveitis, anterior uveitis, intermediate uveitis, scleritis, keratitis, orbital inflammation, optic neuritis, diabetic retinopathy, proliferative vitreoretinopathy, dry eye, post-operative inflammation, neuromyelitis optica, myasthenia gravis, and pulmonary hypertension.

20. The method of claim 19, wherein the first dosing interval is two weeks, and the second dosing interval is four weeks.

21. The method of claim 1, wherein, when compared to an alternate treatment in which a human patient receives one and only one dose of the anti-IL-6 receptor antibody, and that one and only one dose is of the selected dosage amount and is administered subcutaneously, the method results in a lower likelihood that anti-antibodies that bind to the anti-IL-6 receptor antibody will be generated.

22. A method for treating an IL-6 related disease, the method comprising:
administering a pharmaceutical composition comprising an anti-IL-6 receptor antibody subcutaneously to a human patient who has an IL-6 related disease, wherein the pharmaceutical composition is administered to the patient three times with two-week intervals between sequential administrations; and
after the third administration, administering the pharmaceutical composition to the patient with a four-week interval between administrations,
wherein the anti-IL-6 receptor antibody comprises a heavy chain variable region comprising the amino acid sequence of SEQ ID NO: 1 and a light chain variable region comprising the amino acid sequence of SEQ ID NO: 2.

23. The method of claim 22, wherein the antibody is SA237.

24. The method of claim 22, wherein the amount of the antibody in the pharmaceutical composition that is administered to the patient in each administration does not vary and is in the range of 50 mg to 800 mg.

25. The method of claim 22, wherein the IL-6-related disease is selected from the group consisting of rheumatoid arthritis, juvenile idiopathic arthritis, systemic-onset juvenile idiopathic arthritis, Castleman's disease, systemic lupus erythematosus (SLE), lupus nephritis, Crohn's disease, lymphoma, ulcerative colitis, anemia, vasculitis, Kawasaki disease, Still's disease, amyloidosis, multiple sclerosis, transplantation, age-related macular degeneration, ankylosing spondylitis, psoriasis, psoriatic arthritis, chronic obstructive pulmonary disease (COPD), IgA nephropathy, osteoarthritis, asthma, diabetic nephropathy, graft-versus-host disease (GVHD), endometriosis, hepatitis (NASH), myocardial infarction, arteriosclerosis, sepsis, osteoporosis, diabetes, multiple myeloma, prostate cancer, kidney cancer, B-cell non-Hodgkin's lymphoma, pancreatic cancer, lung cancer, esophageal cancer, colon cancer, cancer cachexia, cancer nerve invasion, myocardial infarction, myopic choroidal neovascularization, idiopathic choroidal neovascularization, uveitis, chronic thyroiditis, delayed hypersensitivity, contact dermatitis, atopic dermatitis, mesothelioma, polymyositis, dermatomyositis, panuveitis, anterior uveitis, intermediate uveitis, scleritis, keratitis, orbital inflammation, optic neuritis, diabetic retinopathy, proliferative vitreoretinopathy, dry eye, post-operative inflammation, neuromyelitis optica, myasthenia gravis, and pulmonary hypertension.

26. The method of claim 22, wherein, when compared to an alternate treatment in which a human patient receives one and only one dose of the anti-IL-6 receptor antibody, and that one and only one dose is 120 mg and is administered subcutaneously, the method results in a lower likelihood that anti-antibodies that bind to the anti-IL-6 receptor antibody will be generated.

27. The method of claim 22, wherein the pharmaceutical composition is administered to the patient multiple times after the third administration, spaced at four-week intervals.

28. The method of claim 22, wherein the antibody comprises a heavy chain comprising the sequence of SEQ ID NO:3 and a light chain comprising the sequence of SEQ ID NO:4.

29. The method of claim 22, wherein the amount of the antibody in the pharmaceutical composition that is administered to the patient in each administration is 120 mg.

* * * * *